US008012493B2

(12) United States Patent
Fried et al.

(10) Patent No.: US 8,012,493 B2
(45) Date of Patent: Sep. 6, 2011

(54) MALARIA VACCINES

(75) Inventors: Michal Fried, Seattle, WA (US);
Patrick E Duffy, Seattle, WA (US);
Susan Francis, Seattle, WA (US); Jason P Wendler, Lincoln, NE (US); Theonest K Mutabingwa, Muheza (TZ); Andrew Oleinikov, Mill Creek, WA (US)

(73) Assignees: Seattle Biomedical Research Institute, Seattle, WA (US); The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/633,474

(22) Filed: Dec. 8, 2009

(65) Prior Publication Data

US 2010/0172929 A1    Jul. 8, 2010

Related U.S. Application Data

(60) Division of application No. 12/006,784, filed on Jan. 3, 2008, now Pat. No. 7,655,247, which is a continuation of application No. 11/501,465, filed on Aug. 8, 2006, now abandoned.

(60) Provisional application No. 60/706,733, filed on Aug. 9, 2005, provisional application No. 60/726,584, filed on Oct. 14, 2005.

(51) Int. Cl.
*A61K 39/015* (2006.01)

(52) U.S. Cl. ............... 424/272.1; 424/185.1; 424/269.1; 530/350

(58) Field of Classification Search ........................ None
See application file for complete search history.

(56) References Cited

OTHER PUBLICATIONS

Sulston et al (Nature. 2002. 419:527-531).*
Wood (Guide to Molecular Cloning Techniques. vol. 152. 187. Section IX. Chapter 49, pp. 443-457).*
Duffy & Fried (2003) Antibodies that inhibit *Plasmodium falciparum* adhesion to chondroitin sulfate A are associated with increased birth weight and the gestational age of newborns, Infect. Immun. 71:6620-3.
Duffy et al. (2005) Malaria vaccines: using models of immunity and functional genomics tools to accelerate the development of vaccines against *Plasmodium falciparum*, Vaccine 23:2235-42.
Fried et al. (2004) Mass spectrometric analysis of *Plasmodium falciparum* erythrocyte membrane protein-1 variants expressed by placental malaria parasites, Proteomics 4:1086-93.
Gardner et al. (2002) Genome sequence of the human malaria parasite *Plasmodium falciparum*, Nature 419:498-511.
Hall et al. (2002) Sequence of *Plasmodium falciparum* chromosomes 1, 3-9 and 13, Nature 419:527-31.
Hamlin et al. (submitted Feb. 1999 to the EMBL/GenBank/DDBJ databases; Accession No. Q81FM6).

* cited by examiner

*Primary Examiner* — Jennifer Graser
(74) *Attorney, Agent, or Firm* — Karen Blochlinger

(57) ABSTRACT

The invention provides isolated placental *P. falciparum* polypeptides comprising an amino acid sequence selected from the group consisting of SEQ ID NOs:1-4 and 6-24, and immunogenic derivatives thereof. The invention also provides isolated nucleic acid molecules encoding the placental *P. falciparum* polypeptides of the invention, compositions comprising one or more placental *P. falciparum* polypeptides of the invention, methods for inducing an immune response against the placental *P. falciparum* polypeptides, and methods for treating and diagnosing placental malaria.

3 Claims, No Drawings

MALARIA VACCINES

CROSS-REFERENCES TO RELATED APPLICATIONS

This application is a divisional application of U.S. patent application Ser. No. 12/006,784, filed on Jan. 3, 2008, now U.S. Pat. No. 7,655,247, which is a continuation of application Ser. No. 11/501,465 filed on Aug. 8., 2006, now abandoned, which claims the benefit of U.S. Provisional Application No. 60/706,733, filed Aug. 9, 2005, and U.S. Provisional Application No. 60/726,584, filed Oct. 14, 2005, both of which are incorporated herein by reference.

STATEMENT OF GOVERNMENT RIGHTS

This invention was made with government support under RO1 AI 43680-04 and RO1 AI 52059 awarded by the National Institutes of Health. The government has certain rights in the invention.

FIELD OF THE INVENTION

This invention relates to proteins that are expressed on the surface of *Plasmodium* parasites and/or the surface of red blood cells infected by *Plasmodium* parasites, and their use in the diagnosis, treatment, and prevention of malaria.

BACKGROUND OF THE INVENTION

Malaria has a tremendous impact on human health, killing millions annually and the disease is a major impediment for social and economic development of nations in malaria-endemic areas, particularly in sub-Saharan Africa (Sachs & Malaney (2002) *Nature* 415:680-85). Malaria is a mosquito-borne disease that is transmitted by inoculation of the *Plasmodium* parasite sporozoite stage. Sporozoites invade hepatocytes (Kappe et al. (2003) *Trends Parasitol.* 19:135-43), transform into liver stages, and subsequent liver stage development ultimately results in release of pathogenic merozoites that initiate the blood stage cycle of infection (Short & Garnham (1948) *Nature* 161:126).

Protection against blood stage malaria can be passively transferred by antibodies. Effectiveness of passive transfer of IgG between adults and children living in different geographic regions indicate that the antigens that are targeted by antibodies that protect against blood stage malaria are conserved (see Duffy et al. (2005) *Vaccine* 23 (17-18):2235-42). The best evidence that naturally occurring immunity against blood stage malaria targets the IRBC surface comes from studies of pregnancy malaria. In areas of stable malaria transmission, adults enjoy immunity that limits parasitemia and prevents disease. Women become more susceptible during pregnancy, and previously this was ascribed to pregnancy-related immunomodulation that develops to prevent rejection of the fetal allograft. However, susceptibility is greatest in primigravid women and diminishes over successive pregnancies, suggesting an acquired immune response to an antigenically distinct microbe. Placental isolates of *P. falciparum* commonly bind to chondroitin sulfate A (CSA) expressed on the surface of the syncytiotrophoblast (the cells lining the maternal vascular space in the placenta), and this phenotype is uncommon among isolates obtained from non-pregnant individuals (Fried & Duffy (1996) *Science* 272:1502-4). The distinct binding phenotype renders pregnant women naïve to this parasite population during their first pregnancy (primigravidas). Women with multiple pregnancies (multigravidas) residing in areas of stable malaria transmission develop antibodies that inhibit parasite adhesion to CSA (Fried et al. (1998) *Nature* 395:851-2). These anti-adhesion antibodies are associated with a reduced mass of parasites in the placenta, and substantial improvements in fetal development (Duffy & Fried (2003) *Infect. Immun.* 71:6620-3). Because CSA-binding parasites cross-react with sera donated by mothers throughout Asia and Africa, the antigen targeted by protective antibodies is presumed to have conserved features or limited diversity.

There is a need in the art for vaccines that protect against malaria infection and disease. There is also a need in the art for diagnostic markers for malaria. The present invention addresses these needs and others.

SUMMARY OF THE INVENTION

One aspect of the invention provides isolated placental *P. falciparum* polypeptides. In some embodiments, the isolated placental *P. falciparum* polypeptides comprise an amino acid sequence selected from the group consisting of SEQ ID NOs: 1-4 and 6-24. In some embodiments, the placental *P. falciparum* proteins are preferentially recognized by sera from multigravidas than by sera from primigravidas and/or sera from males. The isolated placental *P. falciparum* polypeptides of the invention may be recombinant or synthetic polypeptides. In some embodiments, the polypeptides of the invention are immunogenic derivatives of polypeptides comprising an amino acid sequence selected from the group consisting of SEQ ID NOs: 1-4 and 6-24.

Another aspect of the invention provides isolated nucleic acid molecules encoding the placental *P. falciparum* polypeptides of the invention. Thus, some embodiments provide an isolated nucleic acid molecule encoding a polypeptide comprising an amino acid sequence selected from the group consisting of SEQ ID NOs:1-4 and 6-24, and immunogenic derivatives thereof.

A further aspect of the invention provides compositions comprising one or more placental *P. falciparum* polypeptides of the invention and a pharmaceutically acceptable carrier. Thus, some embodiments provide an immunogenic composition comprising an isolated polypeptide and a pharmaceutically acceptable carrier, wherein the isolated polypeptide comprises an amino acid sequence selected from the group consisting of SEQ ID NOs:1-4 and 6-24, and immunogenic derivatives thereof. In some embodiments, the compositions of the invention are immunogenic compositions for inducing immune responses, such as vaccine compositions.

In another aspect, the invention provides methods for inducing an immune response against placental *P. falciparum* parasites, comprising administering an immunogenic composition comprising an effective amount of one or more placental *P. falciparum* polypeptides of the invention. Thus, in some embodiments the invention provides a method for inducing an immune response in a mammalian subject against *Plasmodium falciparum*, comprising administering to the host a composition comprising an effective amount of at least one isolated polypeptide selected from the group consisting of SEQ ID NOs:1-4 and 6-24, and immunogenic derivatives thereof.

Yet another aspect of the invention provides methods for treating a subject in need thereof, comprising administering to a subject in need thereof an immunogenic composition comprising an effective amount of one or more placental *P. falciparum* polypeptides of the invention. Thus, in some embodiments the invention provides a method for treating a human subject in need thereof, comprising administering to a human subject an immunogenic composition comprising at least one isolated polypeptide selected from the group consisting of SEQ ID NOs:1-4 and 6-24, and immunogenic derivatives thereof.

The invention also provides expression vectors encoding the placental *P. falciparum* polypeptides of the invention, host cells comprising such expression vectors; antibodies that bind specifically to the placental *P. falciparum* polypeptides of the invention, or immunogenic derivatives thereof; and diagnostic assays for detecting the presence of the placental *P. falciparum* polypeptides of the invention, or nucleic acid molecules encoding them.

DETAILED DESCRIPTION OF THE PREFERRED EMBODIMENT

In one aspect, the invention provides novel proteins expressed by placental *P. falciparum* parasites. In some embodiments, these proteins are expressed on the surface of red blood cells infected by *Plasmodium falciparum* parasite, as shown in EXAMPLE 1. In some embodiments, the genes encoding these proteins are upregulated in placental *P. falciparum* parasites, as shown in EXAMPLE 4. Placental *P. falciparum* proteins are preferentially recognized by sera from multigravidas than by sera from primigravidas and/or sera from males, as shown in EXAMPLES 2 and 5.

Thus, one aspect of the invention provides isolated placental *P. falciparum* polypeptides. In some embodiments, the isolated placental *P. falciparum* polypeptides comprise an amino acid sequence selected from the group consisting of SEQ ID NOs:1-4 and 6-24. The sequences of these proteins, the nucleotide sequences encoding them, and annotation information may be obtained from the *Plasmodium* Genome Database (http://plasmodb.org/; Kissinger et. al (2002) *Nature* 419: 490-492) under the protein/gene ID numbers provided in Tables 1, 2 and 4, and are herein incorporated by reference. The isolated placental *P. falciparum* polypeptides of the invention may be recombinant or synthetic full-length polypeptides, or immunogenic derivatives thereof, as further described below. Accordingly, some embodiments of the invention provide an isolated polypeptide comprising an amino acid sequence selected from the group consisting of SEQ ID NOs:1-4 and 6-24, and immunogenic derivatives thereof.

As used herein, the term "polypeptide" refers to a polymer of amino acids and does not refer to a specific length of the product; thus, peptides, oligopeptides, and proteins are included within the definition of polypeptide. This term also includes post-expression modifications of the polypeptide, for example, glycosylations, acetylations, phosphorylations, and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The placental *P. falciparum* polypeptides of the invention may be full-length polypeptides, immunogenic derivatives or domains of full-length polypeptides, or immunogenic variants thereof. As used herein, the term "immunogenic" refers to the ability of a polypeptide to elicit a humoral and/or cellular immune response, whether alone or when linked to a carrier, in the presence or absence of an adjuvant. Thus, an immunogenic portion of a full-length placental *P. falciparum* polypeptide of the invention refers to a portion of the full-length polypeptide that is capable of eliciting an immune response against the corresponding full-length polypeptide.

The term "immunogenic derivative or domain" encompasses any polypeptide that includes at least 5 to 8 amino acids (such as, for example, 10 to 50 amino acids or 30 to 200 amino acids) and that is capable of inducing an immune response to the full-length polypeptide, such as a truncated form, epitope, or other derivative. The term "epitope" refers to a linear array of 3 to 10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g., cysteines involved in disulfide bonding, glycosylation sites, etc.). A conformational epitope may also be formed by 2 or more essential regions of subunits of a homo-oligomer or hetero-oligomer. Other immunogenic derivatives may be prepared by the addition, deletion, substitution, or rearrangement of amino acids or by chemical modifications thereof.

Methods of predicting immunogenic regions in a polypeptide are well-known in the art. For example, a polypeptide sequence may be analyzed using the DNASTAR program by several algorithms, including prediction of hydrophilicity according to the Kyte-Doolittle method, surface probability according to the Emini method, and antigenicity according to the Jameson-Wolf method. Other epitope prediction approaches are known in the art (see, e.g., Moise & De Groot (2006) *Nat. Biotechnol.* 24(7):791-2).

In some embodiments, the immunogenic derivatives of the placental *P. falciparum* proteins of the invention include 5 to 10, 10 to 50, 20 to 200, or 40 to 300 contiguous amino acids of a full-length polypeptide comprising an amino acid sequence selected from the group consisting of SEQ ID NOs: 1-4 and 6-24. Exemplary immunogenic derivatives of the polypeptides of the invention include, but are not limited to, polypeptides comprising amino acids 572 to 877 of SEQ ID NO:11, amino acids 1 to 500 of SEQ ID NO:3, amino acids 50 to 750 of SEQ ID NO:4, amino acids 751-1471 of SEQ ID NO:4, amino acids 370 to 670 of SEQ ID NO:8, amino acids 2000 to 2500 of SEQ ID NO:8, or amino acids 34 to 347 of SEQ ID NO:13.

Immunogenic derivatives of the polypeptides of the invention, which may be useful in the preparation of vaccines, may be prepared by expression of the appropriate gene fragments or by peptide synthesis, using methods well known in the art, as further described below. Exemplary methods for recombinant expression of immunogenic derivatives of the invention are provided in EXAMPLES 3 and 5.

An immunogenic derivative may be a fusion polypeptide containing additional sequences encoding one or more epitopes for other *Plasmodium* immunogens, or other non-*Plasmodium* immunogens. Alternatively, the immunogenic derivative of the invention can be fused to a carrier polypeptide (such as Hepatitis B surface or core antigen) or to another carrier that has immunostimulating properties, as in the case of an adjuvant, or that otherwise enhances the immune response to the protein or derivative thereof, or that is useful in expressing, purifying or formulating the protein or derivative thereof. The proteins or immunogenic derivatives thereof which are useful in the invention may be chemically conjugated to a macromolecule using a conventional linking agent such as glutaraldehyde (Geerlings et al. (1988) *J. Immunol. Methods* 106: 239-244).

In some embodiments, the placental *P. falciparum* polypeptides of the invention include immunogenic derivatives with more than 80% amino acid sequence identity (such as more than 90% sequence identity, more than 95% amino acid sequence identity, or more than 99% sequence identity) to the sequences defined in SEQ ID NOs:1-4 and 6-23. The terms "identical" or percent "identity", in the context of two or more amino acid sequences, refer to two or more sequences or subsequences that are the same or have a specified percentage of amino acid residues that are the same, when compared and aligned for maximum correspondence over a comparison window, as measured using one of the following sequence comparison algorithms or by manual alignment and visual inspection.

It is recognized that amino acid positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, for example, the algorithm of Meyers & Millers (1988) *Computer Applic. Biol. Sci.* 4:11-17.

A "comparison window" includes reference to a segment of contiguous positions, such as between about 25 and about 600 positions, or between about 50 to 200 positions, or between about 100 and 150 positions, over which a sequence may be compared to a reference sequence of the same number of contiguous positions after the two sequences are optimally aligned. Methods of alignment of sequences for comparison are well-known in the art. Optimal alignment of sequences for comparison can be conducted, for example, by a local homology algorithm (Smith & Waterman (1981) *Adv. Appl. Math.* 2:482), by a global alignment algorithm (Needleman & Wunsch (1970) *J. Mol. Biol.* 48:443), by search for similarity methods (Pearson & Lipman (1988) *Proc. Natl. Acad Sci. USA.* 85:2444; Altschul et al. (1997) *Nucl. Acids Res.* 25(17): 3389-402), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., Current Protocols in Molecular Biology (1994) Ausubel et al., eds.). For example, BLAST protein searches can be performed using the)(BLAST program, score=50, wordlength=3 to obtain amino acid sequences that are more than 80% identical to the amino acid sequence of SEQ ID NOs:1-4 and 6-24.

One example of a useful algorithm implementation is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle (1987) *J. Mol. Evol.* 35:351-60. The method used is similar to the method described by Higgins & Sharp (1989) *CABIOS* 5:151-3. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

In some embodiments, the placental *P. falciparum* polypeptides of the invention include variants of the wild-type polypeptides. These variants fall into one or more of three classes: substitutional, insertional or deletional variants. These variants may be naturally occurring allelic or interspecies variants (e.g., variants from different *P. falciparum* strains), or they may be prepared by site-specific mutagenesis of nucleotides in the DNA encoding protein. Site-specific mutagenesis may be performed using cassette or PCR mutagenesis or other techniques well known in the art, to produce DNA encoding the variant, and thereafter expressing the DNA in recombinant cell culture. Variant target protein fragments having up to about 100-150 amino acid residues may be prepared by in vitro synthesis using established techniques. Conservative substitution tables providing functionally similar amino acids are well known in the art (Henikoff & Henikoff (1992) *Proc. Natl. Acad. Sci. U.S.A.* 89:10915-9)

Amino acid substitutions are typically of single residues. Insertions usually will be on the order of from about 1 to about 20 amino acids, although considerably longer insertions may be tolerated. Deletions range from about 1 to about 20 residues, although in some cases, deletions may be much longer. Substitutions, deletions, and insertions or any combinations thereof may be used to arrive at a final derivative.

In some embodiments, the placental *P. falciparum* polypeptides of the invention are recombinant polypeptides. The term "recombinant polypeptide" refers to a protein produced by recombinant expression methods, such as, for example, in prokaryotic or eukaryotic host cells, or in cell-free in vitro expression systems, as described in detail below.

The placental *P. falciparum* polypeptides of the invention are typically expressed using an expression vector and purified. Expression vectors may be either self-replicating extrachromosomal vectors or vectors which integrate into a host genome. Generally, expression vectors include transcriptional and translational regulatory nucleic acid sequences operably linked to the nucleic acid encoding the target protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences may be contiguous or non-contiguous. Methods for linking DNA sequences are well-known in the art and include use of the polymerase chain reaction and ligation. The transcriptional and translational regulatory nucleic acid will generally be appropriate to the host cell used to express the target protein; for example, transcriptional and translational regulatory nucleic acid sequences from *E. coli* are preferably used to express the target protein in *E. coli.*

Numerous types of appropriate expression vectors, and suitable regulatory sequences are known in the art for a variety of host cells. Methods for expressing polypeptides are well known in the art (e.g., Sambrook et al. (1989) *Molecular Cloning, A Laboratory Manual*, 2nd ed., vol. 1-3, Cold Spring Harbor Laboratory; Berger and Kimmel (1987) *Guide to Molecular Cloning Techniques*, Methods in Enzymology, vol. 152, Academic Press, Inc., San Diego, Calif.; Ausubel et al. (1995) *Current Protocols in Molecular Biology*, John Wiley & Sons, Inc., NY)

In general, the transcriptional and translational regulatory sequences may include, but are not limited to, promoter sequences, ribosomal binding sites, transcriptional start and stop sequences, translational start and stop sequences, and enhancer or activator sequences. Promoter sequences encode either constitutive or inducible promoters. The promoters may be either naturally occurring promoters or hybrid promoters. Hybrid promoters, which combine elements of more than one promoter, are also known in the art.

An expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to a sequence in the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In addition, an expression vector may include a selectable marker gene to allow the selection of transformed host cells. Selection genes are well known in the art and will vary depending on the host cell used.

The placental *P. falciparum* polypeptides of the invention may be produced by culturing a host cell transformed with an expression vector containing nucleic acid encoding a placental *P. falciparum* polypeptide, under the appropriate conditions to induce or cause expression of the placental *P. falciparum* polypeptide. The conditions appropriate for protein expression will vary with the choice of the expression vector and the host cell, and will be easily ascertained by one skilled in the art using routine experimentation. For example, the growth and proliferation of the host cell may be optimized for the use of constitutive promoters in the expression vector, and appropriate growth conditions for induction are provided for use of an inducible promoter. In addition, in some embodiments, the timing of the harvest is important, for example, when using baculoviral systems. One of skill in the art will recognize that the coding sequences may be optimized for expression in the selected host cells.

Appropriate host cells include yeast, bacteria, archaebacteria, fungi, and insect and animal cells, including mammalian cells. Host cells include, but are not limited to, *Drosophila melanogaster* cells, *Saccharomyces cerevisiae* and other yeasts, *E. coli, Bacillus subtilis*, Sf9 cells, C129 cells, 293 cells, *Neurospora*, BHK, CHO, COS, HeLa cells, Hep G2 cells, THP1 cell line (a macrophage cell line), and human cells and cell lines.

In some embodiments, the placental *P. falciparum* polypeptides are expressed in mammalian cells. Mammalian expression systems are also known in the art, and include retroviral systems. Promoters from viral genes are frequently used in mammalian expression systems, because the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived from SV40.

The placental *P. falciparum* polypeptides of the invention may be cloned using DNA amplification methods, such as the polymerase chain method (PCR) (see e.g., Sambrook et al. (1989) *Molecular Cloning: A Laboratory Manual*, 2nd ed., Cold Spring Harbour, N.Y.; Berger & Kimmel (1987) *Methods in Enzymology*. Vol. 152: *Guide to Molecular Cloning Techniques*, Academic Press, Inc., San Diego, Calif.; Co et al. (1992) *J. Immunol.* 148:1149). Thus, for example, a nucleic acid molecule encoding a placental *P. falciparum* polypeptide may be PCR amplified using a sense primer containing one restriction site and an antisense primer containing another restriction site. This will produce a nucleic acid encoding the desired sequence or subsequence having terminal restriction sites. This nucleic acid can then easily be ligated into a vector having appropriate corresponding restriction sites. Suitable PCR primers are easily chosen by one of skill in the art based on the sequence to be expressed. Appropriate restriction sites can also be added by site-directed mutagenesis (see Gillman & Smith (1979) *Gene* 8: 81-97; Roberts et al. (1987) *Nature* 328: 731-4).

The methods of introducing exogenous nucleic acid into host cells are well known in the art, and will vary with the host cell used. Suitable techniques include, but are not limited to, dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, the placental *P. falciparum* polypeptides of the invention are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the target protein in bacteria. The placental *P. falciparum* polypeptide is either secreted into the growth media (gram-positive bacteria) or into the periplasmic space, located between the inner and outer membrane of the cell (gram-negative bacteria). The expression vector may also include an epitope tag providing for affinity purification of the target protein. The bacterial expression vector may also include a selectable marker gene to allow for the selection of bacterial strains that have been transformed. Suitable selection genes include genes that render the bacteria resistant to drugs such as ampicillin, chloramphenicol, erythromycin, kanamycin, neomycin and tetracycline. Selectable markers also include biosynthetic genes, such as those in the histidine, tryptophan, and leucine biosynthetic pathways. These components are assembled into expression vectors. Expression vectors for bacteria are well known in the art, and include vectors for *Bacillus subtilis, E. coli, Streptococcus cremoris*, and *Strep-*

*tococcus lividans*, among others. The bacterial expression vectors are transformed into bacterial host cells using techniques well known in the art, such as calcium chloride treatment, electroporation, and others. An exemplary method for expressing placental *P. falciparum* polypeptides of the invention using a bacterial expression system is described in EXAMPLES 2 and 3.

The placental *P. falciparum* polypeptides of the invention may also be produced in insect cells. Expression vectors for the transformation of insect cells, and in particular, baculovirus-based expression vectors, are well known in the art. The placental *P. falciparum* polypeptides may also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The placental *P. falciparum* polypeptides of the invention may be produced in a cell-free expression system in vitro using an expression vector containing nucleic acid encoding a placental *P. falciparum* polypeptide, under the appropriate conditions to induce or cause expression of the placental *P. falciparum* polypeptide in vitro. Cell-free in vitro expression systems are well known in the art. An exemplary method for expressing placental *P. falciparum* polypeptides of the invention using a cell-free in vitro expression system is described in EXAMPLE 3.

The placental *P. falciparum* polypeptides of the invention may also be made as a fusion proteins, using techniques that are well known in the art. For example, a placental *P. falciparum* polypeptides may be made as a fusion protein to increase expression or to link it with a tag polypeptide that provides an epitope to which an anti-tag antibody can selectively bind. Exemplary tags include the myc epitope and 6-histidine. The epitope tag is generally placed at the amino- or carboxyl-terminus of the target protein. The presence of such epitope-tagged forms of a target protein can be detected using an antibody against the tag polypeptide. Thus, the epitope tag enables the target proteins to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al. (1988) *Mol. Cell. Biol.* 8:2159-65); the c-myc tag and the 8F9, 3C7, 6E10, G4, B7 and 9E10 antibodies thereto (Evan et al. (1985) *Mol. Cell. Biol.* 5:3610-6); and the Herpes Simplex virus glycoprotein D (gD) tag and its antibody (Paborsky et al. (1990) *Prot. Eng.* 3(6):547-53). Other tag polypeptides include the Flag-peptide (Hopp et al. (1988) *BioTechnol.* 6:1204-10); the KT3 epitope peptide (Martin et al. (1992) *Science* 255:192-4); tubulin epitope peptide (Skinner et al. (1991) *J. Biol. Chem.* 266:15163-6); and the T7 gene 10 protein peptide tag (Lutz-Freyermuth et al. (1990) *Proc. Natl. Acad. Sci. USA.* 87:6393-7).

Covalent modifications of placental *P. falciparum* polypeptides are included within the scope of this invention. One type of covalent modification includes reacting targeted amino acid residues of a target protein with an organic derivatizing agent that is capable of reacting with selected side chains or the N- or C-terminal residues of a target protein. Derivatization with bifunctional agents is useful, for instance, for crosslinking a target protein to a water-insoluble support matrix or surface for use in screening assays. Commonly used crosslinking agents include, but are not limited to, 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

The placental *P. falciparum* polypeptides of the invention may be purified or isolated after expression. The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. For example, it means that the protein is at least 85% pure, such as at least 95% pure, such as at least 99% pure. The term "isolated polypeptides" also includes polypeptides in situ within recombinant host cells, since at least one component of the polypeptide natural environment will not be present. Generally, however, isolated polypeptide will be prepared by at least one purification step.

The placental *P. falciparum* polypeptides of the invention may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the target protein may be purified using an antibody column. Ultrafiltration and diafiltration techniques, in conjunction with protein concentration, are also useful. Suitable purification techniques are standard in the art (see generally R. Scopes (1982) *Protein Purification*, Springer-Verlag, N.Y.; Deutcher (1990) *Methods in Enzymology* vol. 182: *Guide to Protein Purification*, Academic Press, Inc. N.Y.). The degree of purification necessary will vary depending on the use of the polypeptide. In some instances no purification may be necessary.

Some embodiments of the invention provide synthetic placental *P. falciparum* polypeptides. Polypeptides having up to about 100-150 amino acid residues may be prepared by in vitro synthesis using established techniques. Synthetic polypeptides may be prepared by chemical synthesis (such as solid phase peptide synthesis) using methods known in the art, such as those described in Merrifield et al. (1964) *J. Am. Chem. Soc.* 85:2149, Houghten et al. (1985) *Proc. Natl. Acad. Sci. USA,* 82:51:32, and Stewart & Young (1984) Solid phase peptide synthesis, Pierce Chem Co., Rockford, Ill. Such polypeptides can be synthesized with or without a methionine on the amino terminus. Chemically synthesized placental *P. falciparum* proteins of the invention and immunogenic derivatives thereof may be oxidized using methods set forth in these references to form disulfide bridges. Further, peptidomimetics that structurally and/or functionally resemble a polypeptide embodiment may be made. Several approaches to make peptidomimetics that resemble polypeptides have been described (see, e.g., U.S. Pat. Nos. 5,288,707; 5,552, 534; 5,811,515; 5,817,626; 5,817,879; 5,821,231; and 5,874, 529).

Another aspect of the invention provides isolated nucleic acid molecules encoding the placental *P. falciparum* polypeptides of the invention. Thus, some embodiments provide an isolated nucleic acid molecule encoding a polypeptide comprising an amino acid sequence selected from the group consisting of SEQ ID NOs:1-4 and 6-24, and immunogenic derivatives thereof. The term "isolated nucleic acid molecule(s)" refers to a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) encoding placental *P. falciparum* polypeptides or immunogenic derivatives thereof. The sequence of these nucleic acid molecules may be different to the any naturally-occurring sequences encoding the placental *P. falciparum* polypeptides of the invention but that, due to the degeneracy of the genetic code, still encode a placental *P. falciparum* polypeptide. Of course, the genetic code is well known in the art. Thus, it would be routine for one skilled in the art to generate such degenerate variants.

Another aspect of the invention provides expression vectors encoding the placental *P. falciparum* polypeptides of the invention. Another aspect of the invention provides host cells comprising expression vectors encoding the placental *P. falciparum* polypeptides of the invention.

Another aspect of the invention provides antibodies that bind specifically to the placental *P. falciparum* polypeptides of the invention, or immunogenic derivatives thereof. The term "antibody" refers to an intact immunoglobulin, or to an antigen-binding portion of an immunoglobulin that competes with the intact antibody for specific binding to a protein or fragment of a protein of the present invention. Exemplary antibodies include polyclonal, monoclonal, humanized, bispecific, and heteroconjugate antibodies. Antigen-binding portions of an immunoglobulin of the present invention can be produced by various techniques including, but not limited to recombinant DNA techniques and enzymatic or chemical cleavage of intact antibodies.

An "isolated antibody" as used herein is an antibody that (1) is not associated with naturally-associated components, including other naturally-associated antibodies, that accompany it in its native state, (2) is free of other proteins from the same species, (3) is expressed by a cell from a different species, or (4) does not occur in nature. The terms "bind specifically" and "specific binding" refer to the ability of an antibody of the present invention to bind to a first molecular species in preference to binding to other molecular species with which the antibody and first molecular species are admixed. An antibody is said specifically to "recognize" a first molecular species when it can bind specifically to that first molecular species. In the present invention the first molecular species is a placental *P. falciparum* polypeptide of the invention, or immunogenic derivative thereof.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a placental *P. falciparum* polypeptide of the invention, or an immunogenic derivative thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods, such as those described by Kohler & Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Suitable immortalized cell lines for the production of monoclonal antibodies are well-known in the art (see, e.g., Goding (1986) Monoclonal Antibodies: Principles and Practice, Academic Press, pp. 59-103; Kozbor (1984) *J. Immunol.* 133:3001; Brodeur et al. (1987) Monoclonal Antibody Production Techniques and Applications, Marcel Dekker, Inc., New York, pp. 51-63).

The binding specificity of monoclonal antibodies produced by the hybridoma cells may be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody may, for example, be determined by the Scatchard analysis of Munson & Pollard (1980) *Anal. Biochem.* 107:220.

The monoclonal antibodies may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567, herein incorporated by reference. Monoclonal antibodies may be isolated using phage display libraries (Hoogenboom & Winter (1991) *J. Mol. Biol.* 227:381; Marks et al. (1991) *J. Mol. Biol.* 222:581).

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The antibodies may also be human or humanized antibodies, bispecific antibodies, or heteroconjugate antibodies. Methods for preparing human or humanized antibodies, bispecific antibodies, or heteroconjugate antibodies are well known in the art and described, for example, in Desnoyers et al., U.S. Pat. No. 7,084,258, herein incorporated by reference.

The antibodies that specifically bind to the placental *P. falciparum* polypeptides of the invention may be used in diagnostic assays, for example, to detect the presence of placental malaria parasites, or as therapeutic or prophylactic agents for treating or preventing infection by *P. falciparum*.

The term "therapeutic agent" refers to an agent capable of treating a malaria infection. The term "prophylactic agent" refers to an agent capable of preventing an infection by *P. falciparum*. In some embodiments, the antibodies may be used to treat subjects at risk of developing or suffering from pregnancy malaria by passive immunization.

In general, this will comprise administering a therapeutically or prophylactically effective amount of one or more antibodies of the present invention to a subject susceptible to malaria or a subject exhibiting a malaria infection. Any active form of the antibody can be administered, including Fab and F(ab')$_2$ fragments. Treatment of individuals having malaria infection may comprise the administration of a therapeutically effective amount of antibodies of the present invention. The dosage of administered antibodies will vary depending upon such factors as the patient's age, weight, height, sex, general medical condition, previous medical history, as well as other factors know to those of skill in the art. An appropriate effective amount can be readily determined using only routine experimentation. Effective amounts and routes of administration for therapeutic and prophylactic applications are further described below.

Another aspect of the invention provides compositions comprising one or more placental *P. falciparum* polypeptides of the invention and a pharmaceutically acceptable carrier. Thus, some embodiments provide an immunogenic composition comprising an isolated polypeptide and a pharmaceutically acceptable carrier, wherein the isolated polypeptide comprises an amino acid sequence selected from the group consisting of SEQ ID NOs:1-4 and 6-24, and immunogenic derivatives thereof. In some embodiments, the compositions of the invention are immunogenic compositions for inducing immune responses, such as vaccine compositions. A "vaccine" is an immunogenic composition capable of eliciting protection against infection by *Plasmodium* parasites and/or malarial disease, whether partial or complete. A vaccine that is used for treatment of an infected individual may be referred to as a therapeutic vaccine. The immunogenic compositions of the invention may also be used to elicit antibodies in a species that is not infectable by *P. falciparum*, for example to raise antibodies in rabbits or mice.

The invention further provides methods for preparing an immunogenic composition, by suspending and packaging one or more placental *P. falciparum* polypeptides of the invention in a suitable pharmaceutically acceptable carrier. Suitable pharmaceutically acceptable carrier include sterile water or sterile physiological salt solution, particularly phosphate buffered saline (PBS), as is well known in the art.

The immunogenic compositions of the invention generally also include an adjuvant. Adjuvants are well known in the art (see, for example, *Vaccine Design—The Subunit and Adjuvant Approach* (1995) Pharmaceutical Biotechnology, Volume 6 (eds. Powell, M. F., & Newman, M. J.) Plenum Press, New York and London, ISBN 0-306-44867-X). Exemplary adjuvants include complete Freund's adjuvant (CFA) that is not used in humans, incomplete Freund's adjuvant (IFA), squalene, squalane and alum (e.g., Alhydrogel™, Superfos, Denmark), which are materials well known in the art, and are available commercially from several sources. Other exemplary adjuvants include the adjuvants described in Lanar et al., U.S. Pat. No. 7,029,685, and U.S. Patent Publication No. 2006/0073171, herein incorporated by reference.

In some embodiments, the immunogenic composition is a vaccine composition. Vaccine preparation is generally described in New Trends and Developments in Vaccine (eds. Voller et al.), University Park Press, Baltimore, Md., U.S.A., 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of immunogen(s) present in each vaccine dose is selected as an amount that induces an immune response (such as an immunoprotective response) without significant, adverse side effects in typical vaccines. The term "immune response" refers to an acquired and enhanced degree of protective immunity against *Plasmodium* infection or malarial disease, for example, complete or partial protection against infection or disease following subsequent exposure to malaria parasites. The amount of immunogen present in each dose will vary depending upon which specific immunogens are employed, and other factors. Generally, it is expected that each dose will comprise a total of 1-1000 micrograms of protein, such as 1-200 micrograms or 10-100 micrograms or 5-50 micrograms. Following an initial vaccination, subjects will generally receive one or more boosts. An optimal amount for a particular vaccine, as well as the number and frequency of boosts, can be determined empirically by standard studies involving observation of immune responses in subjects.

The vaccine compositions of the invention may be administered by any suitable method of administration known in the art, including, but not limited to, intradermally, subcutaneously, intramuscularly, intraperitoneally, orally, ocularly (e.g., as an eye spray), and intravenously. Vaccines are conventionally administered parenterally, by injection, for example, either subcutaneously or intramuscularly. Additional formulations that are suitable for other modes of administration include suppositories and, in some cases, oral formulation or by nasal spray. For suppositories, traditional binders and carriers can include, for example, polyalkalene glycols or triglycerides. Oral formulations include such normally employed excipients as, for example, pharmaceutical grades of mannitol, lactose, starch, magnesium stearate, sodium saccharine, cellulose, magnesium carbonate and the like.

In some embodiments, the vaccine compositions of the invention are DNA vaccines comprising a nucleic acid molecule encoding one or more placental *P. falciparum* polypeptides of the invention. Thus, some embodiments provide an immunogenic composition comprising a nucleic acid molecule encoding a polypeptide and a pharmaceutically acceptable carrier, wherein the polypeptide comprises an amino acid sequence selected from the group consisting of SEQ ID NOs:1-4 and 6-24, and immunogenic derivatives thereof. Methods for preparing and administering a DNA vaccine expressing *Plasmodium* proteins are known in the art and have been previously described (see, e.g., Doolan & Hoffman (2001) *Int. J. Parasitol.* 31:753-62; Narum et al., U.S. Pat. No. 7,078,507, herein incorporated by reference. In some embodiments, the vaccine compositions of the invention are viral vaccines comprising a viral vector encoding one or more placental *P. falciparum* polypeptides of the invention. Exemplary viral vectors for use in the vaccine compositions of the invention include, but are not limited to, vaccinia viral vectors (such as vectors based on modified vaccinia virus or avian pox viruses), adenoviral vectors, and yellow fever viral vectors (see, e.g., Imoukhuede et al. (2006) *Vaccine*, in press; Miao et al. (2006) *Vaccine*, in press; Tao et al. (2005) *J. Exp. Med.* 201:201-9). Methods for preparing and administering viral vaccine expressing *Plasmodium* proteins are known in the art and have been previously described (see, e.g., Imoukhuede et al. (2006) *Vaccine*, in press; Miao et al. (2006) *Vaccine*, in press; Tao et al. (2005) *J. Exp. Med.* 201:201-9).

Another aspect of the invention provides methods for inducing an immune response against placental *P. falciparum* parasites, comprising administering an immunogenic composition comprising an effective amount of one or more placental *P. falciparum* polypeptides of the invention. Thus, in some embodiments the invention provides a method for inducing an immune response in a mammalian subject against *Plasmodium falciparum*, comprising administering to the host a composition comprising an effect amount of at least one isolated polypeptide selected from the group consisting of SEQ ID NOs:1-4 and 6-24, and immunogenic derivatives thereof. Exemplary mammalian subjects for the methods of inducing an immune response include, but are not limited to, humans, goats, rabbits, and mice. In some embodiments the mammalian subject is a human subject.

Another aspect of the invention provides methods for treating a subject in need thereof, comprising administering to a subject in need thereof an immunogenic composition comprising an effective amount of one or more placental *P. falciparum* polypeptides of the invention. Thus, in some embodiments the invention provides a method for treating a human subject in need thereof, comprising administering to a human subject an immunogenic composition comprising at least one isolated polypeptide selected from the group consisting of SEQ ID NOs:1-4 and 6-24, and immunogenic derivatives thereof.

The term "treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In some embodiments, the subjects to be treated are human subjects suffering from malaria, such as, for example, placental malaria. In some embodiments, the subjects to be treated are human subjects at risk for contracting malaria, including, but not limited to women at risk for contracting placental malaria. The subjects to be treated may or may not have previously been infected by *P. falciparum* parasites.

The term "effective amount" for a therapeutic or prophylactic treatment refers to an amount or dosage of a composition sufficient to induce a desired response (e.g., an immunogenic response) in the individual to which it is administered. Preferably, the effective amount is sufficient to effect treatment, as defined above. The effective amount and method of administration of a particular therapeutic or prophylactic treatment may vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosages for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the prevalence of *P. falciparum* in the geographical vicinity of the patient, the severity of the disease state of the patient, age, and weight of the patient, diet, time and frequency of administration, drug combination(s), reaction sensitivities, and tolerance/response to therapy. An appropriate effective amount can be readily determined using only routine experimentation. Several doses may be needed per individual in order to achieve a sufficient response to effect treatment. Suitable regimes for initial administration and follow-up administration (e.g., booster shots) are also variable, but are typified by an initial administration followed in intervals (weeks or months) by a subsequent administration.

The production of antibodies elicited by a treatment is readily ascertained by obtaining a plasma or serum sample from the subject to which an immunogenic composition is administered and assaying the antibodies therein for their ability to bind to the polypeptide(s) used to elicit the immune response to *P. falciparum* parasites, such as placental parasites. Exemplary methods include, but are not limited to, ELISA assays or by other immunoassays such as a Western blots, as is well known in the art. Another method for measuring the production of antibodies is by using an indirect immunofluorescence assay (IFA).

Antibodies to one or more of the placental *P. falciparum* parasites of the invention may be isolated from the blood of the host mammal using well known techniques, and then reconstituted into a second vaccine for passive immunization, as is also well known. Similar techniques are used for gammaglobulin immunizations of humans. For example, antiserum from one or a number of immunized hosts can be precipitated in aqueous ammonium sulfate (typically at 40-50 percent of saturation), and the precipitated antibodies purified chromatographically (e.g., affinity chromatography).

In another aspect, the invention provides diagnostic and screening agents and assays, which may be protein-based or nucleic acid-based. These agents and assays may be used to detect the presence of the placental *P. falciparum* polypeptides of the invention, or nucleic acid molecules encoding them, in order to determine whether a subject is suffering from or is likely to suffer from malaria, particularly pregnancy malaria. Many techniques may be used, including, but not limited to, ELISA, sandwich assays, immunoprecipation, immunoblots, hybridization techniques, and PCR.

In some embodiments, the placental *P. falciparum* polypeptides of the invention are used for the detection of antibodies in a subject. In some embodiments, antibodies to the placental *P. falciparum* polypeptides of the invention are used to detect the presence of these polypeptides. Diagnostic immunoassay procedures are standard in the art (see, e.g., *Basic and Clinical Immunology* (1991) 7th ed., Stites, D., & Terr, A.) Exemplary methods may, for example, use solid supports, or immunoprecipitation. Most assays involve the use of labeled antibody or polypeptide. Such labels may be, for example, enzymatic, fluorescent, chemiluminescent, radioactive, or dye molecules. Assays that amplify the signals from the immune complex are also known, such as assays that utilize biotin and avidin or streptavidin, and enzyme-labeled and mediated immunoassays, such as ELISA assays.

Some embodiments provide methods for the in vitro diagnosis of malaria in a subject likely to be infected by *P. falciparum*, comprising (a) contacting a biological sample comprising antibodies from a subject with one or more placental *P. falciparum* polypeptides of the invention under conditions enabling the formation of antigen/antibody complexes between the polypeptides and the antibodies, and (b) detecting the formation of antigen/antibody complexes. Examples of biological samples that may be used to perform this method are red blood cells, white blood cells, serum or urine. Conditions enabling the formation of antigen/antibody complexes are well known in the art.

The invention also provides methods for monitoring the immune status of a subject vaccinated against infection or disease caused by *P. falciparum*, comprising (a) contacting a biological sample comprising antibodies from a subject with one or more placental *P. falciparum* polypeptides of the invention under conditions enabling the formation of antigen/antibody complexes between the polypeptides and the antibodies, and (b) detecting the formation of antigen/antibody complexes.

In the diagnostic and monitoring methods described above, the biological sample may be further contacted with one or several antigenic peptides originating from other *Plasmodium* antigens.

In some embodiments, the diagnostic and screening agents and assays are nucleic acid-based. Exemplary diagnostic and screening agents for use in nucleic acid-based assays include nucleic acid probes complementary to nucleic acid molecules encoding *P. falciparum* polypeptides of the invention. Nucleic-acid based diagnostic and screening assays are well known in the art. Exemplary diagnostic and screening assays to be used in this aspect of the invention are described in Scherf et al., U.S. Pat. No. 6,855,323, herein incorporated by reference.

The invention also provides kits which are useful for carrying out the present invention. The kits may include a first container means containing the vaccine or antibodies of the invention. The kit may also include other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The following examples illustrate representative embodiments now contemplated for practicing the invention, but should not be construed to limit the invention.

Example 1

This Example describes proteomic studies to identify parasite proteins displayed on the surface of infected red blood cells (IRBCs).

Electron microscopy studies previously demonstrated that the "knob" structures on the surface of IRBC are the point of attachment of IRBC to the vascular endothelium. One of the characteristics of knob-associated proteins is that they are insoluble in non-ionic detergent and soluble in ionic detergent. Therefore, the following approach was used: enriching for knob-associated proteins by sequential extraction of parasites with non-ionic detergent followed by extraction with ionic detergent, and further separating peptide fragments of these proteins by gel electrophoresis or liquid chromatography, to be used in tandem mass spectrometry (MS/MS) studies.

Materials and Methods a. Sample preparation: Parasite samples were collected from pregnant women and their children recruited to the MOMS project in Muheza Tanzania. The study was performed on 18 samples collected from infected placenta and 21 isolates collected from infected children that attended MOMS clinic in Muheza. Peripheral blood from infected children contains parasites at the ring stage of development. The parasites were allowed to mature to the trophozoite-schizonts stages in culture for 12-20 hr as previously described (Trager & Jensen (1976) *Science* 193:673-5). Mature forms of the parasites were concentrated on percoll gradient. Enriched samples contained more than 90% infected red blood cells (IRBCs).

Enrichment for membrane proteins was performed by sequential extraction with detergent (Fried et al. (2004) *Proteomics* 4:1086-93). Parasite were incubated in lysis buffer A (10 mM Tris-HCl pH 7.4, 5 mM EDTA, 1% Triton X-100) for 30 min at 4° C., the lysate was centrifuge for 20 min at 12,000×g at 4° C. Supernatant containing soluble proteins was removed and lysis buffer B (10 mM Tris-HCl pH 7.4, 5 mM EDTA, 2% SDS, 6 M Urea) was added to the pellet containing insoluble proteins.

Trypsin digestion of protein mixture: Proteins were reduced with 10 mM DTT for 1 hr at 37° C. followed by alkylation with 20 mM iodoacetamide for 1 hr at 25° C. The sample was diluted to 0.05% SDS with 25 mM $NH_4CO_3$ and Trypsin was add to a final enzyme:substrate ratio of 1:50 (w:w) (Fried et al. (2004) *Proteomics* 4:1086-93). The samples were digested over night at 37° C. After trypsin digestion, peptides were cleaned using HILIC (The Nest Group Inc., Southboro, Mass.) according to the manufacturer's instructions.

b. LC-MS/MS analysis using ion trap: LC-MS/MS was performed using a LCQ Deca XP (ThermoFinnigan) ion trap mass spectrometer (ThermoFinnigan) or LTQ-MS (ThermoFinnigan, San Jose, Calif.). A total of 5 µg (1 µg/µL) of total peptide (as determined by BCA assay) were loaded onto the reversed phase column using a two mobile-phase solvent system consisting of 0.4% acetic acid in water (A) an 0.4% acetic acid in acetonitrile (B).

The mass spectrometer operated in a data-dependent MS/MS mode over a m/z range of 400-2000. For each cycle, the three most abundant ions from each MS scan were selected for MS/MS analysis using 45% collision energy. Dynamic exclusion was used to discriminate against previously analyzed ions in a one minute window.

c. Data analysis: The Sequest algorithm was used to match MS/MS spectra to peptides in the database (Eng et al. (1994) *Mass Spectrom.* 5:976-89). The database included *P. falciparum* 3D7 genome sequence and other *Plasmodium* sequences submitted to NCBI, as well as the sequences from the non-redundant human database. Spectra/peptide matches were retained according to the following criteria: a deltaCn value of 0.1 and for charge state +1, X corr≧1.5 for full tryptic peptides and Xcorr≧3.1 for partially cleaved peptides. For charge state +2, X corr≧1.9 for full tryptic peptides and Xcorr≧3.8 for partially cleaved peptides. For charge state +3, X corr≧2.9 for full tryptic peptides and Xcorr≧4.5 for partially cleaved peptides (Qian et al 2005. J Proteome Research 4:53-62).

d. Accurate mass and time tag (AMT) by Fourier transform ion cyclotron resonance (FTICR-MS): 5 µg of peptide mixtures were separated by HPLC using reversed-phase capillary column (150 µM i.d.×360 µm o.d. Polymico Technologies, Phoenix Ariz.) using a two mobile-phase solvent system consisting of 0.2% acetic acid and 0.05% trifluoroacetic acid (TFA) in water and 0.1% TFA in 90% acetonitrile/10% water. FTICR mass spectrometer was used for detection. Peptides identified in LC-MS/MS were used as potential mass and time tags (PMTs) were matched to peptides detected by MS-FTICR. The FTICR data was analyzed using software developed in-house.

Quantitative analysis was performed using Acuity software on normalized values (Cluster program). Statistical analysis for comparison between placental samples and children samples was performed using non-parametric method (Mann Whitney).

e. Quantitative RT-PCR: For quantitative PCR, total RNA was extracted from placenta parasites and mature forms parasite collected from infected children using RNAwiz (Ambion, CA). Reverse transcription was performed using oligodT$_{20}$ primer and Superscript II enzyme (Invitrogen, CA). Quantitative RT-PCR was performed using SYBR green master mix in an ABI Prism 7000 thermal cycler (Applied Biosystems). Primers were validated using both gDNA and a pool of cDNA. Threshold cycles (CT) were calculated and normalized ($\Delta\Delta$CT method) using CT values for *P. falciparum* housekeeping gene seryl-tRNA synthetase. The results are expressed as fold change from the control gene and statistical significance was determined using t-test.

Results

Protein profiles of placental parasites (i.e., parasites that bind to CSA) were compared with protein profiles of parasites from infected children (i.e., parasites that do not bind to CSA). This study identified peptides from several *P. falciparum* proteins with unknown functions and predicted transmembrane domains. These are believed to be novel proteins displayed on the IRBC surface. The list of unique proteins expressed in 2 or more placental isolates is shown in Table 1, except for PF13_0137 and PFL1200c for which peptides have been identified in one isolate by LC-MS/MS. Confirmation was obtained by FTICR-MS which is a more accurate and sensitive technology than LC-MS/MS (Smith et al. (2002) *Proteomics* 2:513-23).

TABLE 1

Surface proteins identified by proteomic studies

| Protein ID | SEQ ID NO | No. of isolates | No. of peptides | No. of Spectra | SP | TM | PEXEL |
|---|---|---|---|---|---|---|---|
| MAL7P1.115 | SEQ ID NO: 1 | 2 | 2 | 2 | n | y | n |
| PF08_0046 | SEQ ID NO: 2 | 4 | 4 | 4 | n | y | n |
| PF13_0137 | SEQ ID NO: 3 | 1 | 1 | 1 | n | y | n |
| PFA0180w | SEQ ID NO: 4 | 2 | 3 | 4 | y | y | n |
| PFA0745w | SEQ ID NO: 5 | 2 | 2 | 2 | y | y | y |
| PFC0580c | SEQ ID NO: 6 | 2 | 2 | 3 | y | y | n |
| PFD0690c | SEQ ID NO: 7 | 2 | 2 | 2 | y | y | n |
| PFI0805w | SEQ ID NO: 8 | 2 | 2 | 3 | n | y | n |
| PFI1785w | SEQ ID NO: 9 | 6 | 13 | 32 | n | y | y |
| PFL1200c | SEQ ID NO: 10 | 1 | 1 | 1 | n | n | n |

SP = Signal peptide
TM = Transmembrane domain
PEXEL = Plasmodium Export Element (Hiller et al. (2004) Science 306: 1934-7; Marti et al. (2004) Science 306: 1930-3)

Using quantitative analysis (quantitative proteomics and quantitative RT-PCR), 5 of these proteins were at significantly higher levels in placenta parasites compared to isolates collected from infected children, as shown in Table 2. Using a quantitative proteomics approach, an additional protein expressed specifically by placental parasites was identified (Protein ID PFB0280w in Table 2).

TABLE 2

Surface proteins upregulated according to quantitative proteomics and qRT-PCR

| Protein ID | SEQ ID NO | qRT-PCR fold change (p value) | qProteomics p value |
|---|---|---|---|
| PF13_0137 | SEQ ID NO: 3 | | 0.00003 |
| PFA0180w | SEQ ID NO: 4 | 3.8 (0.008) | |
| PFB0280w | SEQ ID NO: 11 | 7 (0.02) | 0.007395 |
| PFI0805w | SEQ ID NO: 8 | | 0.02 |
| PFI1785w | SEQ ID NO: 9 | 10 (<0.0001) | 0.01 |
| PFL1200c | SEQ ID NO: 10 | | 0.02 |

Example 2

This Example describes studies to show the immunogenicity of exemplary recombinant proteins identified by proteomic studies.

Materials and Methods a. Expression of PFB0280w (SEQ ID NO:11) and PF13_0137 (SEQ ID NO:3): Recombinant proteins were prepared by cloning the genes into an expression vector pET28b (Novagen) according to the manufacturer instructions. Proteins expression in prokaryotic vector pET28b was carried out by growing bacteria to the logarithmic phase of growth, inducing expression of the recombinant protein with 1 mM IPTG and continuing to grow the bacteria culture to saturation. The culture was spun down and bacteria cell pellets were washed 3 times in solution A (50 mM Tris, 10 mM EDTA, 5 mM DTT, 2% Triton X-100, 500 mM NaCl pH 7.5). Proteins were solubilized for 2 hours in solution B (6 M guandium-HCl, 50 mM Tris pH8.0, 5 mM DTT). Cell debris were removed by centrifugation, and protein solution is loaded onto Nickel column to purify the His-tagged recombinant protein according to the manufacturer's specification (Novagen).

b. Immune recognition studies: ELISA assays were used for the analysis of the immune recognition of the recombinant proteins by sera from immune and non-immune subjects according to the protocol in Antibodies: A Laboratory Manual (1988) Ed Harlow, David Lane Ed. 96-well ELISA plates (Immulon 3) were coated with recombinant protein diluted to a concentration of 10 µg/ml in carbonate/bicarbonate buffer pH 8.6. The plates were incubated over-night at 4° C. The plates were washed 3 times in PBS-Tween buffer. Remaining sites for protein binding on the ELISA plates were saturated by incubating with blocking buffer (2% BSA in PBS-Tween) for 2 hours at room temperature. Sera samples from immune women (multigravid), non-immune women (primigravid), and non-immune males were diluted 1:100 and added to the wells. The plates were incubated for 2 hours at room temperature, followed by washing 3 times with PBS-Tween buffer. Mouse anti-human IgG conjugated to HRP (enzyme labeled reagent) was added at dilution of 1:1000 and the plates were incubated for 1 hour at room temperature followed by 3 washes with PBS-Tween buffer. The detection was performed using peroxide substrate ABTS (Pierce) and the absorbance was measured in Elisa reader (Molecular Devices) at 405 nm.

Results

The recombinant proteins were analyzed for their recognition by sera from immune women (multigravidas) and non-immune women (primigravidas) as well as males residing in the same area. As shown in Table 3, sera from multigravidas had significantly higher levels of antibodies directed toward these proteins, similarly to the pattern of natural acquired immunity to placental parasites. It is expected that pregnancy malaria vaccine candidates will be better recognized by sera from multigravid women than primigravid women, indicating that these two properties of pregnancy malaria candidates.

TABLE 3

Immune recognition of surface proteins identified by proteomic studies

| | Male Sera (mean O.D.) | Primigravid Sera (mean O.D.) | Multigravid Sera (mean O.D.) | p-value |
|---|---|---|---|---|
| PF13_0137 SEQ ID NO: 3 | 0.148 | 0.189 | 0.212 | 0.005 |
| PFB0280w SEQ ID NO: 11 | 0.38 | 0.45 | 0.58 | 0.02 |

Example 3

This Example describes studies to show the immunogenicity of recombinant proteins derived from cell surface proteins identified by proteomic and/or microarray studies.

Materials and Methods a. Analyses of protein sequences: Large molecular weight proteins that cannot be expressed as full length proteins may be expressed as predicted immunogenic domains. Such immunogenic domains are predicted from the sequence of the proteins identified by proteomic studies in EXAMPLE 1, or the microarray studies in EXAMPLE 4, and used for animal immunization studies. Protein sequences were analyzed using the DNASTAR program by several algorithms, including prediction of hydrophilicity according to Kyte-Doolittle method, surface probability according to Emini method, and antigenicity according to Jameson-Wolf method (DNASTAR, Inc).

Protein PFB0280w (SEQ ID NO:11) is a predicted 302 kD protein. Analysis using DNASTAR program suggested that the region between amino acids 572-877 contains several hydrophilic and antigenic epitopes. A domain including amino acids 572-877 is expressed as further described below.

Using a similar approach, the first 500 amino acids of protein PF13_0137 (SEQ ID NO:3) is expressed as further described below.

PFA0180w (SEQ ID NO:4) contains a signal peptide sequence, the sequence downstream is predicted to be surface expressed and contain multiple antigenic epitopes. This protein is expressed as two domains; the first domain includes amino acids 50-750, the second domain includes amino acids 751-1471. Each of these domains is predicted to be about 7010, which is amenable to expression in both prokaryotic and eukaryotic expression systems.

PFI0805w (SEQ ID NO:8) is a large molecular weight protein of 304 kD. Based on protein analysis as described, two domains are expressed. The first domain contains amino acids 370-670, the second domain includes amino acids 2000-2500.

PFL1200c (SEQ ID NO:10) is a small molecular weight protein of 12 kD. The full length protein is expressed as described below.

b. Protein expression in *E. coli*: Protein expression in prokaryotic vector pET28b is carried out by growing bacteria to the logarithmic phase of growth, inducing expression of the recombinant protein with 1 mM IPTG and continuing to grow the bacteria culture to saturation. The culture is spun down and the bacteria cell pellet is washed 3 times in solution A (50 mM Tris, 10 mM EDTA, 5 mM DTT, 2% Triton X-100, 500 mM NaCl pH7.5). Proteins are solubilized for 2 hours in solution B (6 M guandium-HCl, 50 mM Tris pH8.0, 5 mM DTT). Cell debris are removed by centrifugation, and the protein solution is loaded onto Nickel columns to purify the His-tagged recombinant protein according to the manufacturer's specification (Novagen).

c. In vitro protein expression: Because some of the malaria antigens may be difficult to express in cellular systems and are conformation dependent, an alternative method is also used to express the proteins identified in EXAMPLES 1 and 4, by using a cell-free in-vitro protein synthesis system (ENDEXT Technology) produced by CellFree Sciences. This method utilizes wheat germ lysate free of translation inhibitors, that allows stable translation of eukaryotic proteins, including conformation-dependent malaria antigens. The genes encoding these proteins are cloned into pEU-E01-His-TEV-MCS vector (Cell Free Systems, Inc.), followed by protein synthesis according to the manufacturer (CellFree Sciences). The His-tag proteins are purified using anti-His beads according to the manufacturer (Dynal).

d. Immune recognition of proteins: The recombinant proteins are analyzed for their recognition by sera from immune women (multigravidas) and non-immune women (primigravidas) as well as male residing in the same area, as described in EXAMPLE 2.

It is expected that the proteins that are used to immunize rabbits are immunogenic, and elicit antibodies that recognized the surface of the IRBC. Proteins that elicit antibodies that bind specifically only to CSA-binding parasites and not to other parasites are likely to be unique surface proteins of placental parasites.

Proteins that react with sera from multigravidas at significantly higher levels compared to sera from primigrivadas and males are expected to be good immunogens for use in a pregnancy malaria vaccine.

Example 4

This Example describes microarray studies to identify genes that are upregulated in placental parasites and that encode proteins predicted to be surface antigens.

Materials and Methods

Two-color spotted microarrays were used for all experiments. The microarrays were prepared using 70 mer oligonucleotides spotted onto gamma amino propyl silane coated glass slides. The 70 mers were obtained from Operon and consist of the complete set of commercially available *P. falciparum* probes. In addition, 70 mers from predicted open reading frames that were not represented in the commercially available probe set as well as probes for PfEMP1 genes sequenced from field isolates of *P. falciparum*, were designed by the Duffy lab and synthesized by Illumina. A total of 8596 70 mers were spotted twice on each slide using Gene Machine OGR-04 Omnigrid oligonucleotide arrayer.

Microarray analysis was performed using RNA prepared from parasites isolated from clinical specimens collected from Muheza Designated District Hospital in Muheza, Tanzania. RNA was prepared from both peripheral blood parasites and placental parasites collected from women with pregnancy malaria. Peripheral blood from children with malaria was collected for comparison of gene expression profiles to identify genes that are up-regulated in parasites causing pregnancy malaria. RNA quality was evaluated by Bioanalyzer (Agilent Technologies). RNA from each sample was amplified to generate antisense RNA using the Message Amp II kit (Ambion). Amplified RNA product was quantified and its quality further assessed using the Bioanalyzer. Antisense RNA was then cross-linked to CY3 and CY5 monoesters to generate fluorescent probes. The specific activity of each probe was measured. 5 µg of labeled probe RNA from samples to be compared were combined. The combined probes were fragmented at 70° C. using RNA fragmentation reagent (Ambion) to approximately 100 bp. Competitive hybridization using probe RNA derived from pregnant women and RNA from children's parasites was performed. In practice, when maternal parasite RNA was labeled with CY3 the children's RNA was labeled with CY5. Dye swaps were conducted to minimize dye bias and to provide replicate hybridizations. Microarrays were hybridized for 16-20 hours at 63° C. Following hybridization, the slides were washed to remove unincorporated probe and scanned at 532 nm and 634 nm using the Gene Pix 400A scanner (Axon).

Hybridization of fluorescent probes to each oligonucleotide spot was quantified using Gene Pix Pro Software (Axon). After performing Loess normalization, differential expression was assess by quantifying Log 2 CY5/CY3 ratios using single sample, and Student's t-test as well as ANOVA statistical packages on Acuity 4.0 microarray data analysis software (Axon).

Quantitative RT-PCR was performed as described in EXAMPLE 1.

Results

Comparing the transcriptional profiles of placental parasites, peripheral parasites from pregnant women and children with malaria identified potential genes involved in binding placental tissue, as shown in Table 4. Up-regulated genes were examined for potential transmembrane domains, signal sequence and PEXEL (*Plasmodium* export element) sequences (Hiller et al. (2004) *Science* 306:1934-7; Marti et al. (2004) *Science* 306:1930-3) that could be used to indicate that these genes encode proteins at the red blood cell surface that are involved directly in parasite adhesion to placental tissue or are potentially immunogenic. The genes described in Table 4 are designated by their PlasmoDB gene identification names. The fold change in expression, and the presence of transmembrane domains and PEXEL sequences are also indicated in Table 4.

TABLE 4

Placental upregulated genes identified by microarray studies

| Gene ID | SEQ ID NO | q-RT_PCR fold change (p value) | TM | PEXEL |
|---|---|---|---|---|
| PFB0115w | SEQ ID NO: 12 | 9-14 (0.0004) | y | n |
| PFD1140w | SEQ ID NO: 13 | 13-15 (0.0005) | y | y |
| PFI1785w | SEQ ID NO: 9 | 10-37 (0.003) | y | y |
| MAL13P1.470 | SEQ ID NO: 14 | 36 (0.007) | y | y |
| MAL13P1.320 | SEQ ID NO: 15 | | y | n |
| MAL7P1.171 | SEQ ID NO: 16 | | y | y |
| MAL7P1.144 | SEQ ID NO: 17 | | y | n |
| MAL7P1.225 | SEQ ID NO: 18 | 26-39 (0.058) | n | y |
| PFD0090c | SEQ ID NO: 19 | 5-6 (0.0088) | y | y |
| PF10_0013 | SEQ ID NO: 20 | 5 (0.01) | y | n |
| MAL6P1.93 | SEQ ID NO: 21 | | y | n |
| MAL8P1.2 | SEQ ID NO: 22 | | y | n |
| PFA0700c | SEQ ID NO: 23 | | y | y |
| PFL0050c | SEQ ID NO: 24 | 11-12 (0.001) | n | n |

TM = Transmembrane domain

PEXEL = Plasmodium Export Element (Hiller et al. (2004) Science 306: 1934-7; Marti et al. (2004) Science 306: 1930-3)

Example 5

This Example describes studies to show the immunogenicity of an exemplary recombinant protein identified by microarray studies.

Materials and Methods

Amino acids 34 to 347 of PFD1140w (SEQ ID NO:13) were expressed by in vitro translation, as described in EXAMPLE 3. Immune recognition studies were performed as described as described in EXAMPLE 2.

Results

The recombinant protein was analyzed for its recognition by sera from immune women (multigravidas) and males residing in the same area. As shown in Table 5, sera from multigravidas had significantly higher levels of antibodies directed toward these proteins, similarly to the pattern of natural acquired immunity to placental parasites.

TABLE 5

Immune recognition of surface proteins identified by microarray studies

| | Male Sera, N = 8 (arbitrary units) | Multigravid Sera, N = 10 (arbitrary units) | p-value |
|---|---|---|---|
| PFD1140 SEQ ID NO: 13 | 14.4 | 19.2 | 0.145 |

Each of the scientific or patent references cited herein is hereby incorporated by reference.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for inducing an immune response against placental *Plasmodium falciparum* parasites in a mammalian subject, comprising administering to a mammalian subject an amount of an immunogenic composition effective to induce an immune response against placental *Plasmodium falciparum* parasites in the mammalian subject, wherein the immunogenic composition comprises an isolated polypeptide with at least 95% amino acid sequence identity to the amino acid sequence of SEQ ID NO:9.

2. The method of claim 1, wherein the isolated polypeptide comprises the amino acid sequence of SEQ ID NO:9.

3. The method of claim 1, wherein the immunogenic composition further comprises an adjuvant.

* * * * *

SEQUENCE LISTING

<160> NUMBER OF SEQ ID NOS: 24

<210> SEQ ID NO 1
<211> LENGTH: 780
<212> TYPE: PRT
<213> ORGANISM: Plasmodium falciparum

<400> SEQUENCE: 1

```
Met Thr Lys Asn Asp Tyr Arg Ser Ile Pro Lys Phe Met Lys Met Ile
 1               5                  10                  15

His Lys Val Lys Thr Asn Tyr Met Ser Ile His Ile Ile His Leu Ile
            20                  25                  30

Met Asn Ile Ile Val Leu Asn Tyr Ile Val Ile Tyr Ile Phe Phe Leu
        35                  40                  45

Asn Lys Tyr Asn Asn Asp Ser Lys Arg Asn Ile Leu Asp Glu Asp Gln
    50                  55                  60

Asn Tyr Tyr Phe His Val Glu Gly Asn Lys Ile Glu Glu Arg Leu Arg
65                  70                  75                  80

Tyr Thr Leu Ile Ile Ile Tyr Ile Phe Phe Cys Leu Thr Leu His Val
                85                  90                  95

Phe Ile Cys Ile Thr Gln Tyr Tyr Asn Asn Asn Lys Gly Leu Cys Lys
            100                 105                 110

Asn Leu Ser Asn Lys Asp Asn Val Asn His Val Tyr Cys Glu Asn Lys
        115                 120                 125

Ile Asn Lys Glu Asn Lys Asn Lys Glu Asn Cys Lys Leu Tyr Glu Asn
    130                 135                 140

Lys Asn Thr Leu Gly Asn Lys Arg Lys Asn Gly Tyr Met Asn Lys Asn
145                 150                 155                 160

Tyr Lys Gln Leu Lys Asp Lys Lys Arg Asn Glu Asp Ile Tyr Ile Ser
                165                 170                 175

Ile Asn Tyr Ile Phe Leu Tyr Ile Leu Leu Ala Leu Ile Gly Leu Ser
            180                 185                 190

Asn Tyr His Ile Lys Glu Phe Phe Tyr Phe Tyr Cys Ile Leu Ile
        195                 200                 205

Ile Cys Glu Ile Asn Thr Pro Ile Ile Phe Met Asn Leu Ile Lys
    210                 215                 220

Ile Ile Asn Lys Tyr Tyr Lys Lys Tyr Leu Phe Lys Asp Tyr Asn
225                 230                 235                 240

Ser Ile Asn Asn Ile Lys Lys Asn Asp Leu Tyr Ile Phe Phe Cys Tyr
                245                 250                 255

Phe Val Leu Leu Arg Tyr Leu Lys Lys Phe His Ile Tyr Gln Lys Phe
            260                 265                 270

Lys Ile Ser Gln Ser Glu Lys Lys Lys Asn Val Ile Ser Thr Tyr
    275                 280                 285

Tyr Glu Lys Glu Lys Lys Ile Gly Gly Leu Phe Cys Leu Phe Asn Tyr
        290                 295                 300

Ile Lys Asn Lys Asn Ile Thr Tyr Tyr Tyr Thr Tyr Val Tyr Lys Asn
305                 310                 315                 320

Thr Ile His Leu Phe Leu Lys Lys Lys Gln Ile Asn Lys Phe Cys Glu
                325                 330                 335

Ile Ile Tyr Ser Phe Phe Ile Lys Asn Gly Gly Ile Ile Tyr Ser Arg
            340                 345                 350

Ile Arg Thr Leu Leu Thr His Val Leu Ile Ile Leu Arg His Lys Ile
        355                 360                 365
```

```
Val Asp Glu Lys Ser Thr Asn His Tyr Asn Lys Lys Ile Tyr Ile Thr
    370                 375                 380

His Asp Ile Ser Glu Ile Glu Asn Thr Asn Lys Thr Ile Thr Asn Asn
385                 390                 395                 400

Val Gly Lys Glu Ile Lys Lys Glu Gln Glu Asn Asp Lys Tyr Tyr
                405                 410                 415

Tyr Asn Asn Cys Leu Thr Lys Lys Asn Ile Cys Asn Asp Ile His Thr
            420                 425                 430

Tyr Ser Asn Ile Phe Thr Leu Glu Gly Lys Lys Lys Asp Ser His
        435                 440                 445

Lys Glu Asn Tyr Asn Asn Glu Ile Ile Thr Gln Lys Glu Tyr Asn Lys
    450                 455                 460

Ile Arg Lys Asn Phe Tyr Lys Tyr Lys Asn Tyr Tyr Glu Tyr Phe Lys
465                 470                 475                 480

Lys Tyr Lys Asp Asp Asp Thr Cys Asp Asn Leu Ser Leu Tyr Glu Asn
                485                 490                 495

Glu Ile Leu Asp Lys Asn Asn Phe Tyr Phe Leu Ser Lys Lys Lys Lys
            500                 505                 510

Lys Glu Phe Gln Val Ile Glu Gln Gly Glu Asn Lys Leu Phe Phe Asn
    515                 520                 525

Asn Lys Lys Thr Asn Gly Gln Asp Asn Asn Ile Tyr Glu Met Glu Glu
530                 535                 540

Glu Ile Lys Asn Thr Asn Arg Tyr Ile His Ser Asn Asn Ile Asn Ile
545                 550                 555                 560

Asn Lys Ile Ser Thr Asp Thr Ser Leu Tyr Cys Pro Ser Ser Ser Thr
                565                 570                 575

Glu Gln Ile Asn Lys Ser Gln Tyr His Lys Thr Asn Asp Asp Lys Asn
            580                 585                 590

Asp Lys Ser Phe Leu Ser Tyr Glu Lys Glu Gly Pro Ile Gln Cys Arg
        595                 600                 605

Lys Lys Ile Asn Val Ile Lys Lys Lys Ile Lys Ile Tyr Tyr Lys
    610                 615                 620

His Tyr His His Val Glu Asp Ile Asn Lys Lys Val Ile Ile Ile Asn
625                 630                 635                 640

Asn Asn Asn Asn Asn Asn Ile Asn Asn Asn Asn Asn Ile Asn Asn
                645                 650                 655

Asn Asn Asn Asn Asn Asn Asn Asn Asn Asn Asn Asn Asn Asn
            660                 665                 670

Asn Asn Asn Asn Asn Asn Asn Asn Asn Asn Asn Asn Phe Ile Cys
        675                 680                 685

Leu Glu Asn Asn Val Lys Met Phe Leu Ser Asn Phe Lys Arg Lys Met
    690                 695                 700

Glu Ile Tyr Lys Phe Leu Gln Met Val Tyr Lys Val Leu Leu Leu Leu
705                 710                 715                 720

Asn Ile Tyr Leu Ile Phe Ser Ile Lys Gly Ile Leu Ile Tyr Met Asn
                725                 730                 735

Ile Tyr Tyr Phe Ile Phe Gln Asn Thr His Ser Leu Phe Ser Phe His
            740                 745                 750

Lys Cys Phe Leu Ile Leu Leu Gln Cys Cys Tyr Phe Cys Phe Ser Arg
        755                 760                 765

Leu Tyr Val Tyr Glu Tyr Arg Lys Leu Lys Lys Trp
    770                 775                 780
```

```
<210> SEQ ID NO 2
<211> LENGTH: 499
<212> TYPE: PRT
<213> ORGANISM: Plasmodium falciparum

<400> SEQUENCE: 2

Met Arg Arg Phe Ser Thr Cys Ser Thr Phe Tyr Arg Ser Lys Leu Ile
1               5                   10                  15

Tyr Asn Ile Arg Ser Tyr Asp Ile Asn Lys Lys Ser Tyr Cys Ser Ser
            20                  25                  30

Arg Glu Gly Ile Glu Glu Leu Glu Arg Val Ile Leu Asn Tyr His Lys
        35                  40                  45

Lys Glu Glu Ser Asn Phe Leu Gly Arg Lys Lys Tyr Glu Asn Phe
    50                  55                  60

Ile Arg Gln Val Leu Lys Asp Arg Cys Asp Asp Phe Lys Thr Asp Lys
65                  70                  75                  80

Ile Phe Leu Ser Ser Leu Glu Asp Ile Asp Glu Thr Phe Leu Ile Asn
                85                  90                  95

Asn Lys Asp Met Glu Ser Ile Lys Asp Tyr Val Glu Lys Arg Asn Lys
            100                 105                 110

Asp Asp Ile Ile Phe Lys Asp Lys Asn Lys Leu Tyr Glu Tyr Ile Glu
        115                 120                 125

Lys Ile Asn Ile Lys Ser Glu Ile Met Lys Ile Ala Met Cys Gly
130                 135                 140

Ile Arg Ile Ser Leu Asn Ile Leu Ile Phe Tyr Met Tyr Asp Ile Ile
145                 150                 155                 160

Leu Lys Leu Ile Lys Cys Leu His Tyr Tyr Asp Lys Asp Ile Ile Lys
                165                 170                 175

Tyr Asp Ser Ile Lys Asp Lys Asp Lys Tyr Tyr Lys Ile Gly Gln Tyr
            180                 185                 190

Tyr Tyr Tyr Tyr Tyr Tyr Asn Gln Asp Asn Asn Asn Val Asp Asp Asn
        195                 200                 205

Lys Asn Gly Lys Asp Lys Lys Glu Lys Ser Gly Pro Phe Leu Phe Leu
210                 215                 220

Lys Leu Tyr Lys Ile Leu Ser Asn Ile Leu Tyr Thr Thr Cys Glu Asn
225                 230                 235                 240

Ser Met Gln Thr Tyr Asn Lys Lys Tyr Ile Tyr Phe Lys Glu Glu Ile
                245                 250                 255

Ile Asn Lys Tyr Asn Ser Ile Asp Asp Ile Ile Tyr Lys Val Pro Ala
            260                 265                 270

Phe Leu Asn Ile Ser Phe Leu Phe Tyr Tyr Ile Asn Ile Cys Leu Tyr
        275                 280                 285

Ile Asp Pro Ser Arg Lys Ser Lys Asn Met Cys Leu Gln Asn Leu Asn
290                 295                 300

Asn Tyr Leu Asn Cys Ile Ala Asp Asp Glu Ile Asn Ile Ser Arg Glu
305                 310                 315                 320

Asp Phe Asn Tyr Leu Val Leu Ser Met Arg Leu Tyr Phe Leu Phe Phe
                325                 330                 335

Ser Tyr Asn Asp Ile Leu Asn Ile Leu Asn Glu Gly Ser Lys His Phe
            340                 345                 350

Leu Ser Thr Leu Val Leu Ile Pro Asn Asn Asn Asp Asn Lys Asn
        355                 360                 365

Asn Ile His Ser Ile Gln Met Asp Asp Asn Ile Asn Tyr Val Tyr Ile
370                 375                 380

Ile Asn Tyr Leu Asn Lys Asn Gln Lys Tyr Ile Glu Asn Thr Lys Ile
```

```
                385                 390                 395                 400
Thr Leu Phe Pro Phe His Phe Tyr Leu Ser Ser Leu Lys Asn Lys Ile
            405                 410                 415

Ile Tyr Ile Leu Glu Lys Asn Asp His Phe Tyr Leu Asn Asp Ser Asn
            420                 425                 430

Val Leu Arg Ser Tyr Asn Phe Trp Ser Tyr Phe Ile Ala Gln Lys Glu
            435                 440                 445

Asn Phe Lys Leu Leu Ser Leu Cys Thr Arg Asn Glu Tyr Ala Asp Leu
            450                 455                 460

Phe Asn Asp Gln Thr Arg Asp Ser Val Leu Ser Lys Tyr Val Asn Lys
465                 470                 475                 480

Asp Tyr Leu Tyr Asp Phe Asn Gln Arg Met Glu Tyr Lys Val Glu Gln
                485                 490                 495

Thr Asn Ile

<210> SEQ ID NO 3
<211> LENGTH: 1459
<212> TYPE: PRT
<213> ORGANISM: Plasmodium falciparum

<400> SEQUENCE: 3

Met Asp Asn Phe Met Val Arg Ile Lys Ala Asn Asn Glu Glu Val Asn
1               5                   10                  15

Asp Phe Ile Lys His Leu Phe Thr Glu Thr Phe Cys Asn Lys Asp Phe
                20                  25                  30

Ala Asp Asn Ile Lys Leu Asp Ala Gln Lys Thr Asn Glu Lys Gln Glu
            35                  40                  45

Ser Glu Lys Lys Asn Arg Tyr Ile Ile Thr Glu Lys Tyr Val Asp Asn
50                  55                  60

Tyr Met Ile Pro Tyr Leu Ile Arg Asn Asn Glu Ser Arg Glu Glu Lys
65                  70                  75                  80

Arg Asn Glu Asn Met Asn Ser Tyr Asp Glu Asp Asn Asn Tyr Tyr
                85                  90                  95

Tyr Asn Asp Ser Tyr Asn Tyr Asp Ile Phe Lys Tyr Ile Ser Cys Asp
                100                 105                 110

Ile Asn Ile Arg Asp Lys Asn Ser Val Ser Ser Glu Tyr Arg Asn Asn
            115                 120                 125

Ile Glu Asp Asp Thr Tyr Lys Asn Arg Ile Gln Phe Lys Leu Tyr Ala
130                 135                 140

Ser Glu Ile Tyr Phe Lys Asn Met Ile Lys Glu Lys Tyr Lys Ile Lys
145                 150                 155                 160

Tyr Asn Lys Tyr Asn Lys Lys Tyr Ile Glu Tyr Asn Ile Lys Asp Lys
                165                 170                 175

Ser Val Leu Leu Ile Tyr Gly Asp Trp Tyr Met Cys Asp Ser Phe Met
            180                 185                 190

Lys Asn Glu Lys Ser Asn Ile Thr Ile Lys Glu Leu Tyr Asp Tyr Ile
        195                 200                 205

Glu Glu Asn Ile Glu Asn Ile Asn Glu Ile Phe Asn Cys Leu Lys Gly
210                 215                 220

Ser Phe Ile Leu Phe Tyr Ile His Tyr Asp Ile Thr Asn Ile Asn Val
225                 230                 235                 240

Tyr Phe Phe Asn Asp Lys Phe Gly Met Lys Ser Phe Ile Tyr Phe Tyr
                245                 250                 255

Glu Glu Lys Ser Ile Ile Leu Thr Asn Met Tyr Gly Pro Phe Leu Asn
            260                 265                 270
```

```
Tyr Asn Tyr Asn Tyr Arg Glu Leu Asn Lys Asn Glu Phe Ile Phe Asn
            275                 280                 285

Asp Met Ser Val Lys His Glu Ile Asn Leu Ile Pro Thr Tyr Asp Thr
        290                 295                 300

Phe Val Gln His Asp Ile Lys Asn Asn Phe Leu Val Asp Lys Lys
305                 310                 315                 320

Lys Asn Cys Asp Tyr Asn Ile Ile Asn Lys Phe Asn Asn Ile Asp
                325                 330                 335

Asn Lys Glu Lys His Asp Asp Gln Cys Ser Lys Thr Ile Asn Glu
            340                 345                 350

Glu Ile Ala Ile Asn Ile Met Pro His Tyr Ile Tyr Lys Leu Ile Leu
            355                 360                 365

Leu Lys Asp Asn Gln Lys Asp Lys Asp Lys Asn Lys Asp Lys
370                 375                 380

Asn Lys Asp Thr Asn Thr Lys Thr Asn Ala Asn Thr Lys Thr Lys Thr
385                 390                 395                 400

Asn Asn Asn Asn His Arg Gln Glu Asp Asn Ile Phe Asn Ile His Asn
            405                 410                 415

His Ile Met Leu Lys Lys Ile Asn Lys Gln Tyr Cys Ile Tyr Asp Asn
            420                 425                 430

Ser Tyr Tyr Gln Trp Lys His Pro Val Val Asn Lys Phe Asn Ile Leu
        435                 440                 445

Asn Phe Gln Asp Ile Leu His Tyr Phe Glu Lys Thr Asn Ile Phe Lys
450                 455                 460

Asn Phe Lys Lys Gln Gln Lys Ile Gln Phe Leu His Thr Ile Asn Lys
465                 470                 475                 480

Ile Ile Gln Glu Lys Asn Ile Thr Val Cys Gln Asn Asn Tyr Leu Tyr
                485                 490                 495

Asn Thr Asn Lys Asn Asn Ile Pro Tyr Thr Lys Leu Asn Asn Val Phe
            500                 505                 510

Ile Asn Leu Phe Ile Ile Leu Leu Asn His Ile Ile Arg Gln Lys Ile
            515                 520                 525

Lys Arg Phe Phe His Leu Thr Cys Ser Gly Lys Lys Glu Glu Lys Lys
            530                 535                 540

Lys Asn Asp Asp Glu Lys Lys Asn Asp Asp Glu Lys Lys Asn Asp Asp
545                 550                 555                 560

Glu Lys Lys Asn Met Asp Gly Lys Lys Lys His Ile Asp Asp Glu Asn
                565                 570                 575

Lys Asn Asp Asn Met Asn Ile Pro Tyr Tyr Val Tyr Lys Glu Lys Lys
            580                 585                 590

Glu Lys Cys Ile Gly Ile Phe Ser Gly Gly Ile Asp Ser Thr Leu
            595                 600                 605

Leu Thr Ile Leu Thr Ile Lys Asn Phe Phe His Phe Tyr Gln Asp Gly
            610                 615                 620

Tyr Ile Glu Leu Val Asn Val Phe Asn Ile Asn Ala Ile Asp Arg
625                 630                 635                 640

Tyr Thr Cys Phe Val Ser Tyr Glu Lys Ile Ile Arg Met Phe Pro Asn
                645                 650                 655

Tyr Asp Ile Arg Leu Ile Leu Val Asp Val Tyr Pro Asp Asp Leu Ile
            660                 665                 670

Lys Tyr Glu Lys Ile Ile Tyr Ser Ile Ile Ser Pro Asn Asn Lys Ile
            675                 680                 685

Met Asp Phe Asn Ile Ser Ser Ala Leu Phe Phe Ala Asn Leu Gly Arg
```

```
              690                 695                 700
Gly Phe Leu Cys Pro Arg Thr Phe Phe Glu Ser Gln Glu Trp Arg Asn
705                 710                 715                 720

Ile Lys Glu Glu Asn Ile Met Asn Val Leu Asn Val Ser Asn Ile Cys
                725                 730                 735

Thr Ser Asn Gln His Thr Ser Asp Asn Asn Leu Trp Glu Glu Asn Ser
                740                 745                 750

Leu Glu Lys Lys Ile Cys Val Lys Gly Lys Arg Lys Lys Glu Ile Thr
                755                 760                 765

Ser Ser Ser Asn Ile Asn Ile Leu Tyr Lys Cys Arg Ile Cys Lys Tyr
770                 775                 780

Val Met Asn Lys Lys Cys Val His Lys Cys Cys Ser Val Cys Cys Lys
785                 790                 795                 800

Lys Leu Arg Tyr Ile Cys Ile Asn Glu Asn Val Tyr Asn Ile Asn Lys
                805                 810                 815

Glu Ile Asn Ser Lys Gly Cys Asp Asn Ala Asp Asn Asp Asp Asp Asn
                820                 825                 830

Asn Asp Asp Asn Asn Asp Gly Asp Asn Asn Asp Asp Asp Asn Asn
835                 840                 845

Asn Asp Asp Asn Asn Ile Asp Asp Asn Asp Gly Asp Asn Asn Asn Asp
850                 855                 860

Glu Lys Asp Phe Ile Gly Met Tyr Glu Ile Gln Tyr Asn Lys Glu Asn
865                 870                 875                 880

Lys Asn Lys Asn Lys Lys Asn Ile Tyr Leu Ile Val Lys Lys Glu Arg
                885                 890                 895

Ile Leu Ile Asn Phe Glu Leu Phe Arg Gln Cys Ile Ile His Lys Asp
                900                 905                 910

Lys Leu Tyr Asp Tyr Lys Lys Ile Gly Tyr Leu Phe Ala Glu Phe Lys
                915                 920                 925

Lys Glu Leu Lys Lys Asp Lys Met Asn Lys Lys Gln Glu Tyr Lys Glu
930                 935                 940

Asn Lys Tyr His Gly Glu Ile Ile Lys Asn Asp Lys His Pro Leu Cys
945                 950                 955                 960

Asp Glu Glu Tyr Lys Lys Asn Lys Tyr His Glu Glu Ile Ile Lys Asn
                965                 970                 975

Asp Lys His Pro Leu Cys Asp Glu Glu Tyr Lys Lys Asn Asn Tyr His
                980                 985                 990

Gly Glu Ile Ile Lys Asn Asp Lys His Pro Leu Cys Asp Glu Glu Tyr
                995                 1000                1005

Lys Lys Asn Lys Tyr His Glu Glu Ile Ile Lys Asn Asn Lys Leu
    1010                1015                1020

Pro Leu Cys Asp Glu Glu Tyr Lys Lys Asn Lys Tyr His Glu Glu
    1025                1030                1035

Ile Ile Lys Asn Asn Lys Leu Pro Leu Cys Asp Glu Glu Tyr Lys
    1040                1045                1050

Lys Asn Lys Tyr His Glu Glu Ile Ile Lys Asn Asn Lys Leu Pro
    1055                1060                1065

Leu Cys Asp Glu Glu Tyr Lys Lys Asn Lys Tyr His Glu Glu Ile
    1070                1075                1080

Ile Lys Asn Asn Lys Leu Pro Leu Cys Asp Glu Glu Tyr Lys Lys
    1085                1090                1095

Asn Lys Tyr His Glu Glu Ile Ile Lys Asn Asn Lys His Pro Leu
    1100                1105                1110
```

```
Cys Asp Glu Glu Tyr Ile Gln Arg Asp Phe Ile His Gln Phe Ala
    1115                1120                1125
Ser Glu Lys Ser Glu Ile Asn Glu Lys His Asn Leu Glu Lys Ile
    1130                1135                1140
Lys Asn Leu Phe Ser Ser Lys Gly Lys Asn Lys Lys Glu Gly Lys
    1145                1150                1155
Lys Asn Asn Lys Asn Lys Met Phe Ile Asn Asn Asp Asn Ile Asn
    1160                1165                1170
Asp Asp Ser Asn Glu Asp Gly Asp Glu Arg Gln Lys Lys Glu Lys
    1175                1180                1185
Thr Lys Ser Thr Tyr Asn Asp Thr His Leu Asn Tyr Phe Asn Lys
    1190                1195                1200
Asn Ile Tyr Tyr Pro Asn Asn Asn Tyr Asp Asn Glu Lys Glu Lys
    1205                1210                1215
Ser Phe Tyr Met Cys Asn His Gln Leu Leu Ile Ile Gly Ser Gly
    1220                1225                1230
Ala Asp Glu Leu Phe Gly Gly Tyr Tyr Arg Gln Asn Asn Phe Asn
    1235                1240                1245
Lys Lys Leu Ala Lys Ile Asn Lys Asn Tyr Lys Met Cys Glu Met
    1250                1255                1260
Ile Lys Asp Ile Arg Arg Ile Trp Ile Arg Asn Leu Tyr Arg Asp
    1265                1270                1275
Asp Arg Val Ile Thr Phe Ser Ser Phe Lys Lys Tyr Ile Phe
    1280                1285                1290
Tyr Pro Tyr Leu Asp Met Leu Met Ile Asn Phe Leu Phe Ser Leu
    1295                1300                1305
Pro Phe Cys Ile Ile Glu Thr Pro Met Gly Tyr Ile Asn Thr Asn
    1310                1315                1320
Glu Gly Asn Ile Asn Lys Cys His Lys Asn Glu Asn Leu Asn Asn
    1325                1330                1335
Asp Asp Glu Glu Met Glu Glu Pro Tyr Asn Thr Phe Asn Thr Glu
    1340                1345                1350
Tyr Met Asn Glu His Thr Leu Ile Tyr Glu Glu Gln Phe Asn Tyr
    1355                1360                1365
Leu Asn Thr His Ile Leu Asn Glu Cys Asn Tyr Ile Tyr Glu Arg
    1370                1375                1380
Met Lys Thr Glu Lys Ile Asn Lys Trp Ile Leu Arg Met Ser Met
    1385                1390                1395
Tyr Phe Leu Asn Phe Lys Asp Val Met Phe Phe Lys Lys Lys Ala
    1400                1405                1410
Ile Gln Phe Gly Ser Lys Ser Lys Asn Val Lys Arg Tyr Met Lys
    1415                1420                1425
Glu Ser Leu Gly Ile Tyr Pro Lys Asp Ser Glu Gln Asn Ser Ser
    1430                1435                1440
Ala Leu Phe Asn Glu Lys Ser Gly Arg Asp Glu Tyr Ile Leu Leu
    1445                1450                1455
Ser

<210> SEQ ID NO 4
<211> LENGTH: 1472
<212> TYPE: PRT
<213> ORGANISM: Plasmodium falciparum

<400> SEQUENCE: 4

Met Tyr Val Ser Phe Phe Ser Leu Ile Phe Cys Phe Tyr Val Ser Phe
```

-continued

```
  1               5                  10                 15
Tyr Ile Leu Phe Ile Thr Leu Phe Thr Lys Lys Asn Cys Leu Cys Ile
                 20                 25                 30

Val Leu Lys Glu Arg Glu Ser Tyr Asn Ile Ile Leu Lys Lys Lys
        35                 40                 45

Asn Lys Thr Lys Gln Asn Lys Thr Lys Tyr Phe Val His Asn Phe Phe
        50                 55                 60

Lys Lys Asn Asn Val His Pro Tyr Tyr Lys Ser Ile Arg Ile Phe Pro
65              70                 75                 80

Gly Arg Thr Phe Leu Pro Tyr Tyr Gln Asn Val Lys Asp Lys Lys
                85                 90                 95

Arg Asn Ile Lys Leu Lys Asp Asn Asn Asn Asn Asn Asn Asn Lys
        100                105                110

Tyr Asn Ser Ile Cys Asn Tyr Tyr Asp Asn Gln Asn Val Lys Thr Asn
        115                120                125

Lys Lys Asn Leu Pro Pro Tyr Asn Asn Ile Lys Asn Gln His Asp His
        130                135                140

Val Val Ser Thr Asn Asn Lys Lys Arg Asn Ser Leu Gly Lys Asp Lys
145                150                155                160

Gln Asn Ile Leu Leu Ile Asp Lys Gln Leu Asn Asn Thr Glu Tyr Lys
        165                170                175

Ser Asn Ile Glu Gln Gln Lys Gln Asp Asn Asn His Ser Tyr Phe Glu
        180                185                190

Lys Lys Glu Lys Lys Lys Lys Lys Lys Ile His Lys Phe Lys Thr
        195                200                205

Ser Lys Lys Gln Glu Asn Ile Leu Asn Met Phe Glu Asn Asn Leu Asn
        210                215                220

Tyr Ser Ile Asp Lys Leu Asn Lys Lys Thr Lys Lys Tyr Glu Ile Phe
225                230                235                240

Thr Gln Lys Glu Asn Ile Lys Ser Asp Val Leu Gln Asn Glu Ile Leu
        245                250                255

Lys Lys Ile Leu Ser Lys Asp Thr Lys Ser Lys Asn Lys His Asp Gln
        260                265                270

Val Lys Asn Lys Asp Asp Gln Val Lys Asn Lys Asp Asp Lys Ile Lys
        275                280                285

Asn Lys His Asp Lys Val Lys Asn Lys His Asp Lys Val Lys Asn Lys
        290                295                300

Lys Asp Lys Ile Lys Asn Lys Lys Asp Lys Val Lys Asn Lys Asp Asp
305                310                315                320

Lys Ile Lys Asn Asn Asn Asp Glu Arg Gln Asn Lys Ile Lys Met Pro
                325                330                335

Ile Asn Asn Asn Gln Asn Asn Phe Lys His Gln Asp Lys Cys Asn Ile
        340                345                350

Asn His Gln His Glu Asn Asn Lys Ile Lys His Tyr Ile Asp Asp Ile
        355                360                365

Thr Asn Gln Gln Asn Glu Gln Asn Asn Lys Asp Leu His Asn Cys Leu
        370                375                380

Asn Asp His Gln His Ile His Asn Lys Asn Ile Ile Thr Glu His Thr
385                390                395                400

Asn Tyr Leu His Asn His Ile Thr Thr Asn Ala His Val Asn Asn Asn
                405                410                415

Gln Pro Ile Ile Asn Ile Gln Gln Ile Phe Gln Val Ser Lys Ser Val
                420                425                430
```

-continued

```
Asp Asn Phe Arg Arg Gln Ile Gln Ile Lys Tyr Asn Lys Gln Asn Asn
            435                 440                 445
Gly Asn Glu Ile Lys Lys Arg Leu Gln Gln Tyr Asp Cys Ile Ile Asp
            450                 455                 460
Phe Asn Ala Asn Lys Asn Ile Ile Thr Gln Gly Ile Ala Glu Asn Lys
465                 470                 475                 480
Asn Glu Lys Lys Asn Glu Lys Lys Ile Asn Lys Asn Tyr Thr Phe
                    485                 490                 495
Tyr Asp Val Gly Ile Tyr Asp Asn Phe Ile Asn Ile Tyr Leu Lys Tyr
                500                 505                 510
Asn Asp Ile Asn Tyr Thr Thr Asp His Gln Ala Glu Tyr Ile Pro Ile
            515                 520                 525
Ile Leu Phe Phe Leu Asn Asn Val Lys Asn Asp Leu Tyr Asn Cys Tyr
            530                 535                 540
Lys Gln Met Ile Thr Tyr His Asn Asn Asn Ile Leu Asn His Asn Ser
545                 550                 555                 560
Asn Ile Leu Ser Lys Glu Asn Glu Lys Lys Gln Pro Phe Ser Thr Tyr
                    565                 570                 575
Asn Ile Ser Asn Leu Cys Ser Pro Asp Gln Met Val Ile Asn Lys Lys
                580                 585                 590
Met Asn Gln Arg Gln Ser Thr His Val Asp Glu Gln Lys Asp Thr Ser
            595                 600                 605
Cys His Ile Lys Asn Val Tyr Asn Asn Asn Asp Asn Asn Phe Val Ile
            610                 615                 620
Gln Asn Asn Glu Leu Leu Thr Ser Asn Leu Leu Ile Lys Asp Asn Asn
625                 630                 635                 640
Ile Asn Ser Lys Gln Asn Gln Asp Met Pro Asn Lys Ile Asn Phe Ala
                    645                 650                 655
Lys Glu Asp Asp Asn Lys Lys Cys Asp Glu Lys Asn Tyr Met Asp Asp
                660                 665                 670
Gln Lys Cys Gly Glu Lys Asn Tyr Met Asp Asp Lys Glu Lys Thr Ser
            675                 680                 685
Asn Ile Lys Gln Ile Leu Tyr Val Asn Lys Tyr Asn Glu Lys Leu Lys
            690                 695                 700
Lys Leu Ile Arg Thr Phe Phe Leu His Cys Pro Thr Gly Thr Gly Lys
705                 710                 715                 720
Thr Phe Ile Tyr Leu Leu Pro Leu Phe Gln Glu Ile Ser Asn Tyr Asn
                    725                 730                 735
Phe Leu Glu Tyr Glu Gln Asn Gln Ile Gln Thr Lys Glu Ser Tyr Asp
                740                 745                 750
Glu Asn Asn Leu Phe Cys Lys His Lys Phe Phe Tyr Ala Asn Lys Asn
            755                 760                 765
Ile Asn Glu Gln Leu Thr Ser Phe Leu Cys Val Asn Lys Thr Glu Glu
            770                 775                 780
Gln Ile Phe Arg Asn Tyr Asn Ile Glu Arg Met Lys His Ile Phe Asn
785                 790                 795                 800
Ser Ile Ile Asn Gln Asn Asn Gln Val Asn Leu Lys Thr Glu Asn Thr
                    805                 810                 815
Thr Asn Gly Ser Leu Asn Glu Lys Glu Tyr Ala Phe His Glu Lys
                820                 825                 830
Lys Lys Leu Asn Asp Asn His Lys Asn His Ile Tyr Asn Thr Glu Arg
            835                 840                 845
Gln Lys Lys Lys Lys Asp Ile Leu Leu Ile Thr Tyr Asn Lys Glu Leu
850                 855                 860
```

```
Ala Val Gln Ile Tyr Glu Leu Tyr Lys Asp Ile Ile Asn Ser Phe Tyr
865                 870                 875                 880

Lys Ser Tyr Asp Ala Ser Phe Phe Lys Asn Asn Ser Ile Ile Tyr
            885                 890                 895

Pro Ser Ser Ile Gln Lys His Gly Gln Met Leu Ile Glu Lys Leu Asn
            900                 905                 910

Ile Asn Phe Lys Glu Lys Leu Asn Met Asn Val His Leu Leu Ile Gly
        915                 920                 925

Gly Asn Asn Ile Lys Tyr Gln Leu Lys Ser Leu Lys Lys Lys Lys Asn
        930                 935                 940

Asn Asn Ile Lys Asn Ile Asn Ile Asn Lys Asn Ile Asn Val Asn Lys
945                 950                 955                 960

Asn Ile Asn Val Asn Lys Asn Ile Asn Ile Asn Lys Asn Ile Asn Val
                965                 970                 975

Asn Ile Asn Ser Asn Asn Asn Ser Asn Asn Asn Tyr Tyr Tyr Asp Lys
            980                 985                 990

Asp Asn His Val Asn Asp Lys Met Asp Arg His His Ile Asn Asp Lys
        995                 1000                1005

His Ser Asn Glu Gln His Val Ile Gln Ser Ser Phe Cys Asp Glu
    1010                1015                1020

Glu Asn Ile Asn Ile Tyr Ile Gly Thr Pro Gly Arg Leu His Lys
    1025                1030                1035

Leu Ile His Glu Lys Lys Ile Lys Leu Asn Asn Ile Ser Thr
    1040                1045                1050

Val Ile Phe Asp Glu Tyr Asp Phe Phe Phe Asn Ser Met Lys Val
    1055                1060                1065

Lys Asn Asn Leu Lys Asn Lys Glu His Val Val Glu Leu Glu Asn
    1070                1075                1080

Gln Phe Phe Ala Lys Leu Leu Lys Ser Ile Tyr Leu Lys Asn Lys
    1085                1090                1095

Glu Glu Ile Val Gln Lys Lys Lys Ser Ile Lys Asp Thr Lys Asn
    1100                1105                1110

Ile His His Tyr Lys Asn Asn Asn Ser Val Ile Asn Val Ile Cys
    1115                1120                1125

Cys Ser Ala Thr Ser Ala Ile Tyr Pro Tyr Leu Thr Tyr Thr Lys
    1130                1135                1140

His Ile Ile Thr Thr Asn Phe Leu Asn Asn Leu Tyr Ser Glu Leu
    1145                1150                1155

Ile Ser Asp Lys Tyr Ile Thr Asp Gln Asn Tyr Lys Glu Arg Lys
    1160                1165                1170

Gln Ile Gln Asn Glu Asp Ile Thr Lys Lys Lys Lys Glu Ile Val
    1175                1180                1185

Ser Asp Asp Asn Asp Asn Asp Asn Asp Asn Asp Asn Asp Asn Asn
    1190                1195                1200

Asn Asn Asn Asn Asn Asn Asn Asn Asn Asn Asp Gly Asp Ala Ile
    1205                1210                1215

Tyr Ser Ser Ser Ser Ser Ser Cys Ser Asn Ser Cys Ser Ser
    1220                1225                1230

Gly Ala Gly Leu His Leu Asn Asn Gln Lys Asn Asn Asp Thr Glu
    1235                1240                1245

Gln Thr Asn Asn Ser Phe Ile Asn Tyr Lys Lys Glu Gln Ile Met
    1250                1255                1260

Leu Asn Asp Leu Phe Lys Ile Asn Asn Ile Val Lys Met Pro Lys
```

```
                 1265                1270                1275

Asn Leu Ile His Leu Asn Tyr Cys Tyr Asp Lys Lys Asn Lys Glu
         1280                1285                1290

Arg Asn Asn Asn Ala Thr Ser Asn Phe Leu Arg Val Leu Phe Ser
         1295                1300                1305

Asn Pro Leu Asn Lys Asn Val Leu Val Phe Cys Asn Thr Lys Lys
         1310                1315                1320

Lys Val Leu Asp Leu Trp Ser Leu Phe Arg Asn Arg Phe Asp Val
         1325                1330                1335

Asp Ile Gln Thr Ile Phe Ser Gln Lys Asp Lys Gly Lys Lys Lys
         1340                1345                1350

Ile Phe Lys Asp Ile Asn Tyr Ala Asn Phe Phe Lys Asn Asp Leu
         1355                1360                1365

Ile Asp Tyr Lys Asn Leu Lys Lys Tyr Val Asn Phe Leu Phe Ile
         1370                1375                1380

Ser Thr Asn Leu Leu Tyr Arg Gly Ile Asn Cys Met Gly Phe Thr
         1385                1390                1395

Thr Ile Ile Asn Tyr Asp Met Pro Phe Asp Thr Thr Glu Tyr Val
         1400                1405                1410

His Arg Cys Gly Arg Ile Gly Arg Ile Asn Asn Lys Gly Ala Ile
         1415                1420                1425

Ile Asn Ile Phe Glu Lys Lys Met Lys Arg Asn Tyr Asn Lys Glu
         1430                1435                1440

Ile Phe Asn Lys Leu Asn Ile Lys Thr Tyr Asp Ile Asp Cys Tyr
         1445                1450                1455

Met Asn Asn Met Phe Thr Phe Lys Glu Lys Val Lys Arg Lys
         1460                1465                1470

<210> SEQ ID NO 5
<211> LENGTH: 336
<212> TYPE: PRT
<213> ORGANISM: Plasmodium falciparum

<400> SEQUENCE: 5

Met Lys Leu His Tyr Thr Lys Ile Leu Leu Phe Phe Pro Leu Tyr
1               5                   10                  15

Ile Leu Val Tyr Ser Lys Asn Lys Pro Ser Ile Thr Pro His His Thr
            20                  25                  30

Gln Thr Asn Arg Ser Leu Cys Glu Cys Asp Thr Gln Ser Thr Asn Tyr
        35                  40                  45

Asn Asn Asp Glu Asp Ile Lys Ser Val Lys Glu Ile Phe Asp Arg Gln
50                  55                  60

Thr Ser Gln Arg Phe Glu Glu Tyr Glu Glu Arg Met Gln Glu Lys Arg
65                  70                  75                  80

Gln Lys Arg Lys Glu Gln Arg Asp Lys Asn Ile Gln Glu Ile Glu
                85                  90                  95

Lys Asp Arg Met Asp Lys Leu Leu Ala Glu Val Glu Lys Gly Cys
            100                 105                 110

Leu Arg Cys Gly Cys Gly Leu Gly Gly Val Ala Ala Gly Val Gly Ile
        115                 120                 125

Phe Gly Thr Val Ala Val Lys Glu Leu Thr Lys Ala Ser Thr Val Ala
    130                 135                 140

Ala Ile Ala Ala Ala Gln Glu Ala Ala Ala Lys Gly Ala Val Ala
145                 150                 155                 160

Gly Ala Glu Ala Gly Ile Lys Thr Val Ile Ser Gly Leu Gln Lys Leu
```

```
                         165                 170                 175
Asp Ile Ser Thr Leu Asn Gly Gln Thr Leu Val Ser Tyr Phe Asp Thr
            180                 185                 190

Thr Asp Tyr Thr Asn Phe Lys Thr Ile Ala His Ala Ile Asn Thr Gln
        195                 200                 205

Tyr Asp Pro Ser Pro Cys Val Leu Gly Arg Ser Gly Ala Ser Glu Ser
    210                 215                 220

Phe Cys Ser Trp Val Arg Ala Asn Phe Phe Ala Pro Gln Glu Ile Ser
225                 230                 235                 240

Gly Lys Val Ser Thr Tyr Glu Ser Ile Glu Ile Gly Val Thr Ser
            245                 250                 255

Ile Val Ser Asp Ala Lys Lys Ala Ala Ala Ala Val Lys Lys Ala
        260                 265                 270

Thr Asp Glu Val Ile Lys Asn Ser Thr Ala Ala Ala Glu Ser Thr Tyr
    275                 280                 285

Ala Gly Cys Gln Thr Ala Ile Ile Ala Ser Val Val Ala Ile Ile Ile
            290                 295                 300

Ile Ala Leu Val Met Ile Ile Ile Tyr Leu Val Leu Arg Tyr Arg
305                 310                 315                 320

Lys Lys Lys Met Asn Lys Lys Ala Gln Tyr Thr Glu Leu Leu Asn Gln
            325                 330                 335

<210> SEQ ID NO 6
<211> LENGTH: 1097
<212> TYPE: PRT
<213> ORGANISM: Plasmodium falciparum

<400> SEQUENCE: 6

Met Leu Gly Leu Lys Arg Lys Asn Val Phe Tyr Leu Leu Val Ser Val
1               5                   10                  15

Pro Ser Leu Phe Ala Tyr Phe Leu Lys Arg His Lys Asp Asn Glu Asn
            20                  25                  30

Asn Tyr Glu Thr Leu Ile Asn Asn Asp Ile Glu Lys Ile Lys Lys
        35                  40                  45

Ile Arg Ile His Asn Lys Cys Ser Tyr Ile Pro Leu Leu Phe Leu Asn
    50                  55                  60

Ile Tyr Asp Ser Tyr Ile Tyr Lys Asn Lys Ile Leu Arg Trp Leu Tyr
65                  70                  75                  80

Phe Lys Phe Arg Lys Arg Arg Lys Asp Lys Glu Glu Tyr Tyr Ile
            85                  90                  95

Thr Asn Met Val Arg Lys Lys Arg Arg Glu Ala Ile Lys Tyr Asn Phe
        100                 105                 110

Ile Ser Asp Glu Gln Asn Leu Phe Asn Lys Phe Tyr Ile Tyr Glu Ile
    115                 120                 125

Val Leu Glu Tyr Ser Leu Lys Tyr Gly Ile Leu Ser Pro His Leu Ser
130                 135                 140

Leu Tyr Ile Leu Lys Asn Ile Ser Glu His Cys Val Asn Ile Tyr Pro
145                 150                 155                 160

Ser Leu Tyr Tyr Tyr Asn Lys Leu Asp Asn Lys His Asn Leu Ile Asn
            165                 170                 175

Glu Lys Lys Leu Lys Tyr Phe Lys Gln Ile Asn Asn Glu His Thr Gln
        180                 185                 190

Gln Ala Pro Thr Asn His Thr His Asn Asn Asn Asn Asn Lys
    195                 200                 205

Lys Pro Leu Asp Ile Asn Ile His Ser Cys Lys Asn Thr Asn Ile Ser
```

-continued

```
               210                 215                 220
Ser Tyr Ser Thr Tyr Asn Asn Met Glu Lys Glu Asn Ile Asn Ile Tyr
225                 230                 235                 240

Asp Lys Tyr Asn Ile His Asn Phe Tyr Thr Glu Lys Ser Ile Ser Tyr
                245                 250                 255

Lys Asp Glu Asn Cys Gln His Ile Thr Leu Asn Met Ile Tyr Leu Leu
                260                 265                 270

Asn Gln Thr Tyr Asp Asn Ile Cys Arg Ile Cys Leu Asn Thr Asn Thr
                275                 280                 285

Asn Ile Tyr Ile Asn Phe Tyr Met Ile Asn Ile Leu Lys Tyr Ile Cys
                290                 295                 300

Tyr Lys Asn Met Glu Ile Ile Leu Leu Asn Tyr Asn His Ile Glu Asp
305                 310                 315                 320

Met Lys Lys Lys Ile Asn Gln Lys Asn Asn Thr Asn Thr Ser Leu Phe
                325                 330                 335

Lys Tyr Ile Tyr Ser Phe Phe Phe Lys Lys Glu Asn His Ile
                340                 345                 350

Tyr Asp Leu Phe Glu Asp Gln Met Met Asn His Leu His Lys Lys Glu
                355                 360                 365

Asn Asp Lys Phe Tyr Asn Tyr Ser Asn Glu Asn Thr His Asn Asn Ile
                370                 375                 380

Tyr Lys Tyr Ile Ser Asp Asn Tyr Phe Tyr Asp His Ile Asn Ser Ser
385                 390                 395                 400

Ser Asn Arg Cys Ser Phe Lys Asn Leu Lys Lys Gln Gln Thr Asp Asp
                405                 410                 415

Asn Thr Lys His Ile Ile Met Gly Lys Glu Lys Tyr Pro Met Asn Lys
                420                 425                 430

Ser Asp His Glu Lys Lys Asn Asn Thr Cys Gly Asn Ile Asn Ile
                435                 440                 445

Glu Lys Asp Gln Lys Lys Asp Ile Leu Lys Lys Ile Tyr Phe Leu Lys
                450                 455                 460

Gly Asn Lys Leu Asp Asp Ile Gln Ile Leu Asn Glu Leu Tyr Val Met
465                 470                 475                 480

Ile Tyr Met Arg Leu Leu Phe Glu Cys Ser Leu Lys Leu Ile Ser Ile
                485                 490                 495

Lys Lys Asn Ile His Leu Leu Glu Lys Lys Met Glu Phe Asp Lys Asp
                500                 505                 510

Asn Lys Ile Ile Tyr Leu Asn Ser Ala Asp Tyr Met Asn Asn Leu Arg
                515                 520                 525

Arg Asn Ile Leu Lys Arg Phe Ser Lys Asn Glu Glu Arg Glu Asn Ile
                530                 535                 540

Asn Ser Phe Ala Ser Phe Pro Phe Leu Leu Ser Lys Asn Ile Ile Tyr
545                 550                 555                 560

Phe Glu Asp Glu Ile Gly Arg Ser Arg Asp Asn Thr Ile Tyr Asn Asn
                565                 570                 575

Val Tyr Asp Lys Glu Thr Asn Lys Thr Thr Thr Asn Asn Asn Asn
                580                 585                 590

Asp Asn Asn Asp Asn Ile Cys Ser Asn Asn Asp His Ile Cys Ser Asn
                595                 600                 605

Asn Asn Asp His Ile Cys Ser Asn Asn Asn Asp His Ile Cys Ser Asn
                610                 615                 620

Asn Asn Asn Asn Ile Cys Ser Asn Asn Asn Asn Ile Cys Ser Asn
625                 630                 635                 640
```

-continued

```
Asn Asn Asn Asn Ile Cys Ser Asn Asn Asn Asn Ile Cys Ser Asn
                645                 650                 655

Lys Met Leu Asp Glu Phe Cys Gln Asp Asn Lys Phe Asn Asp Tyr Asn
            660                 665                 670

Thr Arg Lys Lys Glu Lys Arg Lys Arg Ile Tyr Glu Leu Ala Lys Ile
        675                 680                 685

Tyr Thr Asn Asn Ile Phe Asp Tyr Leu Lys Gly Lys Lys Glu Lys His
    690                 695                 700

Gln Asn Glu Asp Asn Thr Ile Asn Leu Tyr Tyr Ile Lys Lys Lys Phe
705                 710                 715                 720

Pro Trp Ile Phe Tyr Leu Lys Asn Ile Ile Lys Asn Lys Asp Thr Ser
                725                 730                 735

Phe Ile Glu His Asn Asn Asn Ile Val Asn Gly Asp Ile Lys Asn Asn
            740                 745                 750

Asn Ile Ile Phe Lys Lys Lys Tyr Asn Leu Phe Glu Ser Ser Ile Ile
        755                 760                 765

Ser Tyr Phe Tyr Ile Lys Asp Ile Tyr Glu Tyr Asn Tyr Lys Leu Arg
    770                 775                 780

Leu Tyr Tyr Ile Tyr Asp Asn Leu Ile Lys Lys Phe Cys Arg Tyr Phe
785                 790                 795                 800

Leu Lys Met Asn Glu His Ile Asn Arg Lys Leu Tyr Lys Met Lys Arg
                805                 810                 815

Ala Phe His Tyr Tyr Ile Tyr Asn Phe Asp Gln Phe Ile Ile Asn Asn
            820                 825                 830

Tyr Tyr His Ile Ile His Lys Lys Asn Ile His Lys Ile His Ile His
        835                 840                 845

Leu Lys Gln Cys Lys Asp Lys Glu Ile Asp Ile Val Lys Phe Lys Asp
    850                 855                 860

Leu Tyr Tyr Cys Met Ile Asn Asn Ile Asn Asn Ile Phe Ser Tyr Ile
865                 870                 875                 880

His Lys Val Asp His Asn Glu Cys Val Tyr Arg Ile Phe Lys Ala Tyr
                885                 890                 895

Asn Lys Ile Leu Leu Tyr Glu Tyr Asn Tyr Leu Asn Glu Lys Glu Asn
            900                 905                 910

Ile Tyr Tyr Lys Asn Lys Ile Lys Lys Tyr Leu Thr Tyr Leu Asn Asn
        915                 920                 925

Asn Ile Ser Asn Asp Leu Tyr Pro Tyr Asn Ile Ser Tyr Asn Lys Ile
    930                 935                 940

Tyr Asn Gln Asn Lys Tyr Lys Asn Arg Lys Asn Phe Ser His Ile Phe
945                 950                 955                 960

Tyr Ser Leu Lys Asn Asp Ile His Leu Leu Leu Phe Leu Tyr Thr Gln
                965                 970                 975

Arg Ile Gln Asn Cys Cys Asp Ile Phe Ser Tyr Ile Tyr Lys Lys Tyr
            980                 985                 990

Asn Phe Asn Glu Lys Asn Pro Phe Leu Asn Tyr Leu Tyr Tyr Glu Leu
        995                 1000                1005

His Tyr Ile Val Tyr Ser Glu Lys Lys Lys Lys Lys Phe Phe
    1010                1015                1020

Ser Phe Ile Ser Ser Ser Pro Tyr Ser Tyr Asp Thr Met Val Asn
    1025                1030                1035

Ser Phe Thr Phe Ser Tyr Phe Phe Phe Ser Leu Ser Tyr Leu Leu
    1040                1045                1050

Phe Ile Leu Phe Tyr His Pro Asp Met Tyr Ala Ser Tyr Ile Phe
    1055                1060                1065
```

```
Phe Lys  Thr Leu Thr Tyr Ser  Gly Leu Pro Thr Tyr  Tyr Tyr Ser
    1070            1075              1080

Leu Tyr  Asn Asn Ile Met Val  Val Cys Gly Pro Lys  Thr Trp
    1085            1090              1095

<210> SEQ ID NO 7
<211> LENGTH: 1485
<212> TYPE: PRT
<213> ORGANISM: Plasmodium falciparum

<400> SEQUENCE: 7

Met Lys Tyr Ile Ser Ile Leu Ile Val Phe Phe Glu Leu Tyr Phe Ile
1               5                   10                  15

Leu Asn Phe Asn Val Thr Ser Cys Phe Gln Leu Lys Arg Asn Thr Pro
            20                  25                  30

Phe Tyr Val Tyr Asn Arg Asn Ile Ile Ser Cys Ile Lys Lys Asn Glu
        35                  40                  45

Arg Asn Lys Lys Val Leu Asn Leu Glu Lys Ser Val Lys Asp Gly Lys
    50                  55                  60

Cys Val Lys Asn Leu Asn Ile Asn Lys Asn Glu Ile Tyr Lys Asp Ile
65                  70                  75                  80

Glu Ser Tyr Leu Lys Asn Asp Ala Ser Ile Ser Ser Asn Lys Asn Asn
                85                  90                  95

Asp Ile Asn Asn Leu Asn Asp Ile Thr Phe Thr Asn Phe Val Ser Ile
            100                 105                 110

Ser Asn Asp Trp Asn Asn Ile Val Ile Glu Asp Gly Asn Asn Lys Asp
        115                 120                 125

Ile Arg Lys Leu Thr Asp Phe Leu Phe Lys Glu Tyr Lys Arg Ala Tyr
    130                 135                 140

Ala Tyr Ile Asp Glu Lys Ala Arg Asn Ile Asn Asn Ile Val Asn Ser
145                 150                 155                 160

Glu Lys Ile Lys Ser Leu Leu Asp Lys Phe Gly Ser Ile Leu Ile Asp
                165                 170                 175

Asp Met Asn Ile Asp Glu Phe Tyr Lys His Ile Glu Met Cys Phe Leu
            180                 185                 190

Leu Leu Asn Asn Cys Lys Asp Asn Tyr Ile Ser Phe Ser Leu Ile Lys
        195                 200                 205

Asn Glu Ile Ile Asn Ile Val Asn Gln Ile Ile Lys His Ser Gln Lys
    210                 215                 220

Phe Leu Arg Asp Glu Gln Ile Cys Lys Lys Met Lys Asn Asp Phe Met
225                 230                 235                 240

Asn Ile His Asn Leu Ile Lys Glu Ile Lys Lys Asn Asp Ile Ile Lys
                245                 250                 255

Met Asn Ile Lys Asn Phe Met Ser Val Ile Asn Ser Asn Ile Val Leu
            260                 265                 270

Asn Asn Asn Asn Ile Phe Tyr Phe Leu Thr Glu Ile Phe Ser Ser Leu
        275                 280                 285

Asn Phe Leu Met Lys Asp Asn Pro Gln Leu Ile Tyr Glu Tyr Asp Tyr
    290                 295                 300

Ile Ile Asn Pro His Phe Phe Phe Leu Cys Ile Phe Ser Leu Tyr Ser
305                 310                 315                 320

Tyr Asn Leu Ser Lys Thr Arg Phe Tyr Phe Leu Leu Ile His
                325                 330                 335

Asn Gln Phe Asp Leu Lys Glu Asn Val Ala Lys Tyr Asp Asn Met
            340                 345                 350
```

```
Asn Tyr Asn Arg Tyr Lys Asn Ser Ile Ile Asn Ile Ile Phe Glu Arg
        355                 360                 365

Glu Lys Lys Glu Tyr Glu Ser Ile Lys Glu Ile Ile Val Gln Ser Asp
        370                 375                 380

His Ser Arg Asn Thr Gln Asn Thr Asn Glu Thr Leu Asp Asp Lys Asn
385                 390                 395                 400

Ile Asn Ile Glu Gln Lys Glu Asn Lys Thr Asn Glu Asp Ser Val Ser
                405                 410                 415

Phe Ile Asp Asn Asn Asn Lys Glu Glu Ala Ser Lys Lys Ile Trp Asp
                420                 425                 430

Gly Val Leu Phe Lys Glu Leu Tyr Asp Asn Ile Leu Ile Lys Ile Leu
                435                 440                 445

Phe Phe Tyr Ile Phe Phe Tyr Phe Gly Asp His Tyr Phe Cys Ile Ile
            450                 455                 460

Leu Leu Leu Asn Phe Lys Tyr Ile Ile Glu Glu Asn Lys His Asp
465                 470                 475                 480

Asp Asn Ile Lys Lys Thr Ile Asn Tyr Cys Phe Phe Leu Leu Leu Asp
                485                 490                 495

Asn Leu Tyr His Ile Arg Asp Tyr Ser Lys Ile Ile Leu Leu Leu Ser
            500                 505                 510

Leu Tyr Lys Asn Lys Phe Asn Thr Phe Asn Asp Lys His Leu Asn Asp
            515                 520                 525

Val Gln Lys Ile Phe Asn Ser Val Ile Asn Asn Ile Asn Asp Glu Glu
        530                 535                 540

Cys Ser Val Asp Met Ser Lys Leu Leu Leu Glu Ile Lys Glu Cys Ile
545                 550                 555                 560

Lys Asn Val Glu Asn Glu Arg Asn Cys Asp Arg Gln Glu Asn Val Met
                565                 570                 575

Asp Ser Pro Glu Asn Lys Lys Met Asp Asp Phe Cys Tyr Leu Ile Asn
            580                 585                 590

Lys Asn Glu Met Ile Ser Lys Glu Glu Ile Lys Ser Glu Asn Val Lys
            595                 600                 605

Ala Tyr Asn Ser Val Val Lys Glu Asp Met Glu Gly Cys Val Lys Asn
        610                 615                 620

Leu Lys Asn Gly Asp Asn Asn Phe Ile Lys Glu Ser Gln His Met Asn
625                 630                 635                 640

Glu Lys Phe Asn Ser Tyr Leu Phe His Leu Leu Lys Asn Lys Lys Tyr
                645                 650                 655

Asp Lys Ile Glu Gln Leu Glu Lys Arg Asp Asn Leu Tyr Val Asn Asn
            660                 665                 670

Lys Thr Tyr Ser Leu Phe Ile Gln Ser Phe Leu Gly Asn His Lys Tyr
        675                 680                 685

Asp Lys Val His Lys Val Tyr Lys Lys Met Lys Gln Lys Lys Asn Ile
        690                 695                 700

Pro Ile Lys Tyr Leu Asn Ala Lys His Leu Ile His Ser Phe Lys Asn
705                 710                 715                 720

Cys Asp Ile Asp Lys Gly Asp Val Leu Asn Glu Leu Gln Leu Ile Asn
                725                 730                 735

Lys Ile Tyr Leu Asn Leu Tyr Phe Ser Lys Asp Ser Tyr Phe Val Leu
        740                 745                 750

Thr Lys Thr Leu Leu Tyr Lys His Met Cys Asp Tyr Leu Lys Lys Lys
            755                 760                 765

Cys Glu Met Lys Ile Ile Ile Asp Ile Phe Asn Ile Asn Glu Leu Leu
```

|     |     |     |     |     |     |     |     |     |     |     |     |     |     |     |
| --- | --- | --- | --- | --- | --- | --- | --- | --- | --- | --- | --- | --- | --- | --- |
| | | | | 770 | | | | | 775 | | | | | 780 |
| Lys | Tyr | Phe | Ile | Lys | Phe | Lys | Ser | Phe | Ile | Asn | Ile | Lys | Lys | Leu | Tyr |
| 785 | | | | | 790 | | | | | 795 | | | | | 800 |
| Phe | Ile | Leu | Leu | Arg | Tyr | Ser | Tyr | Ile | Lys | Thr | Tyr | Lys | Thr | Tyr | Leu |
| | | | | 805 | | | | | 810 | | | | | 815 | |
| Ile | Leu | Ile | Arg | Phe | Phe | Asn | Asn | Leu | Asn | Tyr | Glu | Asn | Asn | Ser | Glu |
| | | | 820 | | | | | 825 | | | | | 830 | | |
| Asn | Ile | Glu | Ser | Asp | Val | Ile | Asp | Asn | Lys | Asn | Lys | Glu | Asn | Ser | |
| | | 835 | | | | | 840 | | | | | 845 | | | |
| Asn | Glu | Glu | Asn | Val | Gln | Asn | Val | Gln | Asn | Val | Glu | Asn | Val | Gln | Asn |
| 850 | | | | | 855 | | | | | 860 | | | | | |
| Asp | Asn | Asn | Ile | Lys | Ile | Glu | Asn | Cys | Val | Lys | Cys | Ala | Leu | Glu | Lys |
| 865 | | | | | 870 | | | | | 875 | | | | | 880 |
| Asn | Asn | Glu | Ile | Tyr | Asn | Asp | Ile | Ile | Asn | Leu | Arg | Lys | Lys | Lys | Leu |
| | | | | 885 | | | | | 890 | | | | | 895 | |
| Tyr | Glu | Tyr | Ile | Tyr | Pro | Ile | Glu | Tyr | Ser | Lys | Met | Asp | Val | Asp | Phe |
| | | | 900 | | | | | 905 | | | | | 910 | | |
| Tyr | Asn | Lys | Ile | Tyr | Asp | Leu | Ser | Lys | Lys | Asp | Lys | Tyr | Asp | Met | Ser |
| | | | 915 | | | | | 920 | | | | | 925 | | |
| Leu | Ile | Ile | Leu | Ser | Asn | Phe | Ile | Thr | Glu | Tyr | Ile | Leu | Ser | Asp | Tyr |
| 930 | | | | | 935 | | | | | 940 | | | | | |
| Ser | Ser | Asp | Asp | Ile | Val | Glu | Asn | Glu | Tyr | Asn | Ile | Glu | Asn | Ile | |
| 945 | | | | | 950 | | | | | 955 | | | | | 960 |
| Leu | Asn | Ile | Phe | Phe | Glu | Ser | Ile | Asn | Leu | Phe | Phe | Tyr | Lys | Gln | Asp |
| | | | | 965 | | | | | 970 | | | | | 975 | |
| Tyr | Lys | Ile | Thr | Leu | Asn | Ile | Tyr | Phe | Phe | Leu | Leu | Leu | Phe | Leu | Asn |
| | | | 980 | | | | | 985 | | | | | 990 | | |
| Asn | Tyr | Val | Thr | Arg | Tyr | Ile | Arg | Asn | Asp | Met | Lys | Tyr | Trp | Thr | Phe |
| | | | 995 | | | | | 1000 | | | | | 1005 | | |
| Leu | Lys | Lys | Asn | Met | Leu | Asn | Phe | Phe | Leu | Ser | Gly | Asn | Tyr | Glu | |
| | | 1010 | | | | | 1015 | | | | | 1020 | | | |
| Val | Leu | Lys | Asn | Asn | Lys | Asp | Leu | Ile | Tyr | Glu | Tyr | Ile | Pro | Asn | |
| | | 1025 | | | | | 1030 | | | | | 1035 | | | |
| Phe | Ile | Leu | Asn | Ile | Ile | Ser | Leu | Cys | Ile | Lys | His | Leu | Lys | Asn | |
| | | 1040 | | | | | 1045 | | | | | 1050 | | | |
| Ile | His | Thr | Met | Lys | Asp | Val | Ser | Thr | Phe | Asn | Cys | Leu | Ala | Tyr | |
| | | 1055 | | | | | 1060 | | | | | 1065 | | | |
| Asn | Ser | Tyr | Asp | Val | Asn | Lys | Asn | Met | Asp | Thr | Ala | Val | Asn | Tyr | |
| | | 1070 | | | | | 1075 | | | | | 1080 | | | |
| Lys | Asn | Ile | Met | Tyr | Ile | Phe | Phe | Leu | Leu | Lys | Asn | Asn | Leu | Tyr | |
| | | 1085 | | | | | 1090 | | | | | 1095 | | | |
| Leu | His | Asp | Glu | Thr | Met | Glu | Ile | Asp | Ile | Tyr | Asp | Lys | Gln | Thr | |
| | | 1100 | | | | | 1105 | | | | | 1110 | | | |
| Ile | Lys | Lys | Lys | Ile | Lys | Asn | Ser | Ser | His | Asn | Lys | Asn | Asn | Ser | |
| | | 1115 | | | | | 1120 | | | | | 1125 | | | |
| Arg | Lys | Leu | Asn | Cys | Leu | Tyr | Lys | Asp | Val | Ile | Glu | Lys | Asn | Tyr | |
| | | 1130 | | | | | 1135 | | | | | 1140 | | | |
| Lys | Glu | Glu | Asn | Asn | Met | Gly | Glu | Thr | Asn | Ile | Phe | Asn | Asn | Phe | |
| | | 1145 | | | | | 1150 | | | | | 1155 | | | |
| Ser | Asn | Ser | Ile | Ala | Asn | Val | Phe | Val | Lys | Leu | Lys | Tyr | Thr | Ile | |
| | | 1160 | | | | | 1165 | | | | | 1170 | | | |
| Gly | Ser | Asp | Lys | Lys | Pro | Glu | His | Ser | Leu | Lys | Asp | Phe | Leu | Phe | |
| | | 1175 | | | | | 1180 | | | | | 1185 | | | |

| Asn | Arg | Leu | Lys | Met | Leu | Val | Ser | Asn | Ile | Ser | Arg | Glu | Gly | Lys |
|     | 1190 |     |     |     | 1195 |     |     |     |     | 1200 |     |     |     |     |

| Val | Gln | Lys | His | Asp | Ser | Ile | Ile | Asn | Ile | Leu | Lys | Asp | Ile | Phe |
|     | 1205 |     |     |     | 1210 |     |     |     |     | 1215 |     |     |     |     |

| Phe | Thr | Tyr | Ser | Asn | Ile | Ile | Tyr | Leu | Asn | Ser | Asn | Asp | Phe | Val |
|     | 1220 |     |     |     | 1225 |     |     |     |     | 1230 |     |     |     |     |

| His | Ile | Tyr | Glu | Lys | Leu | Ser | Thr | Ile | Tyr | Asp | Asn | Val | Leu | Ser |
|     | 1235 |     |     |     | 1240 |     |     |     |     | 1245 |     |     |     |     |

| Val | Leu | Ser | Ile | Ile | Ile | Phe | Asn | Glu | Asn | Lys | Asn | Phe | Lys | Glu |
|     | 1250 |     |     |     | 1255 |     |     |     |     | 1260 |     |     |     |     |

| Asn | Asn | Thr | Glu | Ser | Leu | Lys | His | Ile | Gln | Gln | Pro | Leu | Gln | Thr |
|     | 1265 |     |     |     | 1270 |     |     |     |     | 1275 |     |     |     |     |

| Asn | Asn | Glu | Ile | Asn | Ile | His | Asn | Phe | Ile | Thr | Met | Phe | Val | Ser |
|     | 1280 |     |     |     | 1285 |     |     |     |     | 1290 |     |     |     |     |

| Met | Asn | Lys | Asn | Tyr | Phe | Lys | Asp | Leu | Leu | Asn | Gln | Lys | Val | Val |
|     | 1295 |     |     |     | 1300 |     |     |     |     | 1305 |     |     |     |     |

| Gln | Asp | Ile | Leu | Arg | Lys | Tyr | Gly | Ser | Phe | Ile | Gln | Met | Cys | Ile |
|     | 1310 |     |     |     | 1315 |     |     |     |     | 1320 |     |     |     |     |

| Tyr | Phe | Asp | Leu | Lys | Lys | Lys | Lys | Val | Asp | Ser | Ile | Ile | Asn | Leu |
|     | 1325 |     |     |     | 1330 |     |     |     |     | 1335 |     |     |     |     |

| Leu | Glu | Leu | Ser | Arg | Lys | Cys | Asn | Ile | Pro | Ile | Ser | Thr | Glu | Thr |
|     | 1340 |     |     |     | 1345 |     |     |     |     | 1350 |     |     |     |     |

| Leu | Ile | Asp | Val | Phe | Asn | Leu | Tyr | Phe | Glu | Lys | Lys | Met | Asn | Asn |
|     | 1355 |     |     |     | 1360 |     |     |     |     | 1365 |     |     |     |     |

| Leu | Ile | Phe | Lys | Glu | Phe | Glu | Met | Phe | Ser | Leu | Ser | Lys | Glu | Thr |
|     | 1370 |     |     |     | 1375 |     |     |     |     | 1380 |     |     |     |     |

| Glu | Asn | Phe | Glu | Leu | Tyr | Tyr | Ile | Val | Met | Lys | Thr | Ala | Phe | Phe |
|     | 1385 |     |     |     | 1390 |     |     |     |     | 1395 |     |     |     |     |

| Glu | Glu | Asn | Val | Arg | Ile | Ala | Leu | Lys | Val | Phe | Ser | Ile | Val | Leu |
|     | 1400 |     |     |     | 1405 |     |     |     |     | 1410 |     |     |     |     |

| Asn | Ile | Phe | Asn | Leu | Lys | Ile | Ile | Pro | Leu | Asn | Phe | Phe | Glu | Cys |
|     | 1415 |     |     |     | 1420 |     |     |     |     | 1425 |     |     |     |     |

| Ile | Leu | Leu | Ile | Leu | Lys | Lys | Lys | Gly | Lys | Phe | Asn | Val | Leu | Tyr |
|     | 1430 |     |     |     | 1435 |     |     |     |     | 1440 |     |     |     |     |

| Glu | His | Ile | Asp | Lys | Leu | His | Arg | Gln | Leu | Ile | Asn | Tyr | Glu | Lys |
|     | 1445 |     |     |     | 1450 |     |     |     |     | 1455 |     |     |     |     |

| Asn | Lys | Asn | Phe | His | Asn | Ile | Glu | Asn | Leu | Ser | Leu | Asp | Ile | Arg |
|     | 1460 |     |     |     | 1465 |     |     |     |     | 1470 |     |     |     |     |

| Lys | Leu | Leu | Glu | Lys | Tyr | Lys | Lys | Glu | Lys | Gln | Phe |
|     | 1475 |     |     |     | 1480 |     |     |     |     | 1485 |     |

<210> SEQ ID NO 8
<211> LENGTH: 2507
<212> TYPE: PRT
<213> ORGANISM: Plasmodium falciparum

<400> SEQUENCE: 8

| Met | Thr | Lys | Ile | Gln | Asn | Asp | Ile | Met | Leu | Pro | Phe | Phe | Ser | Val | Ser |
| 1   |     |     |     | 5   |     |     |     |     | 10  |     |     |     |     | 15  |     |

| Ser | Lys | His | Cys | Lys | Asn | Asn | Thr | Asn | Val | Val | Thr | Tyr | Cys | Arg | Thr |
|     |     |     | 20  |     |     |     |     | 25  |     |     |     |     | 30  |     |     |

| Arg | Lys | Arg | Arg | Lys | Arg | Lys | Arg | Lys | Glu | Lys | Tyr | Cys | His | Arg |
|     |     |     | 35  |     |     |     |     | 40  |     |     |     |     | 45  |     |

| Cys | Ile | Asn | Ile | Arg | Lys | Leu | Ile | Lys | Tyr | Glu | Lys | Tyr | Asn | Asn | Leu |
|     | 50  |     |     |     |     | 55  |     |     |     |     | 60  |     |     |     |     |

-continued

```
Lys Ser Asn Tyr Val Tyr Ile Asp Leu Lys Lys Met Ile Arg Asn Lys
 65                  70                  75                  80

Ser Tyr Glu Asn Asp Tyr Lys Tyr Phe Val Lys Tyr Asn Asn Ile Lys
                 85                  90                  95

Ser Ser Asn Ile Ile Asn Ser Asn Ile Lys Asn Tyr Lys Lys Lys
            100                 105                 110

Tyr Leu Glu Ser Leu Pro Phe Tyr Asn Asp Ser Tyr Ile Thr Ser Met
            115                 120                 125

Tyr Ile Tyr Glu Ser Leu Val Leu Val Thr Trp Ser Asn Gly Ile Ile
            130                 135                 140

Ser Leu Phe Asn His Lys Tyr Asn His Ile Val Ser Arg Lys Val Thr
145                 150                 155                 160

Asn His Leu Ile Lys Asn Leu Cys Met Asn Cys Ser Glu Asn Met Ile
                165                 170                 175

Ala Phe Met Asp Asn Met Asp Ser Leu Tyr Phe Ile Asn Leu Asn Asn
            180                 185                 190

Asn Ile Ile Asn Lys Gly Leu His Lys Asn Val Ile Phe Ile Ser Asn
            195                 200                 205

Asp Ile Tyr Glu Lys Gly Tyr Asn Tyr Asn Asn Ile Asp Tyr Asn Asn
210                 215                 220

Asp Arg Glu Ile Asp Arg Leu Ser Val Asp Phe Thr Tyr Asn Lys Leu
225                 230                 235                 240

Asn Lys Lys Lys Lys Lys Met Tyr Asp Met Asn Asn Lys Lys Asp Asn
                245                 250                 255

Ile Ile Asn Val Ile Ile Ser Asp Glu Ile Met Lys Tyr Asn Ile Lys
            260                 265                 270

Asn Leu Thr Thr Phe Cys Ile Asn Pro Tyr Tyr Asn Asn Asn Asn
            275                 280                 285

Asn Asn Asn Asn Ile Cys Val Leu Thr Asn Lys Lys Thr Val Ser Leu
            290                 295                 300

Ile Tyr Ile Tyr Glu Tyr His Ile Asn Ser Val Leu Leu Phe Lys Asp
305                 310                 315                 320

Asp Asn Ile Leu Asn Ile Tyr Trp Tyr Glu Ser Phe Ile Phe Ile Cys
                325                 330                 335

Thr Pro Leu Ser Val Phe Val Ile Asn Phe Phe Asn Lys Thr Lys Ile
            340                 345                 350

Ala Gln Met Lys Phe Ile Gly Asn Leu Asn Gly Asn Val Asp Lys Thr
            355                 360                 365

Phe Phe Leu Phe Ile Glu Asn Tyr Thr Gly Lys Glu Lys Glu Phe Gln
            370                 375                 380

Gly Tyr Asn Lys Ile Asn Tyr Ile Lys Arg Lys Glu Lys Lys Met Glu
385                 390                 395                 400

Lys Lys Met Glu Arg Gln Lys Glu Asp Gln Thr Asp Asn Gln Lys Asp
                405                 410                 415

Gly Gln Lys Asp Gly Gln Thr Asp Gly Gln Thr Asp Gly Gln Thr Asn
            420                 425                 430

Asn Gln Lys Asp Asn Thr Lys Asn Gln Leu Ile His Cys Ser Gln Asn
            435                 440                 445

Asn Tyr Pro Cys Thr Tyr Glu Asn Leu Leu Tyr Val Ile Lys Thr Met
450                 455                 460

Trp Pro Asn Leu Phe Ser Val His Ile Cys Arg Gly Ile Glu Lys Gly
465                 470                 475                 480

Val Tyr Ile Ile Ala Lys Glu Lys Asn Ile Lys Ile Ile Lys Ile Gln
            485                 490                 495
```

```
Lys Ile Asn Glu Asn Tyr Ile Leu Ser Ile Asn Ile Leu Tyr Asn Thr
            500                 505                 510
Thr Tyr Asn Ile Leu Lys Asn Asp Phe Cys Leu Ser Val Ile Ala Phe
            515                 520                 525
Asn Met Asp Thr Tyr Ile Ser Asn Val Phe Thr Asn Tyr Lys Asp Ile
            530                 535                 540
Lys Lys Asn Lys Phe Leu Glu His Tyr Ile Leu Thr Leu Asn Asn Phe
545                 550                 555                 560
Phe Leu His Lys Thr Lys Met Thr Ile Phe Glu Thr Gln Gly Lys Gln
                565                 570                 575
Asn Glu Glu Asn Asp Lys Met Lys Leu Glu Gly Glu Asn Ile Asn Ile
            580                 585                 590
Gln Asn Asn Ser Asn Asp Tyr Asn Ile His Glu Leu Tyr Asn Asn Asn
            595                 600                 605
His Met Ile Tyr Lys Thr Ile Pro Gln Asn Glu Asp His Asn Val Asn
            610                 615                 620
Ile Asn Asn Asn Cys Ala Asp Asp Ile Ile Gln Ser Gln Lys Gln Lys
625                 630                 635                 640
Ile Thr Asn Ile Ser Tyr Asn Asn Asn Asn Asn Asn Gln Val Gln
                645                 650                 655
Pro Asn Lys Tyr Asn His Ala Asn Gln Thr Thr Thr Lys Glu Gln Asp
            660                 665                 670
Asn Phe Phe His Phe Tyr Lys Ser Asn Ile Tyr Asp Met Glu Asn Arg
            675                 680                 685
Thr Cys Asn Asn Asn Ile Leu Gln Tyr Cys Val Met Asn Asn Lys Ser
            690                 695                 700
Tyr Leu Phe His Asn Ile Ser Ser Lys Asn Ile Tyr Ile Lys Lys
705                 710                 715                 720
Lys Asn His Gln Phe Ser Leu Phe Ile Tyr Ser Ser Ile Asn Asn Thr
                725                 730                 735
Phe Ile Glu Phe Arg Pro Lys Thr Ile Glu Glu Ile Phe Tyr Glu Phe
            740                 745                 750
Met Leu Glu Arg Lys Asn Thr Asn Ile Ile Tyr Lys Lys Asn Ile Met
            755                 760                 765
Ile Lys Lys Lys Lys Cys Ser Thr Tyr Lys Lys Asn Arg Leu Ser Ile
            770                 775                 780
Ile Leu Lys Glu Leu Arg Lys Asp Lys Asn Arg Lys Glu Leu Thr
785                 790                 795                 800
Asn Ile Val Phe Lys Leu Ile Val His Phe Cys Lys Asn Lys Lys Tyr
            805                 810                 815
Tyr Ile Ala Ala Lys Ile Phe Ile Met Met Tyr Thr Tyr Leu Asp Asn
            820                 825                 830
Lys Glu Lys Val Ile Tyr Asp Ile Ile Lys Met Phe Phe Leu His Asn
            835                 840                 845
Lys Leu Tyr Ile Ile Ser Leu Tyr Tyr Thr Lys Leu Lys Tyr Ala Leu
            850                 855                 860
Gln Asn Lys Gln His Gly Cys Phe Lys Lys Arg Lys Lys Ile Lys Lys
865                 870                 875                 880
Asn Lys His Ala Ile Tyr Asn Ile Asn Arg Thr Ile Phe Leu Thr Thr
                885                 890                 895
Asn Asp Leu Ser Met Lys Asp Gln Lys Glu Arg Tyr Tyr Asn Thr Ile
            900                 905                 910
Arg Val Ser Lys Lys Leu Asn Ile Lys Ile Asn Phe Lys Leu Lys Ile
```

-continued

```
                915                 920                 925
Glu Lys Asn Val Asn Lys Leu Val Tyr Ile Lys His Asn Asn Ile
    930                 935                 940
Ile Asn Pro Gln Ile Lys Tyr Ile Thr Leu Ile Lys Met Lys Lys
945                 950                 955                 960
Asn Lys Ile Lys Ser Met Leu Tyr Ile Ile Phe Cys Leu Ile Lys Tyr
                965                 970                 975
Tyr His Asn Ile Lys Asn Phe Ile Ala Gln Glu Lys Asn Glu Asn
            980                 985                 990
Asn Lys Asn Asp Lys Met Ser Asn Asn Asn Asn Asn Asn His Asn
        995                 1000                1005
Asn Asn His Asn Asn Asn Asn His Asn Asn Asn His Asn Asn
    1010                1015                1020
Asn Asn Asn His Asn Asn Asn His Asn Asn His Asn Asn Tyr
    1025                1030                1035
His Asn Asn Tyr His Asn Asn Asn His Lys Ile Ile Arg Pro Phe
    1040                1045                1050
Arg Val Gln Glu Glu Asn Asn Leu Ser Ile Tyr Ile Lys Lys Lys
    1055                1060                1065
Lys Lys Glu Arg His Lys Leu Lys Lys Lys Glu Val Val Val Glu
    1070                1075                1080
Lys Asn Asn Glu Lys Lys Lys Lys Lys Ile Glu Met Tyr Glu Glu
    1085                1090                1095
Asn Asn Lys Asn Tyr Tyr Asn Lys Asp Ile Lys Lys Asn Gln Lys
    1100                1105                1110
Asn Glu Lys Lys Asn Phe Phe Phe Leu Thr Lys Asn Leu Phe Asn
    1115                1120                1125
Lys Phe Leu Val Phe Leu Leu Tyr Ser Asn Val Tyr Glu Phe Lys
    1130                1135                1140
Lys Ile Phe Glu Ser Ser Ser Ser Glu Asp Leu Asn Ile Tyr Met
    1145                1150                1155
Leu Ser Lys His Ile Ile Tyr Leu Leu Lys Asp Asn Phe Ile Phe
    1160                1165                1170
Ile Asn Asn Arg Leu Arg Asn Tyr Tyr Asn Leu Tyr Arg Tyr Thr
    1175                1180                1185
Leu Tyr Tyr Arg Tyr Lys Thr Lys Lys Thr Tyr Asn Asn Asn Tyr
    1190                1195                1200
Phe Leu Tyr Lys Gln Lys Lys Ile Asn Lys Lys Phe Lys Asn Phe
    1205                1210                1215
Lys Ile Asn Asn Ser Asn Thr Asn Thr Asn Asn Asn Arg Asn Ile
    1220                1225                1230
Lys Tyr Asn Asn Lys Asn Tyr Cys Tyr Cys Asn Leu Ile Ser Tyr
    1235                1240                1245
Cys Glu Asn Ile Lys Lys Asn His Asn Asn Leu Lys Asn Ile Asn
    1250                1255                1260
Lys Lys Tyr Tyr His Asn Asn Asn Gln Gln Thr Ser His Ser Phe
    1265                1270                1275
Ser Pro Ser Pro Leu His Ser Thr Ile Tyr Ser Pro Leu Leu Cys
    1280                1285                1290
Cys Phe Cys Ser Ser Pro Phe Phe Ser Ser Ser Ala Glu Asp Tyr
    1295                1300                1305
Pro Ile Arg Ile Thr Ser Ser Asn Ala Glu Lys Lys Ile Leu Leu
    1310                1315                1320
```

```
Asp Ile Leu Leu Tyr Ile Phe Phe His Phe Asp Ile Ile Asn Phe
1325                1330                1335

Lys Asp Ile Asn Cys Phe Phe Lys Asp Cys Leu Lys Asn Asp Ser
1340                1345                1350

Glu Leu Leu Ser Val Asn Lys Lys Ile Leu Asn Phe Lys Glu Lys
1355                1360                1365

Tyr Lys Leu Ile Thr Ser Ile Gly Lys Lys Ile Pro Val Asn Asp
1370                1375                1380

Ile Thr Asn Ile Gln Asn Lys Gln Asp Tyr His Ile Asn Asn Asn
1385                1390                1395

Asn His Thr Asn Cys Asn Ser Glu Ile Ile Asp Pro Lys Lys Phe
1400                1405                1410

Tyr Thr Ile Gln Lys Asn Glu Gln Glu Glu Tyr Ile His Pro Lys
1415                1420                1425

Val Pro Lys Asn Asn His Ile Tyr His Ile Asn Asn Leu Cys Asp
1430                1435                1440

Asn Tyr Lys Lys Asn Asn Ser Leu Ser Leu Gly Tyr His Lys Lys
1445                1450                1455

Asp Asp Asn Asn Asn Asn Ile Tyr Ala Lys Tyr Cys Phe Val Asn
1460                1465                1470

Met Ser Asn Ser Thr Tyr Asp Ile Lys Gln Lys Lys Lys Glu His
1475                1480                1485

Leu Ile Lys Glu Lys Asp Glu Lys Ile Phe Asn Lys Asn Cys Lys
1490                1495                1500

Lys Tyr Gln Lys Asn Val Gln Asp Glu Asn Gly Pro Lys Cys Asn
1505                1510                1515

Asn Asn Ile Arg Lys Ile Glu Lys Lys Lys Ile Asp Lys Tyr Asn
1520                1525                1530

Phe Asn Asn Thr Tyr Ile Ile Gln Glu Ser Lys Asn Asp Leu Leu
1535                1540                1545

Tyr Asn Asn Asn Asn Asn Asn Asn Asn Asn Asn His His His
1550                1555                1560

His Ile Asn Thr Thr Asn Asp Lys Tyr Phe Tyr Asn Leu Asn Lys
1565                1570                1575

His Pro Tyr Asp Tyr Ser His Phe Ser Lys Asp Thr Ser Phe Thr
1580                1585                1590

Thr Leu Asp Tyr Phe Glu Asn Gln Cys Asp Asn Met Lys Lys Leu
1595                1600                1605

Glu Ile Ile Lys Met Leu Leu Asn Ile Lys Ser Glu Lys Val Phe
1610                1615                1620

Leu Tyr Leu Lys Gln Cys Asn Cys Asn Val Val Lys Glu Ile Ile
1625                1630                1635

His Lys His Val Ile Lys Leu Cys Lys Leu Asn Leu Lys Lys Thr
1640                1645                1650

Val Lys Leu Leu Leu Ile Ile Asn Ile Lys Glu Lys Lys Asn Glu
1655                1660                1665

Glu Tyr Leu Phe Tyr Pro His Ile Ile Ile Asn Lys Leu Lys Lys
1670                1675                1680

Lys Pro Tyr Tyr Leu Tyr His Tyr Leu Lys Asn Ile Lys Asp Glu
1685                1690                1695

Tyr Tyr Ile Ser Lys Tyr Ile Asn Val Ile Ile Phe Leu Met Phe
1700                1705                1710

Ile Phe Asp Pro Leu Tyr Leu Glu Lys Phe Ile Asn Lys Tyr Tyr
1715                1720                1725
```

```
Lys Tyr Ile Tyr Phe Lys Lys Ile Leu Phe Phe Ile Ser Phe Phe
    1730            1735                1740

Asn Tyr Leu Tyr Thr Asn Glu Gln Asn Ile Phe Ser Phe Gln Lys
    1745            1750                1755

Lys His Glu His Ile Ser Asn Asn Asn Ser Leu Asp Lys Thr Ile
    1760            1765                1770

Glu Ser Asp Asp Lys Asn Gly Lys Ile Gly Ile Leu Leu Thr Asn
    1775            1780                1785

Ile Glu Asn Thr Asn Leu His Asn Val Glu Cys Val Asp Gln Asn
    1790            1795                1800

Glu Gln Gln Lys Asp Glu Lys Asn Ile Cys Asn Asn Asn Asn Asn
    1805            1810                1815

Asp Cys Asn Asn Asn Asp Cys Asn Asn Asn Asp Cys Asn
    1820            1825                1830

Asn Ser Cys Ile Asp Lys His Ile Ser Val Asn Val Val Glu Gln
    1835            1840                1845

Glu Lys Lys Asn His Ile Leu Ser Tyr Ile Tyr Cys Lys Asn Asn
    1850            1855                1860

Phe Met Met Asn Lys Lys Glu Lys Leu Phe Val Asn Ser Asn Thr
    1865            1870                1875

Lys Lys Ser Met Phe Tyr Phe Lys Asn Lys Tyr Val Ser Leu Ile
    1880            1885                1890

Tyr Lys His Leu Leu Asn Asp Arg Asp Asn Glu Glu Asp Lys Lys
    1895            1900                1905

Glu Leu Phe Arg Ile Phe Asn Ile Val Gln Asn Asn Ser Arg Thr
    1910            1915                1920

Asn Met Asn Lys Ser Met Glu Phe Phe Leu His Ile Lys Ala Leu
    1925            1930                1935

Val Tyr Leu Lys Phe Gly Tyr Ile Asn Arg Ala Leu Gln Ile Phe
    1940            1945                1950

Leu Lys Leu Asn Asn Tyr Leu Lys Ile Phe Tyr Ile Met Ile His
    1955            1960                1965

His Asn Val Lys Ile Tyr Asp Glu Arg Ile Lys Arg Arg Met Lys
    1970            1975                1980

Tyr Tyr Ile Gly Ser Ser Asp Tyr Phe Asn Asn Ser Ile Lys Lys
    1985            1990                1995

Asp Lys Tyr Gly Val Cys Lys Ile Ser Asp Ser Lys Asn Lys Thr
    2000            2005                2010

Phe Asn Asn Asn Ile Ile Asn Ile Val Asp Ile Val Asn Val Asp
    2015            2020                2025

Asn Val Asp Asn Asp Asp Asp Asn Asn Asn Ile Tyr Asn Thr
    2030            2035                2040

Tyr Asn Asn Tyr Asn Asn Ser Tyr Tyr His Asn Tyr His Asp Val
    2045            2050                2055

Arg Asn Lys Leu Asn Asn Ser Asp Lys Thr Ile Leu Ile Glu Lys
    2060            2065                2070

Tyr Tyr Glu Asp Asn Lys Asn Asp Phe Phe Lys Asn Asn Met Asn
    2075            2080                2085

Tyr Asp Asp Ile Leu Tyr Asn Arg Arg Glu Ala Asn Asn Tyr Tyr
    2090            2095                2100

Asp Asp Thr Leu Ile Phe Lys Asn Lys Ile Asn Glu His Lys Lys
    2105            2110                2115

Phe Val Val Asn Lys Lys Tyr Lys Ile Ile Lys Cys Ile Asp Asn
```

|   |   |   |   |   | 2120 |   |   |   | 2125 |   |   |   | 2130 |   |

Thr Tyr Thr Phe Lys Val Asn Lys Tyr Leu Ser Lys Lys Lys Ile
2135                     2140                    2145

Tyr Lys Lys Leu Phe Met Leu Tyr His Lys Ile Val Ile Tyr Lys
2150                     2155                    2160

His Ile Met Asp Leu Lys Asn Lys Asn Lys Ile Phe Asn Thr
2165                     2170                    2175

Asn Asp Asp Ile Ser Phe Asn Asn Ile Asn Asp Thr Leu Glu Lys
2180                     2185                    2190

Lys Glu Asn Lys Ser Cys Asn Ser Ile Asp Tyr Ile Ile Glu Lys
2195                     2200                    2205

Gly Ile His Asn Asn Ser Glu Tyr Ser Phe Tyr Asp Gln Gln Ile
2210                     2215                    2220

Met Leu Asp Leu Tyr Asn His Gln Gln Tyr Met Ile Asn Asn Ile
2225                     2230                    2235

Lys Gln Glu Lys Asn Lys Lys Ile Lys Asn Tyr Asn His Ile Ile
2240                     2245                    2250

Ser Glu Ile Lys Arg Glu Lys His Ile Asn Ser Asn Leu Leu Cys
2255                     2260                    2265

Lys Lys Asn Arg Lys Tyr Thr His Lys Lys Tyr Asn Met Leu
2270                     2275                    2280

Tyr Leu Asn Asn Asn Lys Phe Ile Lys Asn Lys Ile His Lys Tyr
2285                     2290                    2295

Asn Ser Asp Thr Asn Val Leu Gln Asn Tyr Leu Asn Asn Ile
2300                     2305                    2310

Asn His His Met Asn Tyr Phe Thr Leu Thr Tyr Leu Leu Glu Gln
2315                     2320                    2325

Cys Phe Tyr Lys Asn Asp Leu Cys Glu Asn Tyr Asn Asn Ile Leu
2330                     2335                    2340

Leu Asn Asn Lys Lys Ser Ile Phe Asn Phe Leu Asn Asn Met Lys
2345                     2350                    2355

Lys Lys Gly Tyr Thr Ile Tyr Asn Gly His Met Lys Lys Asp Ile
2360                     2365                    2370

Lys Lys Asn Glu Val Asn Leu Leu Asp Ile Asn Asp Phe Tyr Phe
2375                     2380                    2385

Leu Asn Asn Thr Asn Asn Lys Thr Gln Ile Asn Lys Lys Asn Ser
2390                     2395                    2400

Asp Asp Ser Phe Tyr Phe Asp Glu Tyr Asn Asn Asn Lys Gln Thr
2405                     2410                    2415

Gln Gln Asn His Lys His Lys Tyr His Ile Gln Lys Arg Lys Ile
2420                     2425                    2430

Ser Ser Asn Val Tyr Leu Tyr Glu Asp Ile Asn Asn Asn Gln Tyr
2435                     2440                    2445

Ile Ser Asn Ile Ser Ser Phe Cys Ser Leu Cys Leu Asn Asn Val
2450                     2455                    2460

Tyr Ile Asn Pro Asn Thr Asn Lys Asp Glu Ala Asn Lys Lys Asn
2465                     2470                    2475

Thr Leu Val Phe Phe Phe Cys Asn His Leu Tyr His Leu Lys Cys
2480                     2485                    2490

Leu His Asn Gly Glu Phe Leu Cys Lys Ser Cys Glu Ser Trp
2495                     2500                    2505

<210> SEQ ID NO 9
<211> LENGTH: 332

<212> TYPE: PRT
<213> ORGANISM: Plasmodium falciparum

<400> SEQUENCE: 9

```
Met Trp Phe Cys Asn Lys Phe Asn Asp Asn Thr Thr Lys Gly Leu Leu
1               5                   10                  15

Asp Ser Asn Asn Val Gln Ser Lys Tyr Cys Thr Ile Tyr Ser Phe Asp
                20                  25                  30

Asp Glu Glu Asn Asn Thr Lys Arg Lys Asn Gln Phe Ala Ser Phe Ser
            35                  40                  45

Lys Leu Cys Leu Lys Leu Cys Ile Leu Gly Ile Ile Val Ile Val Asn
        50                  55                  60

Val Cys Cys Ser Phe Glu Ser Asn Glu Ile Ser Lys Val Asn Leu Ile
65                  70                  75                  80

Lys Lys Glu Tyr Ser Arg Ile Leu Ser Glu Thr Glu Ala Leu Glu Asn
                85                  90                  95

Leu Lys Glu Glu Ser Lys Asn Arg Lys Asp Asp Glu Glu Val Ser
            100                 105                 110

Leu Phe Asp Gly Ser Asp Met Gly Arg Thr Tyr Asp Asn Asp Thr
        115                 120                 125

Cys Tyr Gln Ser Arg Tyr Asn Arg Ser Ser Ile Gly Asp Leu Ile Gln
130                 135                 140

Val Ile Lys Ser Thr Phe Gly Gly Glu Asp His Leu Phe Gln Thr
145                 150                 155                 160

Cys Pro Asp Ile Phe Asp Glu Leu Val Lys Arg Ser Thr Trp Glu Arg
                165                 170                 175

Leu Glu Leu Asp Leu Tyr Glu Thr Glu Ile Ser Asp Tyr Leu Thr Val
            180                 185                 190

Thr Tyr Asp Leu Ser Leu Asn Glu Lys Ile Leu Thr Leu Ser Arg Leu
        195                 200                 205

Ser Asn Glu Glu Asp Leu Tyr Asn Leu Trp Ser Glu Ile Met Arg Asn
210                 215                 220

Glu Glu Arg Lys Phe Ser Phe Leu Arg Tyr His Leu Tyr Asn Tyr Tyr
225                 230                 235                 240

Tyr Ser Leu Lys Asn Arg Ser Arg Val Ser Arg Glu Tyr Ser Glu Lys
                245                 250                 255

Ile Trp Asn Glu Cys Glu Thr Leu Lys Ser Leu His Glu Ser His
            260                 265                 270

Glu Ser Ser Ile Phe Asp Leu Phe His Lys Trp Ile Asn Gly Ser Ile
        275                 280                 285

His Glu Leu Ser Glu Phe Lys Val Leu Val Ser Ala Gly Arg Tyr Ser
290                 295                 300

Trp Arg Asn Leu Leu Lys Thr Gly Glu Arg Glu Cys Lys Lys Phe Met
305                 310                 315                 320

Ile Lys His Tyr Lys Gly Lys Thr Ala Leu Arg Ile
                325                 330
```

<210> SEQ ID NO 10
<211> LENGTH: 106
<212> TYPE: PRT
<213> ORGANISM: Plasmodium falciparum

<400> SEQUENCE: 10

```
Met Ser Arg Arg Asn Ile Arg Leu Pro Ala Glu Val Ser Arg Ile Leu
1               5                   10                  15

Tyr Val Arg Asn Leu Pro Tyr Lys Ile Ser Ala Asp Glu Leu Tyr Asp
```

```
                20                  25                  30
Ile Phe Gly Lys Tyr Gly Thr Val Arg Gln Ile Arg Lys Gly Asn Ala
             35                  40                  45

Glu Gly Thr Lys Gly Thr Ser Phe Val Val Tyr Asp Asp Ile Tyr Asp
         50                  55                  60

Ala Lys Asn Ala Leu Asp His Leu Ser Gly Phe Asn Val Ala Gly Arg
65                  70                  75                  80

Tyr Leu Val Val Leu Tyr Tyr Asp Pro Val Lys Ala Gln Lys Lys Lys
                 85                  90                  95

Glu Ile Gln Glu Lys Leu Lys Asn Glu Lys
            100                 105

<210> SEQ ID NO 11
<211> LENGTH: 2539
<212> TYPE: PRT
<213> ORGANISM: Plasmodium falciparum

<400> SEQUENCE: 11

Met Asn Asn Leu Asn Asn Gln Thr Cys Asn Lys Leu Ile Asn Asn Tyr
1               5                   10                  15

Tyr Asn Lys Lys Glu Asn Asn Asp Lys Asn Asp His Gly Asn Ser
            20                  25                  30

His Pro Gln Gly Asn Asn His Gln Asn Lys Gln Asn Asn Ile Leu
         35                  40                  45

Ile Asn Arg Asn Thr Lys Glu Thr Lys Pro Leu Lys Gly Ile His Thr
         50                  55                  60

Arg Leu Ser Thr Val Asn Val Gly Tyr Gly Ile Lys Asp Ala Ile Gly
65                  70                  75                  80

Gln Ile Phe Lys Tyr Lys His Lys Tyr Asn Glu Tyr Leu Asn Tyr Gly
                 85                  90                  95

Ile Leu Cys Glu Leu Arg Ile Leu Tyr Glu Leu Asn Ile Ile Asp Leu
            100                 105                 110

Ile Tyr Leu Leu Glu Val Glu Glu Ile Met Arg Arg Tyr Asn Met Lys
         115                 120                 125

Tyr Glu Ile Asn Glu Thr Tyr Leu Ser Leu His Ile Lys Asp Val Ile
130                 135                 140

His Asn Leu Tyr Val Ser Asn Tyr Ile Val Tyr Leu Asn Tyr Leu Val
145                 150                 155                 160

Leu Phe Asn Pro Val His Ile Ser Lys Ile Lys Lys Asn Ile Leu Ile
                165                 170                 175

Gln Ile Pro Met Asp Ile Ile Leu Lys Val Leu Cys Pro Asn Val Phe
            180                 185                 190

Ile Ser Ser Tyr Lys Lys Thr Asn Ile Ile Asn Ile Asn Glu Asn Ser
         195                 200                 205

Ile Tyr Leu Ile Asp Ser Ser Asp Lys Glu Asn Asp Arg Pro Met Ser
210                 215                 220

Ser Lys Arg Lys Arg Glu Ser Lys Tyr Lys Lys Val Glu Lys Lys
225                 230                 235                 240

Asn Ser Lys Glu Lys Cys Asp Lys Lys Ile Thr Asn Glu Val Thr Ile
                245                 250                 255

Thr Asn Thr Glu Leu Asn Asn Glu Gly Ile Lys Glu Glu Thr Lys Glu
            260                 265                 270

Leu Ile Asn Glu Ala Asn Asn Pro Ser Ile Lys Lys Asp Thr Thr Glu
         275                 280                 285

Phe Phe Leu Glu Thr Asn Met Lys Arg Lys Asn Ile Leu Leu Pro His
```

```
                290                 295                 300
Thr Gly Asn Lys Ser Glu Ser Ile Arg Val Ile Tyr Ala Ser Cys Leu
305                 310                 315                 320

Ser Ser Asn Lys Ile Tyr Leu Arg Asn Ile Asn Met Cys Tyr Asp Val
                325                 330                 335

Val Val Phe Ile Lys Ile Leu Arg Asp Leu His Phe Pro Ile Met Leu
                340                 345                 350

Lys Gly Arg Lys Ile Asp Lys Tyr Ile Asp Asn Ile Ile Asn Ile Gln
                355                 360                 365

Lys Lys Val Tyr Ser Glu Glu Met Glu Lys Ile Asp Asp Glu Lys Arg
370                 375                 380

Phe Thr Ser Val Glu Ser Ile Asn Asn Ser Phe Asn Ile Asn Asn Met
385                 390                 395                 400

Glu Asn Ile Phe Arg Ile Gln Asn Val Ser Tyr Leu Glu Arg Val Ala
                405                 410                 415

Ile Leu Glu Cys Lys Lys Tyr Cys Lys Gly Lys Lys Tyr Lys Tyr
                420                 425                 430

Asn Asn Phe Asn Lys Asn His Arg Ile Lys Lys Lys Cys Asn Val
435                 440                 445

Cys Lys Cys Thr Glu Gln Glu Lys Lys Asn Leu Gly Lys Ile Ser Lys
450                 455                 460

Glu Tyr Met Thr Ala Cys Ile Glu His Ser Leu Ser Tyr Phe Phe
465                 470                 475                 480

Leu Lys Lys Glu Lys Asn Val Ile Ile Glu Gly Asn Val Asp Lys
                485                 490                 495

Ser Asp Thr Leu Phe Lys Asn Phe Val Phe Lys Lys Val Ile Leu
                500                 505                 510

Asn Val Tyr Asn Cys Gly Thr Val Cys Arg Phe Ile Leu Pro Leu Leu
                515                 520                 525

Cys Leu Tyr Ile Cys Lys Gln Asn Ile Lys Ala Gln Glu Glu Asn Lys
530                 535                 540

Thr Lys Ile Lys Tyr Ile Ile Leu Lys Gly Cys Lys Gln Met Glu Asn
545                 550                 555                 560

Val Arg Ile Ile His Pro Leu Val Asn Val Leu Arg Lys Cys Phe Lys
                565                 570                 575

Tyr Ile Lys Ile Lys Tyr Leu Lys Lys His Tyr Leu Pro Ile Ser
                580                 585                 590

Ile Ser Ile Lys Lys His Ile Leu Asn Ile Thr His His Asp Ile Phe
                595                 600                 605

Leu Thr Lys Gln Ile Tyr Val Asp Asn Tyr Tyr Ser Ser Gln Phe Ile
610                 615                 620

Ser Ser Leu Leu Leu Ile Ser Pro Phe Ser Lys Asn Asn Thr Lys Leu
625                 630                 635                 640

Cys Leu Asn Tyr Lys His Ser Tyr Lys Thr Lys Asn Met Ile Asn Asn
                645                 650                 655

Asp Tyr Thr Asn Lys Tyr Ile Ile Asn Lys Gln Lys Asn Ile Phe Tyr
                660                 665                 670

Asn Asn Ile Lys Asn Asn Ile Lys Tyr Lys Ile Arg Tyr Leu Tyr Asn
                675                 680                 685

Ile Ser His Gln Glu Lys Lys Lys Lys Lys Leu Thr Phe Phe Lys
                690                 695                 700

Lys Tyr Met Leu Lys Lys Glu Cys Leu Leu Lys Asn Ser Ile Leu Asn
705                 710                 715                 720
```

```
Lys Leu Ile Ile Pro His Asp Cys Lys Lys Gly Thr Met Ile Leu Asn
            725                 730                 735

Gln Asn Ile His Leu Asn Glu Glu Asn Lys Asn Asp Ile Thr Thr Lys
        740                 745                 750

Asn Asn Asn Asn Asn Asn Asn Asn Asn Asn Asn Asn Asn Asn Asn Lys
                755                 760                 765

Val Asn Asn Gln Ile Cys Val Gln His Lys Leu Pro Cys Asp Tyr Thr
770                 775                 780

Phe Tyr Gln Asn Ile Lys Lys Glu Asp Tyr Lys Gln Cys Gly Leu Phe
785                 790                 795                 800

Asn Thr Thr Ser Lys Ala Phe Ile Asp Met Thr Leu Tyr Val Met Arg
            805                 810                 815

Thr Trp Gly Ile His Ile Lys Val Asn His Lys Gly Ile Tyr Tyr Val
        820                 825                 830

Gln Lys Lys Glu Met Tyr Gln Leu Tyr Asp Asp Asn Asn Asn Asn
            835                 840                 845

Asn Asn Asn Asn Lys Ser Asp Ile Cys Leu Asn Arg Val Asn Pro Asn
850                 855                 860

Lys Cys Ser Ser Glu Lys Lys Thr Asn Pro Asn Ser Ser Ile
865                 870                 875                 880

Leu Lys Lys Asp Lys Glu Lys Lys Asn Gln Met Asp Gly Lys Ile
            885                 890                 895

Val Thr Asn Leu Val Lys Gly Asp Asn Lys Glu Glu Gly Asn Asn
        900                 905                 910

Asn Ile Ile Lys Asn Asp Asp Ser Ala Ser Lys Gly Thr Asn Glu His
            915                 920                 925

Met Met Gln Arg Ile Asn Asp Ala Glu Thr Thr Gln Asn Asn Thr Leu
930                 935                 940

His Lys Glu Asn Lys Leu Cys Thr Thr Lys Asp Gln Asn Lys Ile His
945                 950                 955                 960

Thr Lys Ile Asn Ser Lys Glu Asn Glu Lys Val Lys Lys Tyr Tyr Tyr
            965                 970                 975

Tyr His Ile Asn Asn Asp Leu Gly Leu Tyr Phe Tyr Phe Leu Val Gly
        980                 985                 990

Phe Ile Ile Lys Lys Lys Asn Cys Thr Ile Ser Leu Lys Leu Asn Ile
995                 1000                1005

Asn Asn Leu Asn Val Lys Tyr Lys Gly Asn Asn Ile Tyr Lys Ile
    1010                1015                1020

Lys Thr Val Met Tyr Gln Lys Asp Ile Tyr Asn Tyr Tyr Leu Leu
    1025                1030                1035

Asn Ile Leu Leu Leu Val Gly Val Lys Ile Tyr Ile Arg Gln His
    1040                1045                1050

Asn Lys Leu Asn Lys Glu Ser Glu Tyr Asn Val Asn Ser Gln Asn
    1055                1060                1065

Leu Ile Gly Ser Lys Ser Lys Ser Ser Lys Ile Tyr Met Val His
    1070                1075                1080

Phe Ile Thr Ser Glu Ile Ser Phe Asn Lys Lys Ile Leu Arg
    1085                1090                1095

Pro Phe Tyr Lys Ile Gln Lys Lys Ile Asn Asn Lys Tyr Lys Arg
    1100                1105                1110

Ile Ile Met Asn Gln Ser Ala His Ile Asn Ile Lys Glu Ser Lys
    1115                1120                1125

Asn Asn Ile Ile Ser Asn Asn Val Glu Glu Lys Asn Ser Val Thr
    1130                1135                1140
```

-continued

```
Ser Asn Ile Val Ser Asn Ile Ser Ser Asn Asn Ile Ser Pro Tyr
    1145                1150                1155

Tyr Lys Ser Ile Lys Glu Asn Asn Lys Met Lys Lys Thr Asn Asn
    1160                1165                1170

Cys Ile Glu His Ile Leu Asn Asn Tyr Lys Ile Lys Tyr Asn Ile
    1175                1180                1185

Tyr Glu Lys Ile Tyr Ile Lys Tyr Glu Thr Asn Asn Asn His Met
    1190                1195                1200

Leu Ser Phe Lys Ile Val Ile Asp Ala Glu Ser Phe Ser Asp Asp
    1205                1210                1215

Phe Phe Ser Ile Cys Ile Leu Phe Ser His Phe Ile Leu Ser Asn
    1220                1225                1230

Ile Asn Glu Asn Ile Ile Phe Lys Ile Lys Asn Ile His Asn Gln
    1235                1240                1245

Asn Ile Lys Glu Ser Thr Arg Ile Tyr His Val Val Phe Ile Leu
    1250                1255                1260

Lys Leu Phe Phe His Asn Leu Leu Phe Ile Ser Cys Thr Asn Asn
    1265                1270                1275

Ser Ile Tyr Ile Thr Lys Met Leu His Pro Leu Gln Asn Ile Gln
    1280                1285                1290

Phe Tyr Arg Tyr Lys Lys Asn Ile Arg Thr Asn Asn Gln Lys Ile
    1295                1300                1305

Tyr Asn Thr Asn Tyr Ile His Asn Lys Tyr Glu Lys Ile Gln Asn
    1310                1315                1320

Phe Val Asn Asn Ser Lys Tyr Val Ile Asn Asp Met Gln Ser Leu
    1325                1330                1335

Tyr Leu Tyr Val Asp Thr Gln Asn Asp His Arg Ile Ile Phe Met
    1340                1345                1350

Ser Thr Ile Leu Ser Leu Ile Phe Lys Asn Ile Ile Ile Pro Lys
    1355                1360                1365

Cys Asp Asn Val His Lys Ser Phe Pro Leu Phe Phe His Tyr Ala
    1370                1375                1380

Lys Lys Tyr Leu His Ile Tyr Val Gln Asn Gly Ser Asn Gln Phe
    1385                1390                1395

Ile Asn Thr Tyr Asn Phe Gln Asp Val Asn Asn Ile Asn Leu Leu
    1400                1405                1410

His Cys Thr Lys Lys Lys Arg Pro Gln Arg Gly Ser Thr Pro Asp
    1415                1420                1425

Glu Lys Tyr Lys Gly Gly Glu Ile Lys Gly Asn Asp Ile Ile Lys
    1430                1435                1440

Glu Ser Asp Ile Ile Lys Cys Asn Asp Ile Ile Lys Glu Ser Asp
    1445                1450                1455

Val Val Asn Lys Asn Glu Ile Val Glu Asn Met Asn Ile Ile Ile
    1460                1465                1470

Glu Lys Asp Glu Ile Lys Thr Asp Lys Tyr Thr Glu Pro Ile Lys
    1475                1480                1485

Tyr Asp Asn Thr Ser Asp Ala Lys Ser Ile Ser Thr Ser Thr Ser
    1490                1495                1500

Val Leu Ser Ser Glu Ser Ser Asn Glu Leu Ser Asp Cys Cys Met
    1505                1510                1515

Asn Lys Leu Thr Lys Glu Asn Met Glu Met Asn Asn Val Ile Ile
    1520                1525                1530

Thr Lys Asn Asn Asn Asn Asp Asn Asn Asn Glu Asn Asn Glu Asn
```

```
                1535                1540                1545

Asn Glu Asn Asn Asp Asn Asn Glu Asn Glu Asn Asn Asp Asn
    1550                1555                1560

Asn Asn Asn Asn Asn Asn Asn Asn Val Glu Val Tyr Lys Pro
    1565                1570                1575

Asn Tyr Lys Ile Asn Gly Leu Gln Asn Ile Ile Asn Ser Cys Leu
    1580                1585                1590

Asn Phe Ile Cys Ser Lys Arg Lys Asn Ile Lys Asn Lys Ile Lys
    1595                1600                1605

Asn Lys Ile Ile Lys His Lys Lys Asn Lys Ile Ile Asn His Lys
    1610                1615                1620

Lys Lys Lys Lys Asn Cys Asn Thr Arg His Arg Gly Asn Thr Gln
    1625                1630                1635

Ile Asn Asn Lys Leu Val Leu Ile Asn Ile Thr Pro Tyr Ile Leu
    1640                1645                1650

Arg Tyr Pro Asn Asn Asn Lys Ser Ser Lys Lys Leu Ser Cys Thr
    1655                1660                1665

Lys Glu Ile Lys Lys Lys Thr Phe Pro Arg Ile Cys Glu Ser Tyr
    1670                1675                1680

Asp Ile Lys Lys Asn Ile Asp Ile His Asn Val Asn Lys Lys Asn
    1685                1690                1695

Tyr Lys Lys Ile Asp Asp Thr Leu Asn Val His Lys Glu Glu Ile
    1700                1705                1710

Asp Thr Ser Lys Gln His Thr Asp Glu Lys Ile Cys Lys Lys Ile
    1715                1720                1725

Gln Lys Tyr Leu Tyr Leu Asp Val Lys Arg Lys Arg Tyr Ile Ser
    1730                1735                1740

Leu Tyr Met Tyr Asn Lys Lys Lys Gly Lys Asp Thr Asn Asn Lys
    1745                1750                1755

Asn Ile Gln Lys Lys Lys Lys Glu Glu Glu Lys Lys Gln Ile
    1760                1765                1770

Ser Tyr Asn Ile Ser Ser Lys His Asn Ser Ile Leu Asn Asn Arg
    1775                1780                1785

Met Lys Tyr Asn Asn Ile Ile Asp Met Tyr Lys Arg Asn Asn Phe
    1790                1795                1800

Ile Tyr Lys Asp Asp Asn Tyr Lys Arg Ile Tyr Thr Tyr Asp Glu
    1805                1810                1815

Ile Leu Glu Asn Asp Ile Asn Ile Ser Tyr Leu Ile Lys Gln Ile
    1820                1825                1830

Asn Ile Leu Asn Val Thr Ile Ile Cys Gly Met Arg Asn Val Gly
    1835                1840                1845

Lys Thr Phe Leu Ser Lys Lys Ile Glu Asn Asn Ile Ile Ile Asp
    1850                1855                1860

Ile Asp Glu Tyr Ile Leu Lys Asp Glu Ile Lys Phe Asp Lys Leu
    1865                1870                1875

Ser Ile Ser Asp Phe Arg Tyr Tyr Glu Tyr Val Thr Phe Ile Ser
    1880                1885                1890

Ser Leu Tyr Leu Ala Phe Tyr Ile Leu Thr Phe Asp Arg Asn Leu
    1895                1900                1905

Ser Ala Pro Lys Asp Gln Thr Gly Ala Thr Ile Lys His Val Asp
    1910                1915                1920

Ile Arg Asp Glu Lys Ile Asn Ser Lys Asn Gln Asn Lys Gln Thr
    1925                1930                1935
```

```
Glu Tyr Asp Asn Asp Ile Asn Asp Asn Asn Tyr Asn Asn Ser
    1940            1945            1950

Asp Asn His Asn Leu Leu His Asn Asn Lys Asp Asn Gln His Thr
    1955            1960            1965

Ser Thr Lys Lys Lys Ile Gln Lys Lys Val Ser Phe Ser Asp Val
    1970            1975            1980

Cys Glu Ile Tyr Val Asp Gly Pro Asn Phe Glu Asn Lys Asn Tyr
    1985            1990            1995

Asp Asp Asn Ile Phe Tyr Thr Tyr Thr Asn Lys Gly Ile Thr Phe
    2000            2005            2010

Tyr Asn Lys Lys Ile Asn Asp Leu Phe Cys Lys Leu Arg Lys Lys
    2015            2020            2025

Cys Ile Gln Glu Lys Gln Asn Gly Glu His Gln Met Thr Asn Val
    2030            2035            2040

Thr Ile Val Leu Gly Gly Gly Ile Ile Glu Phe Asp Lys Ser Lys
    2045            2050            2055

Glu Val Leu Lys Lys Leu Lys Asn Thr Ile Leu Ile Lys Arg Asp
    2060            2065            2070

Ile Asp Glu Ile Tyr Asp Ile Cys Ile Asn Asp Asn Ile Lys Pro
    2075            2080            2085

Lys Leu Asn Gly Asn Ile Lys Asp Ile Ile His Arg Arg Thr Ile
    2090            2095            2100

Leu Tyr Asp Lys Leu Ser Asn Ala Phe His Phe Ile Ile Pro Ser
    2105            2110            2115

Glu Asn Met Ile Asn Lys Tyr Ile Arg His Ser Glu Tyr Asn Lys
    2120            2125            2130

Tyr Ile Asn Arg Asn Glu Leu Ile Val His Ser Phe Leu Arg Phe
    2135            2140            2145

Phe Asn Tyr Pro Phe Phe Lys Pro Leu Ile Gly Asp Ile Ile
    2150            2155            2160

Thr Asn Tyr Lys Ile Asp Lys Asn Glu Lys Asn Asp Glu Lys Asn
    2165            2170            2175

Asp Glu Lys Asn Asp Glu Lys Asn Asn Glu Lys Asn Asp Glu Lys
    2180            2185            2190

Asn Gly Asp Asn Asn Asp Asp Asn Asn Asp Asn Asn Glu Asp
    2195            2200            2205

Glu Asn Asn Lys Lys Lys Lys Lys Lys Lys Asn Asp Cys Asn
    2210            2215            2220

His Asn His Ile Asn Asn Tyr Tyr Arg Val Leu Tyr Ile Asn Leu
    2225            2230            2235

Asn Asn Leu Arg His Phe Pro Tyr Met Asn Leu Leu Lys Glu Asp
    2240            2245            2250

Tyr Asp Ile Ile His Ile Lys Ile Tyr Lys Tyr Glu Gln Ile Lys
    2255            2260            2265

Leu Leu Glu Leu Ala Ile Phe Leu Ile Arg Ser Cys Thr Cys Lys
    2270            2275            2280

Glu Tyr Lys Ile Ile Val Lys Leu Tyr Pro Gln Tyr Phe Phe Thr
    2285            2290            2295

Tyr Gln Glu Tyr Ile Ile Lys Lys Lys His Lys Lys Lys Ser
    2300            2305            2310

Leu Lys Asn Lys Lys Ser Asn Lys Lys Tyr Glu Phe Asp Asn
    2315            2320            2325

Tyr Ile Cys Glu Asn Ile Leu His Ile Phe Tyr Lys Tyr Lys Ile
    2330            2335            2340
```

```
Asn Ile Phe Glu Leu Asp Asn His Phe Leu Lys Val Ala Lys Lys
    2345                2350                2355

Ile Leu Ser Tyr Lys Lys Glu Asn Ile Phe Phe Ile Ile Ser Lys
    2360                2365                2370

Lys Glu Lys Ile Ile Asn Lys Leu Lys Ile Gln Ser Asp Leu Tyr
    2375                2380                2385

Lys Leu Asn Ile Trp Gln Ala Asp Ile Ile Lys Leu Ser Ser Ser
    2390                2395                2400

Asn Gln Ile Ser Leu Thr Glu Cys Asn Leu Leu Glu Asn Ile Leu
    2405                2410                2415

Tyr Asp Phe Tyr Val Asp Thr Ile Asn Gln Pro Ala Asn Thr Leu
    2420                2425                2430

Leu Phe Glu Lys Arg Leu His Asn Asn Asp Lys Asn Glu Gln Thr
    2435                2440                2445

His Ile Leu Tyr Tyr Asn Ala Thr Asp Lys Cys Leu Phe Ser Phe
    2450                2455                2460

Leu Tyr Asn Asn Ile Thr His Leu Ser Tyr Asn Lys Arg Phe Leu
    2465                2470                2475

Pro Ile Ile Lys Lys Asn Lys Met Tyr Gly Tyr Leu Ser Asn Ile
    2480                2485                2490

Lys Glu Asp His Thr Asn Gln Asn Ile Gln Ser Glu Ser Tyr Tyr
    2495                2500                2505

Thr Gln Ser Ser Tyr Tyr Asn Arg Val Lys Pro Ile Leu Phe Tyr
    2510                2515                2520

Thr Ile Ile Gln Asn Val Lys Glu Lys Asn Asp His Gln Gln Thr
    2525                2530                2535

Asn

<210> SEQ ID NO 12
<211> LENGTH: 1192
<212> TYPE: PRT
<213> ORGANISM: Plasmodium falciparum

<400> SEQUENCE: 12

Met Leu Lys Lys Tyr Ile Ile Leu Ile Tyr Ile Gly Val Ile Leu Asn
1               5                   10                  15

Phe Ile Thr Lys Asn Asn Asn Val Val Ser Val Pro Glu Pro Phe Leu
                20                  25                  30

Ser Gln Asn Lys Asp Ser Phe Glu Glu Lys Lys Tyr Thr Tyr Gly Asp
            35                  40                  45

Asn Leu Gln Leu Gly Ala Ser Thr Ile Asn Thr Pro Lys Thr Gln Ser
        50                  55                  60

Gln Glu Asn Lys Asp Ile Asn Lys Glu Thr Lys Asn Thr Ile Ile Lys
65                  70                  75                  80

Lys Thr Asn Asn Phe Pro Ser Thr Leu Asn Glu Lys Phe Pro His Lys
                85                  90                  95

Ile Gln Leu Thr Asn Lys Glu Asn Lys Glu Asp Glu Gln Asn Lys Glu
            100                 105                 110

Asn Lys Lys Asp Glu Gln Asn Lys Glu Asp Glu Gln Asn Lys Gln Asn
        115                 120                 125

Lys Glu Asp Glu Gln Asn Lys Gln Asn Lys Asp Lys Lys Asn Ile Val
    130                 135                 140

Ser Asn Lys Leu Ser Gly Asn Asn Glu Gln Gln Asn Asn Ser Ile Pro
145                 150                 155                 160
```

-continued

```
Lys Ser Ile Gln Lys Pro Glu Asn Cys Val Lys Gln Ser Asn Gln
                165                 170                 175
Phe Pro Arg Ser Tyr Pro Glu Phe Phe Glu Ala Asn Phe Gly Pro Ile
            180                 185                 190
Asp Glu Leu Met Asp Glu Thr Asp Tyr Ser Ser Asp Asp Leu Glu Asp
            195                 200                 205
Gln Leu Asn Tyr Gly Tyr Arg Gly Ile Glu His Asp Ile Asp Glu Thr
        210                 215                 220
Asp Tyr Tyr Ile Gly Ser Ile Leu Gly Tyr Ser Asp Phe Met Asn Lys
225                 230                 235                 240
Met Lys Tyr Gln Asn Thr Gln Ile Asp Asn Lys Gly Lys Lys Thr
                245                 250                 255
Thr Asn Thr Met Glu Lys Asn Lys Lys Asn Arg Asp Lys Lys His Ser
            260                 265                 270
Lys Lys Arg Lys Thr Lys Gln Asn Tyr Lys Tyr Lys Lys Glu Asn Gln
        275                 280                 285
Asn Ile Glu Asn His Ile Pro Gln Ser Lys Tyr Lys Gln Glu Arg Ile
    290                 295                 300
Glu Ile Leu Asp Asp Asn Gly Lys Glu Leu Lys Ser His Lys Asn Ile
305                 310                 315                 320
Lys Glu Glu Lys Gly Gly Ile Glu Lys Thr Asp Thr Thr Asn Ile Ala
                325                 330                 335
Asp Ile Lys Ile Lys Lys Glu Arg Glu Thr Lys Asp Glu Lys Glu
            340                 345                 350
Lys Asn Ile Gln Gln Leu Val Lys Asp Val Gln Leu Ile Lys Val Gly
        355                 360                 365
Glu Glu Thr Lys Asp Asp Glu Lys Glu Asp Lys Glu Gly Thr Asp Asp
    370                 375                 380
Glu Glu Asp Thr Asp Asp Glu Asp Thr Asp Glu Glu Asp Thr
385                 390                 395                 400
Asp Asp Glu Glu Asp Thr Ser Asp Glu Glu Thr Thr Gly Asp Gln Glu
                405                 410                 415
Asn Lys Glu Glu Thr Glu Val Asp Glu Lys Lys Thr Glu Lys Ala Glu
            420                 425                 430
Glu Glu Leu Glu Glu Asp Lys Glu Glu Ser Glu Lys Asp Lys Glu Glu
        435                 440                 445
Ser Glu Lys Asp Lys Glu Glu Ser Glu Lys Asp Lys Glu Glu Ser Glu
    450                 455                 460
Lys Asp Lys Glu Lys Thr Glu Glu Asp Glu Glu Lys Thr Glu Asp Glu
465                 470                 475                 480
Lys Gly Thr Glu Val Tyr Lys Lys Glu Thr Asp Val Asp Glu Lys Lys
                485                 490                 495
Glu Lys Gly Glu Tyr Gly Glu Gly Thr Asp Asp Glu Asp Lys Glu
            500                 505                 510
Lys Glu Glu Asp Asp Glu Glu Thr Lys Val Glu Glu Lys Lys Thr Glu
        515                 520                 525
Lys Asp Glu Glu Gly Thr Asp Tyr Glu Glu Asp Thr Asp Asp Ser Asp
    530                 535                 540
Lys Asp Glu Glu Thr Lys Val Glu Glu Lys Lys Thr Glu Arg Asp Glu
545                 550                 555                 560
Glu Glu Thr Glu Glu Asp Glu Lys Glu Thr Glu Val Glu Lys Lys Lys
                565                 570                 575
Thr Glu Lys Asp Glu Glu Gly Thr Asp Tyr Glu Glu Asp Thr Asp Asp
            580                 585                 590
```

```
Ser Asp Lys Asp Val Glu Thr Glu Val Glu Glu Thr Asp Ala Glu Asp
            595                 600                 605

Lys Glu Glu Asn Glu Glu Gly Thr Asp Asp Glu Glu Asp Lys Val Glu
            610                 615                 620

Glu Thr Asp Leu Asp Asp Gln Glu Glu Asp Gly Glu Glu Asp Lys Glu
625                 630                 635                 640

Asp Asp Lys Glu Lys Asp Lys Glu Asp Lys Glu Asp Lys Glu
                645                 650                 655

Lys Asp Lys Glu Asp Asp Lys Glu Lys Tyr Lys Glu Asp Asp Lys Glu
                660                 665                 670

Asp Asp Lys Glu Asp Asp Lys Glu Asp Lys Glu Asp Asn Lys Glu
                675                 680                 685

Lys Asp Lys Glu Asp Asn Lys Glu Lys Asp Lys Glu Asp Lys Glu
690                 695                 700

Lys Asp Lys Glu Asp Asp Lys Glu Lys Asp Lys Glu Asp Asn Lys Glu
705                 710                 715                 720

Lys Asp Lys Glu Asp Asn Lys Glu Lys Asp Lys Glu Asp Asp Lys Glu
                725                 730                 735

Lys His Asp Lys His Val Arg Arg Ile Lys Lys Lys Met Lys Asp Asp
            740                 745                 750

Asp Tyr Asp Glu Ser Leu Lys Thr Lys Asn Tyr Pro His Asn Met
            755                 760                 765

Thr Phe Gly Gln Gln Gln Tyr Phe Pro Tyr Tyr Asn Pro Leu Glu Gln
770                 775                 780

Gln Asn Tyr Gln Leu His His Ile Ile Lys Gln Gln Gln Asn Tyr His
785                 790                 795                 800

Pro His His Ile Ile Lys Gln Gln Gln Asn His Asn Pro His His Ile
                805                 810                 815

Leu Gln Glu Gln Glu Lys His His Pro Gln Gly Ile Pro Lys Glu Gln
            820                 825                 830

Pro Tyr Asn Asn Val Pro Tyr Ile Leu Lys Lys Gly Leu Glu Pro Lys
            835                 840                 845

Thr His Asn His Val Lys Glu Asp Gln Pro Asn Ile Lys Gln Gly Val
    850                 855                 860

Val Lys Gly Gln Glu Pro His Val Asp Asp Met His Asn Asn Thr Lys
865                 870                 875                 880

Glu His Lys Asn Phe Lys Asn Thr Thr Asp Val Lys Gln Pro Ala Ser
                885                 890                 895

His Ile Tyr Asn Asn Ser Ser Glu Lys Gln Ile Glu His Val Tyr Asn
            900                 905                 910

Lys Ser Pro Glu Lys Gln Ile Glu His Val Tyr Asn Lys Ser Pro Glu
            915                 920                 925

Lys Gln Ile Glu His Val Tyr Asn Asn Ser Pro Glu Lys Gln Ile Glu
            930                 935                 940

His Val Tyr Asn Asn Ser Pro Glu Lys Gln Ile Glu His Val Tyr Asn
945                 950                 955                 960

Asn Ser Pro Glu Lys Gln Ile Glu His Val Tyr Asn Asn Ser Pro Glu
                965                 970                 975

Lys Pro Ala Arg His Thr Asn Asn Ile Ser Leu Glu Lys Gln Asn Ser
            980                 985                 990

His Lys Tyr Asn Val Asn Ile Gln Asp Arg His Asp Pro Val Tyr Tyr
        995                 1000                1005

Lys Tyr Glu Asp Met Leu Lys Arg Asp Lys Asp Leu Phe Thr Ile
```

```
                1010                1015                1020

Ile Asn  Asn  Ile  Cys  Glu  Leu  Glu  Phe  Asn  Ser  Thr  Asn  Asn  Tyr
        1025                1030                1035

Leu Met  Lys  Ile  Ile  Asn  Asn  Asp  Lys  Leu  Lys  His  Asn  Ser  Leu
        1040                1045                1050

Asn Asp  Asn  Glu  Ala  Ile  Leu  Lys  Glu  Ile  Thr  Lys  Thr  Gln  Asn
        1055                1060                1065

Glu Leu  Phe  Ser  Leu  Lys  Leu  Pro  Leu  Glu  Ile  Lys  Val  Ser  Met
        1070                1075                1080

Ala Leu  Arg  Ile  Ser  Glu  Arg  Leu  Arg  Ala  Phe  Val  Phe  Asp  Lys
        1085                1090                1095

Asp Leu  Thr  Ala  Tyr  Tyr  Ile  Lys  Lys  Leu  Lys  Asp  Ile  Phe  Lys
        1100                1105                1110

Leu Glu  Thr  Glu  Ala  Ala  Lys  Asn  Tyr  Tyr  Tyr  Val  Lys  Cys
        1115                1120                1125

Gln Lys  Thr  Phe  Ser  Asp  Lys  Lys  Arg  Leu  Val  Asn  Asn  Leu  Asp
        1130                1135                1140

Ser Ile  Lys  Leu  Tyr  Tyr  Glu  Ser  Gln  Ile  Asn  Lys  Asn  Phe  Ile
        1145                1150                1155

Ser Ile  Pro  Lys  Asp  Lys  Ile  Pro  Thr  Ala  Ile  Tyr  Arg  Ile  Ser
        1160                1165                1170

Asn Leu  Val  Asn  Asp  Leu  Ile  Phe  Leu  Leu  Pro  Gln  Ser  Asn  Ala
        1175                1180                1185

Asn Lys  Ala  Leu
        1190

<210> SEQ ID NO 13
<211> LENGTH: 347
<212> TYPE: PRT
<213> ORGANISM: Plasmodium falciparum

<400> SEQUENCE: 13

Met Tyr  Ser  Asn  Cys  Leu  Arg  His  Arg  Pro  His  Leu  Ser  Leu  Cys  Val
1                 5                  10                  15

Phe Leu  Leu  Val  Cys  Ile  Phe  Tyr  Val  Phe  Phe  Lys  Pro  Thr  Ala  Tyr
            20                  25                  30

His Lys  Ser  Ser  Gly  Ser  Cys  Val  Asn  Ser  Leu  Trp  Ser  Arg  Asn
        35                  40                  45

Leu Ser  Glu  Pro  Asn  Asn  Ser  Arg  Asn  Ser  Leu  Tyr  Asn  Asn  Lys
    50                  55                  60

Leu Lys  Ser  Asn  Pro  Tyr  Asp  Ser  Lys  Phe  Arg  Asn  Asp  Ile  Tyr  Thr
65                  70                  75                  80

Ser Arg  Gly  Ser  His  Asn  Thr  Lys  Glu  Ser  Lys  Glu  Lys  Ser  Ser  Leu
            85                  90                  95

Arg Asp  Gly  Val  Ser  Arg  Asn  Asn  Ala  Ser  Asp  Val  Ser  Arg  Asn  His
            100                 105                 110

Leu Arg  Glu  Pro  Leu  Tyr  Lys  Arg  Phe  Glu  Lys  Arg  Asn  Asn  Asp  Pro
        115                 120                 125

Glu Glu  Gln  Asn  Lys  Leu  Glu  Glu  Arg  Lys  Lys  Gly  Glu  Glu  Glu
        130                 135                 140

Gln Asn  Lys  Leu  Glu  Glu  Glu  Arg  Lys  Lys  Arg  Glu  Glu  Lys  Ser
145                 150                 155                 160

Asn Asp  Thr  Phe  Leu  Ser  Asn  Asn  Asp  Thr  Asn  Ser  Asn  Gly  Ser  Thr
            165                 170                 175

Asn Ile  Asp  Ser  Ser  Glu  Leu  Leu  Glu  Asn  Asp  Ile  Asp  Glu  Tyr  Ser
```

```
                        180                 185                 190
Asp Ser Asn Asp Ile Ser Ile Leu Glu Asp Phe Asn Asn Asp Ile Asn
                195                 200                 205

Glu Ala Leu Asn Leu Leu Ser Asp Asp Glu Ile Asp Asp Met Ile Asn
            210                 215                 220

Asn Leu Asn Asp Ile Ala Ser Phe Glu Glu Met His Asn Ile Trp Asn
225                 230                 235                 240

Glu Leu Cys Lys Ser Glu Lys Tyr Lys Phe Leu Tyr Leu Ile Tyr Asp
                245                 250                 255

Leu Arg Lys Leu Tyr Glu Glu Leu Ile Asp Asp Ile Asp Asp Ile Glu
            260                 265                 270

Glu Glu Glu Glu Glu Leu Trp Glu Thr Cys Val Phe Gly Val Gly Lys
        275                 280                 285

Ile Gln Val Arg Ala Ser Gly Thr Tyr Asn Asp Leu Phe Asn Asn Leu
        290                 295                 300

Leu Ser Asp Glu Tyr Val Ser Lys Lys Glu Phe Ile Asp Phe Ile Lys
305                 310                 315                 320

Glu Cys Arg Asn Arg Leu Ser Leu Ile Arg Ser Gln Leu Lys Asp Lys
                325                 330                 335

Cys Glu Lys Lys Ile Ile Asp Ala Leu Ser Asn
                340                 345

<210> SEQ ID NO 14
<211> LENGTH: 417
<212> TYPE: PRT
<213> ORGANISM: Plasmodium falciparum

<400> SEQUENCE: 14

Met Asn Leu Lys Asn Leu Gly Phe Lys Ser Phe Phe Ser Asp Asp Lys
1               5                   10                  15

Lys Asn Lys Ser Thr Leu Phe Ser Phe Ser Arg Asn Ile Tyr Met
            20                  25                  30

Leu Ile Cys Ile Ile Ser Val Met Tyr Val Ser Phe Met Asn Val His
        35                  40                  45

Met Asn Asp Glu Asn Asn Thr Ser Asp Ser Lys Ser Val Ser Leu Val
    50                  55                  60

Glu Arg Asn Leu Ser Glu Tyr Tyr Ile Gly Arg Tyr Gly Ala Leu Arg
65                  70                  75                  80

Asn Tyr Tyr Gly Pro Ile Ile Gly Val Asn Lys Lys His Tyr Ser Gly
                85                  90                  95

Lys His Asn Lys Asp Thr Ser Tyr Asp Ala Leu Glu Glu Asp Ser Asn
            100                 105                 110

Asp Ser Glu Glu Asp Ser Glu Asn Asp Ser Glu Asp Glu Ser Glu Val
        115                 120                 125

Glu Ser Glu Asn Glu Ser Glu Asn Glu Ser Asp Gln Ser Glu Asn
    130                 135                 140

Asp Thr Glu Asn Asp Thr Glu Asn Glu Thr Glu Gln Glu Ser Glu Glu
145                 150                 155                 160

Gln Ser Gln Asn Glu Ser Asp Gly Glu Ser Glu Asn Ser Glu Glu
                165                 170                 175

Glu Ser Asp Asp Glu Pro Val Lys Lys Asn Ala Pro Lys Asn Lys Glu
            180                 185                 190

Asp Thr Lys Asn Glu Glu Lys Lys Asp Leu Arg Gln Gly Lys Gly Asp
        195                 200                 205

Ile Ile Arg Lys Thr Leu Asn Asn Thr Asn Pro Asn Lys Asp Lys Phe
```

```
                210                 215                 220
Asn Asp Ser Asn Asn Lys Phe Lys Ala Pro Leu Lys Asn Leu Asn Tyr
225                 230                 235                 240

Asn Asp Ile Thr Arg Gln Leu Asn Ser Tyr Glu Ile Ser Asp Val Ile
                245                 250                 255

Lys Gly Leu Lys Glu Asn Ile Pro Asn Glu Asp Leu Val Asn Val Trp
                260                 265                 270

Ile Gln Thr Leu Gly Val Cys Lys Ser Gly Gly His Asp Met Ile Ser
                275                 280                 285

Asn Leu Lys Asn Tyr Glu Lys Ser Cys Leu Ser Glu Tyr Lys Lys Ile
290                 295                 300

Ile Leu Pro His Tyr Gly Gly Pro Pro Arg Glu Lys Asn Pro Glu Glu
305                 310                 315                 320

Tyr Trp Glu Lys Cys Leu Tyr Asp Phe Glu Val Lys Leu Leu Asn Ala
                325                 330                 335

Ser Tyr Glu Tyr Asn Ser Lys Phe Tyr Glu Leu Leu Asn Lys Lys Asp
                340                 345                 350

Lys Leu Phe Lys Ile Lys Glu Phe Leu Phe Ser Cys Leu Asp Glu Phe
                355                 360                 365

Ser Asn Leu Lys Lys Gln Leu Tyr Lys Glu Tyr Lys Asn Glu Leu Tyr
370                 375                 380

Asp Asn Ile Met Arg Ala Ser Gly Lys Lys Tyr Ser Ile Leu Lys Ile
385                 390                 395                 400

Ile Tyr Ile Tyr Ile Tyr Ile Tyr Leu Ser Lys Arg Asp Ser
                405                 410                 415

Asp

<210> SEQ ID NO 15
<211> LENGTH: 670
<212> TYPE: PRT
<213> ORGANISM: Plasmodium falciparum

<400> SEQUENCE: 15

Met Leu Asn Leu Phe Val Phe Leu Ile Leu Phe Ile Ile Arg Phe Ile
1               5                   10                  15

Val Ile Arg Gly Ser Lys Tyr Arg Tyr Glu Asn Asn Ser Glu Leu Leu
                20                  25                  30

Ile Glu Arg Ile Lys Arg Gly Lys Glu Ala Leu Asp Asp Ile Leu Lys
            35                  40                  45

Ala Lys Met Lys Ala Glu Glu Tyr Gln Lys Asn Lys Lys Arg Ile
50                  55                  60

Lys Ser Gln Asn Lys Asn Ser Tyr Lys Asn Lys Lys Glu Asp Asp Glu
65                  70                  75                  80

Glu Glu Lys Asp Tyr Asp Glu Asp Asn Asn Asn Ile Tyr Val Gln
                85                  90                  95

Glu Ile Lys Cys Tyr Glu Tyr Val Leu Glu Gln Leu Asn Asn Leu Asn
                100                 105                 110

Val Tyr Asn Cys Asn Glu Ile Asn Glu Asn Asn Lys Ser Leu Leu Ala
                115                 120                 125

Leu Ala Lys Thr Lys Cys Leu Phe Val Lys Ser Ile Arg Ser Phe Pro
130                 135                 140

Asp Glu Asn Ser Gly Cys Ile Leu Asn Pro Lys Lys Leu Asn Lys Leu
145                 150                 155                 160

Gln Leu Tyr Leu Tyr Asn Asn Asn Leu Phe Asn Glu Phe Ser Asn Gln
                165                 170                 175
```

```
Asn Phe Ser Arg Thr Leu Asn Leu Asn Glu Leu Arg Lys Ile Glu Lys
                180                 185                 190

Ile Ile Asn Pro Cys Tyr Tyr Glu Asn Asp Gln Thr Asp Glu Asn Tyr
            195                 200                 205

Val Asn Leu Leu Asn Asp Ile Ser Asn Ile Lys Glu Lys Gln Arg Asn
    210                 215                 220

Asn Tyr Glu His Ile Asn Tyr Thr Tyr Asn Asn Asp Met Asp Asn Leu
225                 230                 235                 240

Asp Gly Thr Asn Tyr Met Ser Glu Lys Asn Asn Tyr Leu Lys Lys Lys
                245                 250                 255

Leu Cys Glu Asn Leu Lys Tyr Lys Ile Val Thr Asn Cys Thr Ser Asn
                260                 265                 270

Lys Asn Met Ser Asp Thr Ala Phe Gln Ile Tyr His Ser Glu Leu Asn
                275                 280                 285

His Ile Asp Asp Ile Cys Phe Tyr Ile Gln Ser Asn Glu Trp Asn Lys
                290                 295                 300

Arg Thr Glu Glu Asn Ile Asn Arg Leu Ala Gln Thr Ser Leu Tyr Ile
305                 310                 315                 320

Ser Lys Gln Met Thr Thr Asn Leu Glu Asn Met Lys Leu Ile Glu Asn
                325                 330                 335

Ala Gln Ile Lys Gln Ile Glu Asn Thr Asn Arg Phe Asp Asn Phe Leu
                340                 345                 350

Lys Gly Leu Lys Asn Asp Phe Ser Glu Ile Ile Gln Ile Leu Leu Lys
                355                 360                 365

Ile Lys Tyr His His Glu Ser Ile Thr Lys Phe Leu Arg Ala Phe Lys
                370                 375                 380

Met Ile Val Met Tyr Leu Leu Ile Ile Ile Leu Val Leu Phe Ile Thr
385                 390                 395                 400

Ser Arg Ser Tyr Ala Tyr Ser Arg Thr Thr Leu Ile Tyr Phe Tyr Lys
                405                 410                 415

Met Phe Thr Val Asn Glu Tyr Val Tyr Ile Leu Leu Asn Ile Asn Glu
                420                 425                 430

His Phe Ile Ser Tyr Ser Ile Lys Gly Ile Arg Tyr Thr Phe Val Ile
                435                 440                 445

Ile Gly Ile Lys Val Phe Ile Ser Ser Ile Ile Thr Tyr Lys Glu Pro
                450                 455                 460

Ala Lys Val Ile Glu Glu Leu Lys Val Ile Lys Lys Ile Val Gln
465                 470                 475                 480

Lys Asn Ser Gln Gln Tyr Gln Asn Lys Ile Lys Glu Ile Glu Asn Glu
                485                 490                 495

Asn Asn Asn Ile Leu Tyr Asn Asp Ile Asp Gln Lys Thr Ile Ser Ile
                500                 505                 510

Ile Asn Leu Trp Ser Cys Phe Asn Glu Asn Met Asp Ser Leu Tyr Glu
                515                 520                 525

Asp Asp Glu Asp Phe Asn Leu Ser Asn Tyr Asn Ser Asp Asp Glu Ser
                530                 535                 540

Ser Ser Ser His Thr Ser Leu Ala Ser Glu His Phe Thr Leu Asn Glu
545                 550                 555                 560

Ile Asp Glu Tyr Asn Asp Glu Pro Ile Gly Ile Arg Ile Lys Thr Leu
                565                 570                 575

His Arg Lys Asn Arg Pro Ile Phe Phe His Tyr Met Pro Ser Pro Thr
                580                 585                 590

Asn Ile Lys Ala Tyr Thr Glu Asn Pro Ile Ser Phe Thr Asn Met Ile
```

```
                    595                 600                 605
Glu Tyr Asn His Asn Glu Ile Met Arg Val Lys Glu Asn Arg Ile Asn
            610                 615                 620

Asn Glu Leu Ile Ile Asn Asp His Lys Ser Tyr Glu Thr Leu Ile Ile
625                 630                 635                 640

Glu Asn Asp Asp Gln Asn Glu Thr Pro Asn Ile Tyr Asp Leu Asn Lys
                645                 650                 655

Ala Glu Glu Lys Leu Asn Lys Tyr Tyr Ser Leu Asp Ser Phe
            660                 665                 670

<210> SEQ ID NO 16
<211> LENGTH: 2110
<212> TYPE: PRT
<213> ORGANISM: Plasmodium falciparum

<400> SEQUENCE: 16

Met Leu Tyr Ser Arg Leu Asp Ile Lys Lys His Asn Glu Asn Thr Lys
1               5                   10                  15

Asn Met Ser Lys Cys Tyr Thr Ile Val Ser Asp Glu Leu Ile Ser Arg
            20                  25                  30

Glu Tyr Asn Ile Lys Lys Asn Arg Met Trp Tyr Tyr Ile Phe Val Lys
        35                  40                  45

Ile Leu Phe Leu Ser Phe Phe Ile Cys Ile Leu Asn Gly Ser Ser Tyr
50                  55                  60

Asp Thr Tyr Cys Lys Glu Gly Asn Lys Glu Asp Asn Val Glu Gly Leu
65                  70                  75                  80

Phe Ser Ile Arg Pro Ser Arg Ser Leu Thr Glu Arg Lys Gln Arg Asn
                85                  90                  95

Asn Gly Lys Pro Ser Val Tyr Val Asn Asn Gly Glu Glu Glu Tyr Tyr
            100                 105                 110

Glu Glu Val Tyr Ser Glu Glu His Ser Pro Asp Glu Tyr Ala Asp
        115                 120                 125

Gly Glu Tyr Tyr Asp Asp Gly Asn Tyr Glu Glu Val Asn Tyr Asp
130                 135                 140

Glu Glu Tyr Tyr Glu Glu Gly Glu Lys Ser Lys Asn Val Leu Glu
145                 150                 155                 160

Lys Tyr Asn Asp Tyr Ala Ser Lys Ser His Gly Met Ser Ser Val Leu
                165                 170                 175

Lys Ser Val Ile Ser Gly Phe Thr Glu Thr Cys Asn Asp Val Lys Glu
            180                 185                 190

Ala Val Lys Pro Asn Ile Asp Thr Ile Lys Asp Thr Leu Ser Ser Gly
        195                 200                 205

Ile Thr Asn Ile Asp Lys Arg Val Val Gly Asn Val Ser Ser Ile Ile
210                 215                 220

Asn Lys Ile Thr Asn Ala Asp Glu Glu Asp Ser Glu Glu Cys Asp Gln
225                 230                 235                 240

Tyr Asp Glu Tyr Asp Gln Tyr Asp Glu Asn Met Asn Asp Gln Met Phe
                245                 250                 255

Asp Glu Met Glu Tyr Glu Glu Asn His Asn Thr Pro Ser Ser Pro Asn
            260                 265                 270

Leu Lys Lys Arg Ala Ser Asn Tyr Met His Lys Asn Pro Asn Lys Val
        275                 280                 285

Asn Thr Lys Thr Val Asn Lys Gln Asn Lys Phe Ser Asn Thr Gly Lys
        290                 295                 300

Lys Phe Val Gln Glu Phe Lys Ser Asn Thr His Asp Gly Met Asn Asn
```

```
            305                 310                 315                 320
Lys Val Asn Thr Thr Asn Asn Ala Pro Asn Val Ile Lys Ser Asn Thr
                325                 330                 335

His Gly Gly Met Asn Asn Lys Val Asn Thr Thr Asn Asn Ala Pro Asn
                340                 345                 350

Glu Ile Lys Met Asn Thr Tyr Asp Gly Met Asn Asn Lys Val Asn Thr
                355                 360                 365

Thr Asn Asn Thr Pro Asn Glu Ile Lys Met Asn Thr Tyr Asp Gly Met
            370                 375                 380

Asn Asn Lys Val Asn Thr Thr Asn Asn Ala Pro Asn Glu Ile Lys Ser
385                 390                 395                 400

Asn Thr Tyr Asp Asp Met Asn Asn Lys Val Asn Thr Thr Asn Asn Ala
                405                 410                 415

Pro Asn Glu Ile Lys Ser Asn Thr Asp Asn Gly Val Asn Asn Thr Thr
                420                 425                 430

Tyr Ala Thr Thr Lys Asn Phe Val Ser Glu Phe Asn Ser Asn Tyr Asp
                435                 440                 445

Asp Gly Ile Asn Lys Gly Ser Tyr Thr Thr Lys Ser Tyr Val Ser Glu
            450                 455                 460

Phe Lys Ser Asn Tyr Asp Gly Gly Ile Asn Lys Glu Ser Tyr Thr Thr
465                 470                 475                 480

Lys Ser Tyr Val Ser Glu Phe Lys Ser Asn Ser Asp Gly Gly Ile Asn
                485                 490                 495

Lys Glu Ile Tyr Thr Pro Lys Ile Tyr Val Ser Glu Phe Lys Asn Asn
                500                 505                 510

Asp Asp Glu Gly Ile Asn Lys Glu Ser Tyr Thr Thr Lys Ser Tyr Val
                515                 520                 525

Ser Glu Phe Lys Tyr Asn Asp Asp Gly Gly Ile Asn Lys Glu Ile Tyr
            530                 535                 540

Thr Pro Gln Ile Tyr Val Ser Glu Phe Lys Asn Asn Asp Asp Glu Gly
545                 550                 555                 560

Ile Asn Lys Glu Ser Tyr Thr Thr Lys Ser Tyr Val Ser Glu Phe Lys
                565                 570                 575

Tyr Asn Asp Asp Gly Gly Ile Asn Lys Glu Ile Tyr Thr Pro Lys Ile
                580                 585                 590

Tyr Val Ser Glu Phe Lys Asn Asn Asp Asp Gly Asp Ile Asn Asn Glu
                595                 600                 605

Ile Ser Thr Pro Lys Asn Tyr Val Ser Glu Phe Lys Asn Asn Asp Asp
            610                 615                 620

Glu Asp Leu Lys Lys Glu Ser Tyr Thr Thr Lys Ser Tyr Val Ser Glu
625                 630                 635                 640

Phe Lys Asn Asn Asp Asp Gly Gly Leu Lys Lys Glu Ile Ser Thr Pro
                645                 650                 655

Lys Asn Tyr Val Ser Glu Phe Lys Asn Asn Phe Asp Gly Gly Ile Asn
                660                 665                 670

Lys Glu Val Ser Val Pro Arg Leu Ser Val Asn Glu Phe Glu Asn Asn
                675                 680                 685

Asp Asp Val Gly Leu Lys Lys Glu Val Ser Val Pro Arg Leu Ser Val
            690                 695                 700

Asn Glu Phe Glu Asn Asn Asp Asp Val Gly Leu Lys Lys Glu Val Ser
705                 710                 715                 720

Val Pro Arg Leu Ser Val Ser Glu Phe Glu Asn Asn Asp Asp Val Gly
                725                 730                 735
```

-continued

```
Leu Lys Lys Glu Val Ser Val Pro Arg Leu Ser Val Asn Glu Phe Glu
            740                 745                 750

Asn Asn Asp Asp Val Gly Leu Lys Lys Glu Ile Ser Thr Pro Lys Asn
            755                 760                 765

Tyr Val Ser Glu Phe Lys Asn Asn Phe Asp Gly Cys Leu Lys Lys Glu
        770                 775                 780

Val Ser Val Pro Arg Leu Ser Val Ser Glu Phe Glu Asn Asn Asp Asp
785                 790                 795                 800

Val Gly Leu Lys Lys Glu Val Ser Val Pro Arg Leu Ser Val Asn Glu
            805                 810                 815

Phe Glu Asn Asn Asp Asp Val Gly Leu Lys Lys Glu Val Ser Val Pro
        820                 825                 830

Arg Leu Ser Val Asn Glu Phe Glu Asn Asn Asp Asp Val Gly Leu Lys
            835                 840                 845

Lys Glu Val Ser Val Pro Arg Leu Ser Val Ser Glu Phe Glu Asn Asn
    850                 855                 860

Asp Asp Val Gly Leu Lys Lys Glu Ile Ser Thr Pro Lys Asn Tyr Val
865                 870                 875                 880

Ser Glu Phe Lys Asn Asn Phe Asp Gly Cys Leu Lys Lys Glu Val Ser
            885                 890                 895

Val Pro Arg Leu Ser Val Ser Glu Phe Lys Asn Asn Phe Asp Gly Cys
        900                 905                 910

Leu Lys Lys Glu Val Ser Val Pro Arg Leu Ser Val Ser Glu Phe Glu
        915                 920                 925

Asn Asn Asp Asp Val Gly Leu Lys Lys Glu Val Ser Val Pro Arg Leu
    930                 935                 940

Ser Val Asn Glu Phe Glu Asn Asn Asp Asp Val Gly Leu Lys Lys Glu
945                 950                 955                 960

Val Ser Val Pro Arg Leu Ser Val Ser Glu Phe Lys Asn Asn Asp Asp
            965                 970                 975

Val Ser Leu Asn Lys Glu Ser Tyr Pro Arg Arg Lys Phe Val Ser Glu
            980                 985                 990

Leu Lys Ser Asn Thr Tyr Ser Tyr Met Asn Lys Asn Pro Tyr Ser His
        995                 1000                1005

Lys Lys Tyr Val Gly Val Leu Lys Asn Asn Ser Asp Gly Gly Ile
    1010                1015                1020

Asn Lys Asp Phe Gly Thr Lys Gly Ser Val Ile Asn Glu Ile Lys
    1025                1030                1035

Asp Asn Asn Met Asn Asn Glu Asn Met Gln Leu Gly Thr Thr Lys
    1040                1045                1050

Asn Val Leu Ser Glu Gly Thr Tyr Asn Asn Glu Ser Asp Met Asn
    1055                1060                1065

Lys Lys Pro Ser Thr Ser Thr Asn Ile Asn Ser Glu Asn Lys Gln
    1070                1075                1080

Asn Ala His Thr Arg Ser Met Ser Val Ala Asn Thr Lys Ser His
    1085                1090                1095

Val Gln Gln Asn Val Lys Thr Phe Ser Ser Asn His Tyr Glu Asn
    1100                1105                1110

Glu Asn Asn His Lys Met His Asn Val Asn Glu Lys Glu Glu Val
    1115                1120                1125

Pro Lys Ile Asp Arg Thr Lys Ile Asn Thr Arg Arg Ala Ser Val
    1130                1135                1140

Ser Glu Ile Asn Glu Asn Val Glu Glu Thr Lys Lys Asp Ile Pro
    1145                1150                1155
```

```
Gln Asn Lys Asn Tyr Lys His Leu Thr Asp Glu Glu Asn Lys Val
    1160            1165            1170
Glu Lys Glu Met Ser Ile His Asp Gly Met Lys Gly Gln Lys Tyr
    1175            1180            1185
Gly Ser Lys Asn Val Arg Ser Phe Ser Ser Gln Gly Ile Arg Gln
    1190            1195            1200
Asp Phe Pro Tyr Lys Asn Glu Asn Asn His Lys Met Tyr Asn Val
    1205            1210            1215
Asn Glu Lys Glu Glu Val Pro Lys Ile Asp Arg Thr Lys Ile Asn
    1220            1225            1230
Thr Arg Arg Ala Ser Val Ser Glu Ile Asn Glu Asn Val Glu Glu
    1235            1240            1245
Thr Lys Lys Asp Ile Pro Gln Asn Lys Asn Tyr Lys His Leu Thr
    1250            1255            1260
Asp Glu Glu Asn Lys Val Glu Lys Glu Met Ser Ile His Asp Gly
    1265            1270            1275
Met Lys Gly Gln Lys Tyr Gly Ser Lys Asn Val Arg Ser Phe Ser
    1280            1285            1290
Ser Gln Gly Ile Arg Gln Asp Phe Pro Tyr Lys Asn Glu Asn Asn
    1295            1300            1305
His Lys Met Tyr Asn Val Asn Glu Lys Glu Glu Val Pro Lys Ile
    1310            1315            1320
Asp Arg Thr Lys Ile Asn Thr Arg Arg Ala Ser Val Ser Glu Ile
    1325            1330            1335
Asn Glu Asn Val Glu Glu Thr Lys Lys Asp Ile Pro Gln Asn Lys
    1340            1345            1350
Asn Tyr Lys His Leu Thr Asp Glu Glu Asn Lys Val Glu Lys Glu
    1355            1360            1365
Met Ser Ile His Asp Gly Met Lys Gly Gln Lys Tyr Gly Ser Lys
    1370            1375            1380
Asn Val Arg Ser Phe Ser Ser Gln Gly Ile Arg Gln Asp Phe Pro
    1385            1390            1395
Tyr Lys Asn Glu Asn Asn His Lys Met Tyr Asn Val Asn Glu Lys
    1400            1405            1410
Glu Glu Val Pro Lys Ile Asp Arg Thr Lys Ile Asn Thr Arg Arg
    1415            1420            1425
Ala Ser Val Ser Glu Ile Asn Glu Asn Val Glu Glu Thr Lys Lys
    1430            1435            1440
Asp Ile Pro Gln Asn Lys Asn Tyr Lys His Leu Thr Asp Glu Glu
    1445            1450            1455
Asn Lys Val Glu Lys Glu Met Ser Ile His Asp Gly Met Lys Gly
    1460            1465            1470
Gln Lys Tyr Gly Ser Lys Asn Val Arg Ser Phe Ser Ser Gln Gly
    1475            1480            1485
Ile Arg Glu Asp Phe Pro Tyr Lys Asn Glu Asn Asn His Lys Met
    1490            1495            1500
His Asn Val Asn Glu Lys Glu Glu Val Pro Lys Ile Asp Arg Thr
    1505            1510            1515
Lys Ile Asn Thr Arg Arg Ala Ser Val Ser Glu Ile Asn Glu Asn
    1520            1525            1530
Val Glu Glu Thr Lys Lys Asp Ile Pro Gln Asn Lys Asn Tyr Lys
    1535            1540            1545
His Leu Thr Asp Glu Glu Asn Lys Val Glu Lys Glu Met Ser Ile
```

```
              1550                1555                1560

His  Asp  Gly  Met  Lys  Gly  Gln  Lys  Tyr  Gly  Ser  Lys  Asn  Ile  Arg
     1565                1570                1575

Ser  Phe  Ser  Ser  Gln  Gly  Ile  Arg  Glu  Asp  Phe  Pro  Tyr  Lys  Asn
     1580                1585                1590

Glu  Asn  Asn  His  Lys  Met  His  Asn  Val  Asn  Glu  Lys  Glu  Glu  Val
     1595                1600                1605

Pro  Lys  Ile  Asp  Arg  Thr  Lys  Ile  Asn  Thr  Arg  Arg  Ala  Ser  Val
     1610                1615                1620

Ser  Glu  Ile  Asn  Glu  Asn  Val  Glu  Glu  Thr  Lys  Lys  Asp  Ile  Pro
     1625                1630                1635

Gln  Asn  Lys  Asn  Tyr  Lys  His  Leu  Thr  Asp  Glu  Glu  Asn  Lys  Val
     1640                1645                1650

Glu  Lys  Glu  Met  Ser  Ile  His  Asp  Gly  Met  Lys  Gly  Gln  Lys  Tyr
     1655                1660                1665

Gly  Ser  Lys  Asn  Ile  Arg  Ser  Phe  Ser  Ser  Gln  Gly  Ile  Arg  Glu
     1670                1675                1680

Asp  Phe  Pro  Tyr  Glu  Asn  Glu  Asn  Asn  Lys  His  Ser  Gly  Leu  Asn
     1685                1690                1695

Thr  Pro  Lys  Asn  Ile  Pro  Val  Asn  Asn  Arg  Lys  Leu  Arg  Lys  Gly
     1700                1705                1710

Cys  Thr  Val  His  Glu  Ile  Gly  Phe  Met  Asp  Asp  Asp  Asn  Arg  Asn
     1715                1720                1725

Thr  Met  Asn  Asp  Thr  Thr  Pro  Asn  Val  Asn  Leu  Lys  Lys  Lys  Tyr
     1730                1735                1740

Asn  Phe  Gly  Pro  Ser  Glu  Gly  Lys  Glu  Lys  Asn  Asn  Thr  Gln  Asn
     1745                1750                1755

Glu  Thr  His  Lys  Leu  Lys  Ser  Asp  Ile  Gly  Asn  Phe  Lys  Asn  Ser
     1760                1765                1770

Leu  His  Lys  Glu  Glu  Lys  Asn  Val  Thr  Asp  Lys  Leu  Lys  Pro  Asn
     1775                1780                1785

Phe  Glu  Ser  Ser  Lys  Glu  Asn  Glu  Ser  Asn  Lys  Gly  Thr  Asn  Val
     1790                1795                1800

Pro  Asp  Lys  Leu  Lys  Ile  Glu  Lys  Asp  Ala  Asn  Ser  Gly  Ser  Glu
     1805                1810                1815

Leu  Lys  Asn  Thr  Asn  Asn  Lys  Glu  Lys  Glu  Val  Lys  Asn  Lys  Phe
     1820                1825                1830

Asn  Asp  Thr  Thr  Asp  Lys  Met  Ser  Gln  Glu  Lys  Gln  Asp  Asn  Gln
     1835                1840                1845

Lys  Glu  Val  Gly  Val  Arg  Phe  Val  Asp  Asn  Lys  Glu  Lys  Val  Leu
     1850                1855                1860

Gly  Lys  Asn  Glu  His  His  Glu  Asp  His  Leu  Lys  Gly  Lys  Phe  Val
     1865                1870                1875

Asp  Asn  Arg  Glu  Lys  Thr  Leu  Gly  Lys  His  Glu  His  His  Glu  Glu
     1880                1885                1890

Tyr  Val  Lys  Gly  Lys  Phe  Gly  Asp  Asn  Arg  Glu  Lys  Thr  Leu  Gly
     1895                1900                1905

Lys  His  Glu  His  His  Glu  Asp  His  Leu  Lys  Gly  Lys  Phe  Gly  Asp
     1910                1915                1920

Asn  Arg  Glu  Lys  Lys  Leu  Gly  Lys  His  Glu  His  His  Glu  Asp  His
     1925                1930                1935

Leu  Lys  Gly  Lys  Phe  Gly  Asp  Asn  Arg  Glu  Lys  Thr  Leu  Gly  Lys
     1940                1945                1950
```

```
His Glu His His Glu Glu Tyr Val Lys Gly Lys Phe Val Asp Asn
    1955                1960                1965

Arg Glu Lys Thr Leu Gly Lys His Lys His His Glu Asp His Leu
    1970                1975                1980

Lys Gly Lys Phe Gly Asp Asn Arg Glu Lys Thr Leu Gly Lys His
    1985                1990                1995

Glu His His Glu Glu Tyr Val Lys Gly Lys Phe Val Asp Asn Arg
    2000                2005                2010

Glu Lys Thr Leu Gly Lys His Lys His His Glu Asp His Leu Lys
    2015                2020                2025

Gly Lys Phe Gly Asp Asn Arg Glu Lys Thr Leu Gly Lys His Glu
    2030                2035                2040

His His Glu Glu Tyr Val Lys Gly Lys Phe Val Asp Asn Arg Glu
    2045                2050                2055

Lys Thr Leu Gly Lys His Lys His His Glu Asp His Leu Lys Gly
    2060                2065                2070

Lys Phe Gly Asp Asn Arg Glu Lys Thr Leu Gly Lys His Lys His
    2075                2080                2085

His Glu Lys Gly Val Asn Val Gln Ser Ser Asn Thr Asn Lys His
    2090                2095                2100

Met Pro Arg Lys Met Leu Arg
    2105                2110

<210> SEQ ID NO 17
<211> LENGTH: 778
<212> TYPE: PRT
<213> ORGANISM: Plasmodium falciparum

<400> SEQUENCE: 17

Met Lys Phe Arg Lys Ser Lys Asn Glu Lys Asn Glu Gln Gln Asp
1               5                   10                  15

Asp Leu Leu Lys Asn Lys Glu Asp Asp Leu Leu Lys Asn Lys Glu Gly
                20                  25                  30

Asp Leu Leu Lys Asn Lys Glu Gly Asp Leu Leu Lys Asn Lys Gly Asp
                35                  40                  45

Leu Leu Lys Asn Glu Glu Gly Asp Leu Leu Lys Asn Glu Glu Gly Asp
50                  55                  60

Leu Leu Lys Asn Lys Gly Asp Leu Ile Lys Asn Lys Glu Gly Asp Leu
65                  70                  75                  80

Leu Lys Ser Lys Glu Gly Asp Leu Ile Lys Asn Lys Glu Gly Asp Leu
                85                  90                  95

Ile Lys Asn Lys Glu Gly Asp Leu Leu Lys Ser Lys Glu Gly Asp Leu
                100                 105                 110

Ile Lys Asn Lys Glu Gly Asp Leu Leu Lys Ser Lys Glu Gly Asp Leu
                115                 120                 125

Ile Lys Asn Lys Glu Gly Asp Leu Ile Lys Asn Lys Glu Asp Val Leu
                130                 135                 140

Leu Asn Lys Gly Tyr Asn Ile Leu Gln Asn Lys Asn Asp Leu Leu
145                 150                 155                 160

Gln Asn Glu Tyr Tyr Asn Leu Leu Gln Asn Glu Gln Asp Asp Asn Gln
                165                 170                 175

Leu Lys Gly Asn Thr Leu Ile Thr Thr Lys Lys Glu Asp Lys Gly Cys
                180                 185                 190

Met Lys Lys Thr His Glu Asn Lys Ala Glu Cys Glu Lys Asn Glu Asp
                195                 200                 205
```

-continued

```
Lys Asn Cys Met Lys Lys Thr His Glu Asn Lys Ala Glu Cys Glu Lys
210                 215                 220

Asn Glu Asp Lys Asn Cys Met Lys Lys Thr His Gly Asn Lys Ala Glu
225                 230                 235                 240

Asp Glu Lys Asn Glu Asp Ile Leu Leu Met Ser Pro Thr Lys Gly Asn
                245                 250                 255

Asn Leu Trp Thr Arg Leu Lys Lys Gly Phe Ser Arg Gly Met Cys Met
                260                 265                 270

Asn Phe Leu Leu Asn Asp Asn Glu Lys Lys Leu Ser Thr Leu Tyr
            275                 280                 285

Val Thr Asn Met Leu Lys Asn Gln Leu Asn Ser Tyr Tyr Gly Ser Lys
290                 295                 300

Asn Ser Asn Asp Lys Lys Leu Glu Lys Ser Asp Asn Glu Gly Gly Glu
305                 310                 315                 320

Glu Lys Tyr Asp Asn Ser Asn Lys Glu Gln Asn Met Ile Tyr Asn Trp
                325                 330                 335

Lys Ile Gly Lys Glu Cys Phe Met Lys Lys Leu Asp Ser Val His Asn
                340                 345                 350

Phe Glu Met Asn Gly Val Asn Tyr Tyr Asp Phe Asn Leu Ile Ser Ile
                355                 360                 365

Pro Thr Ile Gly Tyr Ser Lys Ser Ser Lys Arg Leu Gln Leu Met Tyr
370                 375                 380

Lys Thr Asp Val Ile Tyr Gly Glu Asn Glu Asn Asp Lys Asn Asn Leu
385                 390                 395                 400

Lys Lys Lys Lys Leu Phe Leu Lys Lys Val Pro Ala Asn Leu Trp Ile
                405                 410                 415

Glu Gln Tyr Lys Leu Met Lys Glu Tyr Asp Gly Glu Tyr Val Tyr Ser
                420                 425                 430

Gly Glu Asn Tyr Val Met Glu Phe Leu Val Leu Ser Phe Leu Asp Thr
                435                 440                 445

Tyr His Pro Asn Ile Cys Pro Lys Leu Tyr Lys Ile Leu Tyr Glu Pro
                450                 455                 460

Pro Asn Lys Glu Tyr Ile Lys Asp Glu Asn Lys Lys Phe Gln Asn Ile
465                 470                 475                 480

Asp Asp Phe Val Lys Tyr Met Glu Asp Ile Ile Glu His Asn Lys Arg
                485                 490                 495

Asn Asn Ala Asn Asn Asn Val Asp Asn Asn Asn Ile His Asn His
                500                 505                 510

Lys Asn Asn Ile Asn Tyr Cys Ile Thr Asn Ser Asp Asn Lys His Asp
                515                 520                 525

Asn Asn Asn Asn Asp Asn Asn Ser Asp Asn Asn Cys Gly Tyr Val Val
                530                 535                 540

Met Val Ser Glu Tyr Tyr Gly Glu Asp Ile Phe Asp Phe Ile Ile Lys
545                 550                 555                 560

Arg Arg Lys Asn Ile Phe Leu Lys Ile Arg Arg Lys Asp Lys Ile Asn
                565                 570                 575

Ile Leu His Ala Cys Leu Lys Leu Leu Ala Arg Leu His Asp Ala Gly
                580                 585                 590

Leu Cys His Leu Asp Leu Thr Pro Asp Asn Ile Leu Ile Ser Lys Ser
                595                 600                 605

Met Asp Leu Arg Leu Cys Asp Phe Ala Lys Ser Thr Pro Met Tyr Ser
                610                 615                 620

Asn Lys Leu Arg His Leu Lys Glu Ser Glu Asp Ser Tyr Lys Phe Glu
625                 630                 635                 640
```

```
Ser Tyr Glu Thr His Val Ala Lys Ser Ala Tyr Thr Pro Pro Glu Cys
                645                 650                 655

Trp Glu Ile Tyr Trp Arg Tyr Glu Leu Lys Ile Lys Glu Pro Leu
            660                 665                 670

Glu Tyr Leu Lys Leu Ile Thr Asn Gln Glu Arg Lys Gln Phe Tyr
            675                 680                 685

Phe Asp Val Ala Cys Ala Asp Lys Phe Met Leu Gly Val Leu Phe Ile
690                 695                 700

Trp Ile Trp Thr Ser Gly Asn Leu Trp Val Cys Ser Asp Pro Leu Gln
705                 710                 715                 720

Asp Asp Tyr Phe His Cys Leu Met Lys Ser Asp Met Asn Phe Asn Asn
                725                 730                 735

Phe Pro Cys Ser Gln Asn Trp Pro His Gly Leu Lys His Ile Ile Lys
                740                 745                 750

Gln Leu Leu His Met Lys Tyr Arg Lys Asp Leu Asn Leu Asn Ile Leu
            755                 760                 765

Gly Ile His Pro Trp Trp Tyr Lys Lys Lys
            770                 775

<210> SEQ ID NO 18
<211> LENGTH: 253
<212> TYPE: PRT
<213> ORGANISM: Plasmodium falciparum

<400> SEQUENCE: 18

Met Lys Phe His Cys Val Glu Tyr Tyr Ser Glu Glu Asn His Ile Gln
1               5                   10                  15

Asn Thr Thr Asn Val Arg Leu Ile Arg Arg Lys Phe Leu Asn Leu Arg
            20                  25                  30

Asn Leu Ser Glu Thr Glu Ser Val Glu His Ser Gly Leu Ser Asn Thr
        35                  40                  45

Ser Glu Asp Val Glu Leu Glu Asn Gly Leu Glu Asn Asn Asn Asn
    50                  55                  60

Asn Asn Ile Ser Cys Asp Leu Glu Gly Ser Asn Ser Glu Asp Glu Val
65                  70                  75                  80

Lys Tyr Asn Asp Val Thr Thr Lys Arg Lys Cys Asp Asn Ile Asn Tyr
                85                  90                  95

Asn Asp Leu Ser Lys Gln Leu Thr Leu Glu Glu Leu His Ser Val Leu
            100                 105                 110

Asp Asp Leu Glu Lys Ser Thr Thr Lys Glu Asp Leu Tyr Asn Ile Trp
        115                 120                 125

Asn Gln Val Leu Gly Ile Ala Lys Asp Gly Phe Asp Gly Met Leu Thr
130                 135                 140

Glu Leu Ser Tyr Val Glu Glu Tyr Leu His Glu Tyr Glu Tyr Glu
145                 150                 155                 160

Arg Tyr His Tyr Phe Gly Gly Arg Lys Pro Val Ser Met Lys Asn Val
                165                 170                 175

Arg Glu Thr Trp Tyr Lys Ser Met His Asp Ile Gly Glu Ala Leu Ser
            180                 185                 190

Ser Thr Asp Val Lys Asn Thr Leu Asp Phe Tyr Ser Phe Val Lys Ser
        195                 200                 205

Gly Ala Ser Ile Asp Glu Met Lys Asn Phe Ile Tyr Glu Phe Ile Lys
    210                 215                 220

Tyr Tyr Asp Thr Leu Lys Asn Asp Leu Phe Asn Thr His Lys Lys Ile
225                 230                 235                 240
```

```
Phe Thr Glu Trp Met Lys Glu Leu Gln Gly Leu Glu Lys
                245                 250

<210> SEQ ID NO 19
<211> LENGTH: 428
<212> TYPE: PRT
<213> ORGANISM: Plasmodium falciparum

<400> SEQUENCE: 19

Met Cys Asn Lys Leu Ser Arg Gly Ser Asn Met Asn Lys Ser Glu Leu
1               5                   10                  15

Gly Asp Arg Ser Thr Lys Met Lys Gly Lys Ile Cys Ser Ser Tyr Val
            20                  25                  30

Lys Tyr Ile Cys Leu Thr Ile Cys Val Ile Gly Met Leu Cys Ile Lys
        35                  40                  45

Leu Arg Asp Lys Tyr Glu Gly Tyr Ala Ala Ser Gly Ile Gln Asn Asn
    50                  55                  60

Asn Val Tyr Leu Arg Asn Leu Ser Glu Leu Gln Lys Gly Asn Gln Pro
65                  70                  75                  80

Cys Leu Arg His Thr Asn Arg Thr Asp Asn Ser Lys Met Asn Lys Val
                85                  90                  95

Lys Asn Asn Asn Gln Thr Glu Asn Asn Asp Asn Lys Lys Lys Leu Gly
            100                 105                 110

Asn Lys Glu Asp Asn Gln Gly Lys Asn Lys Asn Asn Asn Lys Glu
        115                 120                 125

Lys Gln Asn Asp Ile Asn Lys Arg Gly Thr Gln Asn Thr Glu Thr Lys
    130                 135                 140

Lys Ser Asn Lys Lys Leu Ser Gln Asp Tyr Asn Asp Val Asn Lys Lys
145                 150                 155                 160

Phe Thr Lys Glu Gln Met Lys Asn Leu Val Asn Ser Leu Asp Glu Ile
                165                 170                 175

Pro Pro Arg Asn Asp Met Glu Lys Ile Trp Asn His Ala Val Lys Thr
            180                 185                 190

Ala Asn Ser Gly Thr Ser Arg Ile Lys Lys Leu Lys Glu Tyr Glu
        195                 200                 205

Gln Lys Tyr Gly Arg Cys Tyr Glu Glu Arg Pro Asn Arg Phe Gly Ser
    210                 215                 220

Tyr Glu Gln Val Leu Ile Ser Gln Pro His Glu Phe Asn Glu Arg Leu
225                 230                 235                 240

Lys Val His Glu Asn Asp Tyr Thr Val Phe Phe Tyr Glu Leu Leu Asp
                245                 250                 255

Lys Asp Pro Thr Leu Asp Glu Ile Lys Asn Tyr Ile Thr Ser Phe Leu
            260                 265                 270

Glu Gly Phe Gln Asn Leu Ile Asp Phe Leu Phe Asn Lys Tyr Lys Ile
        275                 280                 285

Ile Phe Leu Gln Thr Thr Thr Glu Ile Pro Ile Asp Gly Thr Ile Tyr
    290                 295                 300

Asp Thr Ser Lys Lys Asp Met Lys Lys Asn Lys Asn Lys Gln Asn
305                 310                 315                 320

Ile Lys Gln Gly Gly Lys Lys Glu Glu Val Lys Gln Glu Gly Lys Lys
                325                 330                 335

Glu Glu Val Lys Gln Glu Gly Lys Lys Glu Glu Val Lys Gln Glu Gly
            340                 345                 350

Lys Lys Glu Glu Val Lys Gln Glu Gly Lys Lys Glu Glu Val Lys Gln
        355                 360                 365
```

```
Gly Gly Lys Lys Glu Glu Val Lys Gln Gly Gly Lys Glu Glu Val
        370                 375                 380

Lys Gln Gly Gly Lys Lys Glu Val Lys Gln Gly Gly Lys Lys Glu
385                 390                 395                 400

Glu Val Lys Gln Gly Gly Lys Lys Glu Val Lys Gln Gly Gly Lys
                405                 410                 415

Lys Glu Glu Val Lys Lys Glu Leu Lys Lys Asn Asn
            420                 425

<210> SEQ ID NO 20
<211> LENGTH: 232
<212> TYPE: PRT
<213> ORGANISM: Plasmodium falciparum

<400> SEQUENCE: 20

Met Leu Phe Ser Phe Lys Tyr Ile Tyr Phe Ser Ser Thr Phe Leu Leu
1               5                   10                  15

Leu Leu Val Leu Gln Ser Lys Thr Lys Tyr Ile Gln Asn Phe Val Asn
            20                  25                  30

Ile Gln Glu Thr Leu Asn Glu Lys Cys Ser Ser Lys Tyr Ile Arg Leu
        35                  40                  45

Ile Ser Glu Gln Thr Ser Asp Glu Ser Thr Ser Lys Ser Ile Lys Asn
    50                  55                  60

Cys Lys Cys Val Asn Lys Arg Asn Asn Lys Asn Gly Asp Asn His Glu
65                  70                  75                  80

Leu Gln Ser Lys Ser Arg Ser Leu Lys Gly Thr Glu Leu Asp Val Thr
                85                  90                  95

Ser Tyr Asn Lys Ser Lys His Thr Gln Gln Asn Asn Leu Gly Asp Ser
            100                 105                 110

Leu Lys Arg Thr Lys Asn Asn Ile Thr Asn Ile Ser Ser Lys Lys Asn
        115                 120                 125

Glu Thr Tyr Leu Phe Asp Glu Asn Thr Asn Glu Tyr Lys Leu Arg Asn
    130                 135                 140

Thr Leu Arg Leu Met Asn Glu Arg Tyr Ala Asp Ser Ile Val Asp Thr
145                 150                 155                 160

Met Asp Leu Asn Asp Lys Thr Lys Asp Lys Phe Lys Lys Phe Leu His
                165                 170                 175

Leu Tyr Met Ala Lys Glu Asn Pro Asp Lys Gln Arg Lys Leu Tyr Glu
            180                 185                 190

Gln Ile Glu Ser Asp Ile Glu Lys Tyr Lys Lys Asn His Val Ile Cys
        195                 200                 205

Ser Ile Val Asp Phe Glu Asn Ile Tyr Asp Ser Phe Tyr Phe Leu Lys
    210                 215                 220

Tyr Glu Asp Arg Tyr Ile Thr Trp
225                 230

<210> SEQ ID NO 21
<211> LENGTH: 6078
<212> TYPE: PRT
<213> ORGANISM: Plasmodium falciparum

<400> SEQUENCE: 21

Met Lys Asn Asn Asp Arg Gly Lys Lys Gly Glu Pro Arg Thr Leu Phe
1               5                   10                  15

Tyr Tyr Glu Ile Tyr Lys Lys Leu Phe Val Tyr Glu Cys Ala Ile
            20                  25                  30
```

-continued

```
Asn Glu Asn Glu Arg Lys Asn Arg Lys Phe Leu Lys Lys Lys Lys
         35                  40                  45

Ser Ile Glu Ser Leu Lys Lys Leu Gln Asp Asp Leu Ile Ile Phe Phe
 50                  55                  60

Asp Asn Asn Ile Asp Leu Met Cys Asp Pro Phe Ser Phe Leu Thr Tyr
 65                  70                  75                  80

Glu Glu Glu Asp Val Asn Lys Thr Leu Lys Asn Tyr Ile Ile Ser
                 85                  90                  95

Asn Tyr Pro Asn Leu Leu Asn Tyr Met Asp Glu Ile Ile Lys Cys Ser
            100                 105                 110

Ile Ile Leu Asn Arg Asn Ala Tyr Tyr Val Cys Thr Leu Phe Asn Asp
            115                 120                 125

Val Tyr Leu Lys Ile Glu Lys Ser Asn Ile Lys Asn Glu Ile Met Lys
        130                 135                 140

Cys Thr Tyr Ile Cys Glu Val Phe Lys Glu Cys Ile Glu Lys Glu Asn
145                 150                 155                 160

Leu Ile Ile Met Ile Tyr Met Glu Ile Leu Lys Tyr Ile Asn Lys Asn
                165                 170                 175

Glu Arg Ile Gly Val Ser Leu Asn Asn Lys Asn Asp Gly Lys Tyr Gln
            180                 185                 190

Lys Tyr Glu Glu Thr Asn Ile Ser Thr Asp Lys Asp Asn Asn Ser
        195                 200                 205

Ser Asp Asp Asn Asn Gly Ile Ile Lys Lys Asn Glu Glu Val Lys Thr
210                 215                 220

Ser Ser Val His Ser Thr Thr Ser Asn Ile Asn Ser Val Gly Ser Leu
225                 230                 235                 240

Asn Ile Ser Lys Thr Val Cys Glu Asn Asn Ile Asn Asn Asn Arg Val
                245                 250                 255

Asn Ser Asp Arg Phe Ser Leu Tyr Ile Leu Ile Leu Thr Gln Asn
            260                 265                 270

Asp Phe Ile Asp Asn Ile Phe Leu Glu Ile Asp Arg Ile Ile Lys Phe
        275                 280                 285

Leu Ile Lys Tyr Asp Asp Ile Cys Asp Gln Ile Asn Tyr Val Phe Asn
290                 295                 300

Tyr Lys Thr His Lys Ile Asn Ile Leu Phe Asn Leu Leu Asp Ile Leu
305                 310                 315                 320

Phe Leu Tyr Phe Ser Lys Phe Gln Ala Thr Thr Gln Ile Ile Ser Arg
                325                 330                 335

Ile Phe Lys Leu Leu Asn His Leu Val Ser Ser Lys Tyr Phe Asp Phe
            340                 345                 350

Met Pro Thr Asp Gln Tyr Val Lys Glu Leu Asp Asn Ile Leu Phe Trp
        355                 360                 365

Thr Asp Tyr Lys Lys Lys Lys Phe Phe Thr Tyr Leu Lys Asn Ile
370                 375                 380

Arg Ser Asn Lys Ile Ile Ser His Ile Asp Asp Tyr Tyr Lys Leu Asp
385                 390                 395                 400

Ile Asn Ile Ser Asp Asp Pro Phe Met Thr Lys Phe Met Asp Phe Asn
                405                 410                 415

Asp Ser Ser Ala Val Met Lys Asn Asn Asn Thr Ile Ala Asp Asn Asn
            420                 425                 430

Asn Met Asn Asn Ile Asn Thr Asn Met Asp Ser Asn Met Asp Asn Asn
        435                 440                 445

Ile Asn Asn Asn Ile Asn Ser Asn Ile Asn Asn Asn Ile Asn Ser Asn
450                 455                 460
```

-continued

```
Ile Asn Asn Asn Ile Asn Ser Asn Ile Asn Asn Asn Ile Asn Ser Asn
465                 470                 475                 480
Ile Asn Asn Asn Pro Leu Ser Ser Ala Thr Asn Met Phe Thr Gly
                485                 490                 495
Thr Asn Asn Thr Asn Pro Asn Ile Asn Thr Ser Gly Ile Leu Lys
            500                 505                 510
Asn Asn Asn Phe Asn Met Gln Ser Leu Pro Gln Ser Asn Phe Gly Asn
            515                 520                 525
Asp Asn Asn Val Ile Lys Ser Asn Glu Thr Ser Thr Ser Ser Asn Met
530                 535                 540
Ser Asn Asn Leu Leu Ser Asn Leu Lys Thr Gln Gln Gln Asn Asn Asn
545                 550                 555                 560
Ala Ile Asn Thr Asn Met Leu Gly Cys Asn Gln Glu Lys Asn Glu Lys
                565                 570                 575
Gln Asp Arg Asn Ile Asn Ile Ser Val Lys Asn Thr Asn Ser Glu Val
            580                 585                 590
Ile Arg Asp Phe Pro Phe Asp Ile Asn Asn Leu Trp Lys Asp Lys Lys
            595                 600                 605
Lys Trp Asn Ile Tyr Asp Gln Tyr Asn Lys Asn Tyr Asn Asn Leu Glu
            610                 615                 620
Lys Cys Ile Asp Cys Asn Gly Phe Trp Tyr Asn Cys Asn Cys Ser Leu
625                 630                 635                 640
Ser Asp Gly Asn Ile Ser Ser Leu Thr Leu Thr Thr Gln Ile Ser Leu
                645                 650                 655
Leu Leu Ile Leu Cys Leu Tyr Pro Asn Val Asp Lys Tyr Val Tyr Glu
            660                 665                 670
Lys Lys Lys Lys Ile Pro Ser Asp Ile Ile Ser Asn Asn Ile Asn Asn
            675                 680                 685
Lys Ser Ser Asp Asp Lys Thr Thr Asp Ile Ile Asn Asp Gly Lys Glu
690                 695                 700
Lys Val Asn Phe Ser Asn Phe Tyr Ser Pro Asp Ile Trp Lys Phe Asn
705                 710                 715                 720
Cys Met Ser Ser Gln Lys Asp Leu Lys His Leu Leu Asn Val Lys Asp
                725                 730                 735
Ser Tyr Ser Val Ser Thr Glu Phe Ile Asn Glu Asn Val Ser Tyr Tyr
            740                 745                 750
Tyr Asp Leu Phe Thr Lys Ile Phe Glu Lys Asn Asn Lys Lys Lys Lys
            755                 760                 765
Asn Ala Lys Met Asp Asn Asn Asn Asn Asn Asn Asn Asn Asn Asn Asn
770                 775                 780
Lys Asn Asn Asp Asp Asp Phe Trp Asn Tyr Val Asn Lys Ser Gly
785                 790                 795                 800
Asn His Met Leu Leu Lys Asn Asn Ile Asn Asn Asn Asp Asp Ala
                805                 810                 815
Leu Val Asp Ser Val Tyr Gly Asp Ile Glu Lys Tyr Val Gln Tyr Asn
            820                 825                 830
His Asn Asn Asn Ser Glu Lys Asn Cys Tyr Glu Asn Val Ile Ile Leu
            835                 840                 845
Lys Tyr Met Val Ser Leu Phe Ser Asn Lys Asp Glu Ile Phe Ala
            850                 855                 860
Ser Ile Phe Glu Asp Asn Phe Phe Lys Val Ala Tyr Asp Val Ile Leu
865                 870                 875                 880
Lys Lys Ile Thr Ser Ala Thr Leu Ile Gly Thr Leu Ile Phe His Leu
```

-continued

```
                    885                 890                 895
Phe His Met Thr Phe Ser Phe Ser Phe Ile Lys Asn Tyr Lys Thr Thr
            900                 905                 910
Asp Leu Trp Asn Ser Leu Ile Asp Tyr His Ile Lys Arg Asp Phe His
            915                 920                 925
Ser Lys Lys Arg Asn Ala Arg Ile Gly Asn His Met Thr Asp Met Asn
            930                 935                 940
Asp Val Glu Tyr Asn Lys Lys Ser Ile Asp Ser Lys Gly Met Phe Tyr
945                 950                 955                 960
Asn Thr His Gly Phe Val Lys Met Met Thr Asp Asp Lys Ser Phe
            965                 970                 975
Gly Asp Thr Lys Gly Val Gly Asp Thr Lys Gly Phe Gly Asp Asn Ser
            980                 985                 990
Phe Leu Phe Asn Asn Arg Ser Gly Tyr Asp Ile Tyr Thr Asn Asn Glu
            995                 1000                1005
Ile Asn Asn Lys Met Arg His Gly Leu Asp Asn Asn Asn Asn
    1010                1015                1020
Ile His Leu Asn Ser Ser Tyr Tyr Asn Asn Ile Ile Tyr Ile Tyr
    1025                1030                1035
Lys Lys Lys Gly Glu Tyr Leu Ile Asp Ile Leu Asn Phe Leu Lys
    1040                1045                1050
Ile Leu Cys Asn Asn Tyr Pro Arg Leu Val Asn Lys Tyr Val Cys
    1055                1060                1065
Ile Leu Lys Asn Ile Ile Asn Arg Tyr His Ser Arg Ile Met Glu
    1070                1075                1080
Phe Ser Glu Ile Asp Glu Thr Ile Tyr His His Asn Leu Glu His
    1085                1090                1095
Met Asn Gln Asp Ile Asp His Arg Gly His Val Asp Asp Ile Glu
    1100                1105                1110
Asn Asp Phe Tyr Tyr His Gly His Gly Pro Met Asn Lys Lys His
    1115                1120                1125
Tyr Met Gly Lys Gln Asn Lys Phe Tyr Asn Ile Asn Glu Glu Arg
    1130                1135                1140
Arg Met Val Leu Met Lys Tyr Arg Ser Leu Lys Ile Val Ala Glu
    1145                1150                1155
Asp Lys Met Lys Leu Cys Leu Asp Phe Tyr Ser Asp Ile Phe Val
    1160                1165                1170
His Val Leu Asp Phe Ala Ser Val Leu Cys Asn Asn Ile Tyr Asp
    1175                1180                1185
Leu Arg Val Ile Glu Asn Val Val Leu Cys Phe Lys Thr Pro Leu
    1190                1195                1200
Thr Ala Asn Leu Asn Ile Phe Asn Leu Thr Lys Lys Leu Phe Asn
    1205                1210                1215
Gln Phe Asn Cys Val Leu Ala Gly Lys Tyr His Glu Phe Ser Lys
    1220                1225                1230
Ile Thr Asn Lys Gln His Met His Asp Lys Thr Arg Asn Asn Asn
    1235                1240                1245
Asn Met Lys Asn Asp Leu Gly Met Met Asp Tyr His Ile Asn Ser
    1250                1255                1260
Met Lys Ser Asn His Ile Ser Ser Asn Asn Asn Asn Asn Asn
    1265                1270                1275
Asn Asn Asn Asn Asn Asn Asn Asn Asn Ser Asn Asn Asn Asn
    1280                1285                1290
```

-continued

```
Asn Asp Asn Asn Arg Ser Arg Tyr Ser Ile Ser Asn Asn Gln Leu
1295             1300                1305

Asn His Ile Lys Phe His Lys Asp Leu Tyr Lys Ile Leu Leu Glu
1310             1315                1320

Arg Lys Ile Ile Asn Pro Tyr Asn Asn Met Ser Ser Leu Gln Glu
1325             1330                1335

Gly Lys Asn Ser Ser Asn Ile Asn Asp Asn Tyr Asp Asp Asp Phe
1340             1345                1350

Phe Ser Asn Tyr Tyr Phe Ile Tyr Leu Tyr Tyr Phe Lys Ile Asn
1355             1360                1365

Leu Leu Gln Lys Ile Phe Gln Gln Asn Asn Phe Leu Lys Asp Ile
1370             1375                1380

Leu Arg Asn Tyr Asn Ile Leu Asp Leu Leu Glu Lys Asn Asn Val
1385             1390                1395

Tyr Leu Asn Asn Leu Ile Lys Glu Asn Gly Leu Ile Glu Glu His
1400             1405                1410

Leu Lys Asn Lys Lys Ile Phe Gln Glu Cys Phe Gln Ser Tyr Asp
1415             1420                1425

Ile Phe Asn Lys Met Val Leu Ser Gln Asn Asp Glu Tyr Ser Asn
1430             1435                1440

Ser Ile Arg Asp Ala Asn Lys Ile Leu Met Asn Ile Asp Glu Asn
1445             1450                1455

Asn Asn Lys Leu Lys Ser Phe Val Asn Phe Asn Gly Leu Asn Glu
1460             1465                1470

Val Gln Gln Asn Val Leu Asn Glu Leu Phe Pro Asn Val Ser Met
1475             1480                1485

Ser Ile Asn Gly Asn Thr Ile Gln Pro Pro Asn Asn Asn Asn
1490             1495                1500

Asn Asn Asn Asn Asn Asn Asn Asn Asn Asn Asn Asn Asn Val Val
1505             1510                1515

Ser Asn Met Asn Met Leu Asn Asn Leu Gly Pro Ser Ser Gly Pro
1520             1525                1530

Ile Thr Leu Asn Gly Phe Asn Asn Asn Met Asn Ser Ser Met Asn
1535             1540                1545

Ser Asn Asn Asn Ser Thr Asn Ile His Pro Phe Gly Asp Lys Ser
1550             1555                1560

Phe Leu Glu Asn Ile Leu Asn Glu Gln Asn Cys Ile Asn Tyr Leu
1565             1570                1575

Leu Ile Glu Asp Lys Leu Thr Glu Asn Leu Leu Arg Glu Asn Asn
1580             1585                1590

Phe Leu Lys Cys Glu Phe Thr Lys Tyr Asn Ile Val Asp Leu Phe
1595             1600                1605

Tyr Lys Asn Lys Val Ser Glu Thr Leu Leu Asp Asn Leu Lys Ser
1610             1615                1620

Ile Met Leu Asn Glu Tyr Asp Leu Leu Glu Ile Leu Ser Cys Glu
1625             1630                1635

Lys Lys Phe Arg Asn Met Asn Arg Asn Val Asp Gly Ser Tyr Asn
1640             1645                1650

Glu Lys Glu Ala Ile Gln Ile Phe Phe Asp Asp Asn Lys Asp Ala
1655             1660                1665

Val Asp Phe Phe Lys Glu Lys Lys Tyr Gln Ser His Leu Phe Asn
1670             1675                1680

Asn Asn Asn Glu Glu Asp Asp Tyr Asp Asp Glu Asp Asp Asn Asp
1685             1690                1695
```

-continued

Asp Glu Asp Asp Asn Asp Asp Gly Arg Ile His Leu Asn Gln His
      1700                1705                1710

Thr Tyr Leu Pro Asn Asn Asn Ser Leu Met Asn Arg Ala Lys Ile
      1715                1720                1725

Ile Leu Arg Thr Glu Leu Glu Tyr Glu Lys Lys His Ile Ile Ile
      1730                1735                1740

Asp Thr His Tyr Leu Leu Lys Asn Ile Phe Glu Lys Asn Leu Tyr
      1745                1750                1755

Pro Tyr Asn Cys Leu Lys Met Leu Glu Lys Cys Leu Leu Phe Leu
      1760                1765                1770

Ser Ser Val Asn Asn Lys Leu Cys Tyr Tyr Leu Pro Ile Asn
      1775                1780                1785

Lys Asn Leu Leu Ile Asp Tyr Ile Leu Leu Glu Gln Tyr Glu Asn
      1790                1795                1800

Asn Ala Thr Tyr Thr Thr Asn Met Ser Lys Thr Thr Asp Asp Lys
      1805                1810                1815

Ile Asn Gln Lys Asp Thr Tyr Asn Lys Thr Gln Asp Glu His Asn
      1820                1825                1830

Arg Phe Phe Lys Ile Lys Asn Lys Lys Tyr Asn Asn Phe Leu Ser
      1835                1840                1845

Leu Leu Asp Ile Gln Asn Met Asn Asn Thr Thr Asn Tyr Lys Asn
      1850                1855                1860

Val Phe Ile His Asn Leu Asn Met Ser Lys Lys Ile Lys Asp Glu
      1865                1870                1875

Lys Glu Lys Asn Ile Lys Gln Tyr Lys Thr Met His Leu Leu Asp
      1880                1885                1890

Ile Leu Tyr Asp Ile Ile Lys Thr Lys Tyr Asn Ala Ser Val Asp
      1895                1900                1905

Ile Ser Asn Leu Lys Cys Leu Cys Ile Glu Ile Leu Cys Ser Ser
      1910                1915                1920

Phe Val Lys Asn Ser Ser Ser Ala Leu Ser Val Leu Cys Thr Leu
      1925                1930                1935

Thr Gln Ile Phe Pro Asp Ile Phe Phe Glu Thr Met Lys Lys Tyr
      1940                1945                1950

Thr Glu His Asn Asp Ile Leu Lys Lys Lys Leu Glu Tyr Ile Asp
      1955                1960                1965

Lys Gln Leu Leu Leu Gly Gln Ile Lys Asn Glu Thr Leu His Gln
      1970                1975                1980

Ile Ala Gln Asn Phe His Gln Pro Thr Phe Asn Leu Lys Ile Ile
      1985                1990                1995

Ile Thr Phe Met Lys Cys Val Asn Tyr Leu Leu Tyr Met Ile Gly
      2000                2005                2010

Ile Lys Arg Lys Phe Asn Met Ser Leu Ser Arg Ile Trp Tyr Phe
      2015                2020                2025

Phe Asn Asn Ile Asp Lys Ile Glu Glu Ile Asp Glu Lys Ile Lys
      2030                2035                2040

Arg Arg Lys Leu Asn His Thr Asn Gln Gln Tyr Met Asp Thr Gln
      2045                2050                2055

His Leu Lys Glu Gly Ile Asn Gln Asn Asn His Tyr Asp His Asp
      2060                2065                2070

Lys Lys Lys Ser Ser Ser Ser Tyr Ile Phe Phe Asp Val Phe Phe
      2075                2080                2085

Asn Phe Asp Leu Phe Phe Asp Glu Leu Glu Lys Glu Asp Asp Gln

-continued

```
                2090                2095                2100

Asp Glu Gly Ile Gly Tyr Asn Glu His Gly Tyr Asn Ser Asn Lys
    2105                2110                2115

Lys Lys Asn Ser Asn Asn Val Asp His Asp Asn Ile Asn Asn
    2120                2125                2130

Asn Val Asp Val Tyr Gly Arg Glu Lys Tyr Asn Thr Asp Thr Tyr
    2135                2140                2145

Leu Asn Glu Asp His Val Leu Thr Asn Lys Asn Gln Asn Thr Ile
    2150                2155                2160

Tyr Gly Asn Asn Lys Glu Lys Leu Lys Asp Met Pro Tyr Asp Asn
    2165                2170                2175

Asn Tyr Asn Asp Gly Gly His His Asp His Asp Asn Asn Asn Asp
    2180                2185                2190

His Asn Asn Asp Met Tyr Asn Asn Cys Leu Lys Lys Lys Leu Met
    2195                2200                2205

Ile Ser Asp Asp Glu Lys Asn Ile Cys Lys His Leu Ile Leu Leu
    2210                2215                2220

Thr Asn Tyr Ile Val Gln Asp Ile Phe Tyr Asn Leu Ile Asn Asn
    2225                2230                2235

Phe Ile Leu Lys Lys Ile Lys Glu Lys Lys Tyr Glu Lys Glu Asp
    2240                2245                2250

Leu Leu Glu Glu His Ile Lys Trp Glu Ile Leu Met Asn Lys Gln
    2255                2260                2265

Glu Asn Ser Phe Phe Lys Arg Arg Tyr Asn Phe Tyr Met His Lys
    2270                2275                2280

Ser Lys His Ile Glu Leu Gln Ile Asn Gln Met Gln Asn Gln Ile
    2285                2290                2295

Asn Ile Asn Asn Thr Ser Ile Val Gln Leu Glu Asn Val Leu Lys
    2300                2305                2310

Gln Asn Asn Val Pro Phe Glu Pro Tyr Ile Ile Ser Gln Arg Met
    2315                2320                2325

Phe Asp Lys Ser Phe Ala Asp Thr Asn His Thr Ile Asn Asn Asn
    2330                2335                2340

Met Gly His Asn Tyr Asn Thr Pro Gly Ile Ile Thr Ser Asn Leu
    2345                2350                2355

Leu Thr Asn Ser Ser Gln Ala Asn Asn Gln Asn Asn Ser Ser Ala
    2360                2365                2370

Leu Ser Gly Ile Asn Met Ser Ser Leu Leu Asp Asn Lys Ser Arg
    2375                2380                2385

Ser Thr Asn Phe Phe Ser Thr Asn Thr Phe Asn Gln Ala Asn Asn
    2390                2395                2400

Ile Ser Pro Phe Ser Gly Val Asn Ser Asn Asn Asn Asn Asn Asn
    2405                2410                2415

Val Asn Ser Asn Val Asn Ser Asn Leu Asn Asn Asn Val Asn Ser
    2420                2425                2430

Pro Leu Ser Met Phe Gly Thr Thr Val Ser Pro Ser Leu Asp
    2435                2440                2445

Asn Thr Arg Thr Asn Tyr Glu Ser Ser Met Arg Val Ala Ser Tyr
    2450                2455                2460

Ser Gln Gly Thr Asn Ala Thr Ile Asn Asn Thr Asn Thr Gly Gly
    2465                2470                2475

Asn Ile Phe Ser Ser Pro Leu Ser Asn Ser Leu Asn Gln Gly Ile
    2480                2485                2490
```

```
Thr Asn Ala Asn Ala Asn Ala Asn Thr Ile Thr Asn Thr Asn Ala
2495                2500                2505

Asn Asn Ile Phe Asn Ile Ser Ser Asn Ser Ala Leu Leu Asn Asn
2510                2515                2520

Ser Ser Asn Lys Leu Phe Gly Thr Thr Thr Asn Thr Ala Ser Ser
2525                2530                2535

Ser Asn Leu Leu Gly Asn Asn Asn Ile Ser Ser Gly Met Phe Ser
2540                2545                2550

Pro Leu Ser Asn Asn Ile Asn Asn Lys Pro Asn Leu Phe Ser Gly
2555                2560                2565

Ala Asn Gln Asn Asn Leu Phe Ser Asn Thr Asn Met Ser Ser Ser
2570                2575                2580

Pro Ser Leu Ser Leu Asn Asn Thr Thr Asn Thr Ile Gly Gly Asn
2585                2590                2595

Ile Asn Ser Ser Gly Gln Asn Phe Ile Gln Asn Gln Asn Asn Ile
2600                2605                2610

Leu Thr Asn Gln Thr Leu Ser Asn Ser Ile Tyr Asn Asn Asn Ser
2615                2620                2625

Asn Leu Asn Ser Asn Asn Leu Leu Leu Pro Gly Gln Gln Gln Asn
2630                2635                2640

Asn Thr Ser Pro Phe Leu Thr Asn Met Gly Thr Asn Ala Ser Ser
2645                2650                2655

Pro Thr Ser Ser Ile Phe Asn Gln Ser Lys Asp Leu Ile Ser Ser
2660                2665                2670

Asn Asn Leu Asn Ile Gly Thr Ser Thr Thr Asn Ile Phe Gly Thr
2675                2680                2685

Thr Ser Ser Asn Asn Met Asn Asn Met Asn Ser Met Asn Ser Met
2690                2695                2700

Asn Ser Met Asn Asn Met Asn Ser Met Asn Ser Leu Phe Leu Gly
2705                2710                2715

Leu Gln Gln Gln Thr Gln Ser Thr Thr Thr Thr Asn Asn Asn
2720                2725                2730

Asn Asn Asn Asn Ile Phe Ser Ser Ser Gly Asn Thr Asn Asn Met
2735                2740                2745

Ser Leu Phe Asn Asn Pro Asn Gly Leu Arg Asn Asn Met Phe Thr
2750                2755                2760

Ser Thr Asn Pro Leu Asn Ala Ser Ser Thr Asn Asn Leu Asn Ser
2765                2770                2775

Asn Asn Asn Met Asn Gln Ala Pro Ser Leu Phe Ser Asn Ile Thr
2780                2785                2790

Phe Asn Met Phe Asn Asn Asn Asn Asn Ser Asn Ile Asn Asn Met
2795                2800                2805

Asn Asn Met Asn Asn Met Asn Asn Val Asn Asn Val Asn Asn Asn
2810                2815                2820

Asn Val Asn Met Pro Gln Phe Asn Asn Ile Glu Glu Leu Lys Arg
2825                2830                2835

Tyr Tyr Glu Asp Leu Lys Leu Lys Thr Asn Val Leu Asn Ala Glu
2840                2845                2850

Val Tyr Lys Tyr Lys Ile Glu Leu Lys Lys Asn Glu Tyr Asn Leu
2855                2860                2865

Asn Lys Asp Lys Lys Ile Gln Leu Leu Lys Glu Asn Lys Leu Arg
2870                2875                2880

Glu Asn Lys Ser Lys Ser Asp Ile Asn Phe Lys Asp Asn Glu Met
2885                2890                2895
```

Tyr Ile Leu Ile Ile Leu Val Phe Met Tyr Phe Lys Leu Ile Leu
    2900                2905                2910

Lys Gly Pro Leu Pro Asn Asp Asn Asn Asn Lys Gln Leu Asn
    2915                2920                2925

Arg Val Met Asn Glu Arg Tyr Asp Tyr Leu Cys Asp Phe Arg Pro
    2930                2935                2940

Thr Met Tyr Leu Phe Glu Gln Ile Leu Gly Ser Asn Lys Phe
    2945                2950                2955

Met Asn Leu Phe Phe Asn Ile Ile Phe Leu Asp Asn Ile Ile His
    2960                2965                2970

Glu Glu Asn Lys Asn Met Glu Glu Leu Leu Lys Cys Lys Asn
    2975                2980                2985

Tyr Cys Asp Phe Ile Asn Val Cys Asn Gln Glu Lys Ser Phe Phe
    2990                2995                3000

Phe Lys Lys Lys Asn Leu Tyr Asp Asp Thr Lys Asn Thr Thr Lys
    3005                3010                3015

Leu Lys Asn Thr Lys Asp Tyr His Asn Glu Asn Asn Lys Asp Ser
    3020                3025                3030

Asp Asn Lys Gln Asn Phe Lys Asn Thr Ser Ile Asp Val Asp Ser
    3035                3040                3045

Asn Asn Asn Ile Phe Thr Ser Met Thr Ser Glu Ile Phe Phe Asn
    3050                3055                3060

Lys Lys Leu Gln Tyr Leu Thr Cys Ser Tyr Ser Lys Glu Tyr Tyr
    3065                3070                3075

Asn Ser Leu Phe Phe Tyr Lys Ile Lys Ser Leu Gly Leu Gly Ile
    3080                3085                3090

Leu Lys Leu Leu Phe Glu Arg Asp Val Leu Phe Ile His Met Tyr
    3095                3100                3105

Lys Leu Trp Lys Asn Glu Lys Leu Leu Lys Lys Arg Met Asp Lys
    3110                3115                3120

Tyr Lys Phe Asp Leu Asn Ile Ile Asp Pro Asn Asn Asn Asp Asp
    3125                3130                3135

Asn Lys Asn Asn Asp Asn Asn Lys Asn Asn Asp Asp Asp Lys Asn
    3140                3145                3150

Asn Asp Lys Asn Asn Asp Asp Asp Asp Asp Asp Asn Met Lys
    3155                3160                3165

Lys Arg Gly Pro Ser Thr Glu Tyr Leu Glu Lys Lys Leu Asn Met
    3170                3175                3180

Thr Glu Ser Leu Cys Ser Pro Ile Cys Val His Asn Phe Leu Phe
    3185                3190                3195

Lys Asn Ile Asn Ile Asn Ser Arg Thr Thr Tyr Leu Ile Leu Leu
    3200                3205                3210

Leu Lys Asn Phe Phe Arg Asp Asn Glu Met Asn Lys Val Ile Ile
    3215                3220                3225

Tyr Phe Ile Leu Gln Ile Phe Ile Arg Asp Cys Lys Thr Thr Ile
    3230                3235                3240

Asn Ile Leu Lys Arg Asp Asn Glu Ser Phe Asn Phe Leu Lys Tyr
    3245                3250                3255

Ala Leu Arg Ser Ile Phe Ile Tyr Asn Leu Asn Lys Gln Lys Phe
    3260                3265                3270

Asn Asn Cys Phe Ile Ile Ser Asn Arg Thr Ile Lys Met Lys Asn
    3275                3280                3285

Ile Ile Asn Asn Phe Val Asp Leu Pro Leu Leu Tyr Phe Leu Lys

```
                3290                3295                3300

Asn Ser Lys Asp Val Lys Asn Lys Met Leu Leu Arg Asn Leu Lys
        3305                3310                3315

Asn Lys Leu Asp Lys His Arg Asp Ser Gly His Leu Glu Asn Lys
        3320                3325                3330

Lys Ser Val Leu Asn Thr Thr Asn Trp Leu Ser Tyr Met Asn Lys
        3335                3340                3345

Gly Asn Tyr Glu Asn Val Glu Glu Gly Asn His Val Asp Asp Ala
        3350                3355                3360

Asp Gly Asp Tyr Asp Gly Glu Asp Asp Val Glu Asp Asp Asp Asp
        3365                3370                3375

Asp Asp Asp Val Glu Asp Asp Asp Glu Asp Asp Gly Glu Asp
        3380                3385                3390

Asp Asp Asp Asp Glu Asp Asp Asp Glu Asp Asp Asp Asp Asp Asp
        3395                3400                3405

Glu Asp Asp Asp Ile Phe Tyr Ser Lys His Pro Ser Asn Asn Leu
        3410                3415                3420

Lys Lys Lys Gln Asn Lys Gly Thr Arg Lys Ser Val Leu His Leu
        3425                3430                3435

Lys Thr Glu Met Tyr Asn Lys Met Lys Tyr Leu Asn Asn Arg Gln
        3440                3445                3450

Arg Lys Met Lys Lys Lys Asn Lys Phe Gly Tyr Asn Asn Val Glu
        3455                3460                3465

Asn Asn Ile Asp Phe Asp Glu Asn Val Asp Tyr Asn Gly Phe Ile
        3470                3475                3480

Ser Lys Tyr Lys Asn Met Lys Leu Arg Glu Lys Tyr Glu Ser Lys
        3485                3490                3495

Tyr Ile Tyr Asp Tyr Leu Ser Asp Asn Asp Leu Ile Asp Thr Ile
        3500                3505                3510

Lys Ser Lys Lys Ile Cys Val Phe Tyr Asp Asn Lys Glu Lys Glu
        3515                3520                3525

Asp Glu Asn Glu Asn Phe Ser Leu Tyr Asn Ser Ile Ser Glu Asn
        3530                3535                3540

Phe Asn Asp Gly Tyr Ser Lys Ile Asp Tyr Tyr Asn Glu Ile Lys
        3545                3550                3555

Ser Leu Asp Tyr Asn Ile Ile Gly Tyr Cys Ser Ser Tyr Asn Phe
        3560                3565                3570

Leu Pro Ile Asn Asn Phe Tyr Thr Glu Lys Tyr Asp Phe Ile Glu
        3575                3580                3585

Asn Glu Leu Val Tyr Met Ser Asp Leu Lys Leu Tyr Phe Tyr Val
        3590                3595                3600

Lys Ser Phe Lys Arg His Thr Tyr Phe Thr Lys Leu Leu Asn Ile
        3605                3610                3615

Glu Asn Val Gly Lys Lys Asn Tyr Asp Lys Glu Gly Ile Tyr
        3620                3625                3630

Lys Asn Val Asp Ile Asp Tyr Tyr Asn Met Asp Asn Glu Asn Asn
        3635                3640                3645

Ile Met Asn Asn Asn Tyr Asn Asn Asn Asn Asn Asn Asn Asn Asn
        3650                3655                3660

Asn Asn Ile Ile Asn Asp Lys Asn Ile Tyr Asn Ile Asn Lys Glu
        3665                3670                3675

Asn Asp Leu Asn Ser Val Asn Gln Lys Met Asn Thr Asn His Asp
        3680                3685                3690
```

-continued

| | | | | | | | | | | | |
|---|---|---|---|---|---|---|---|---|---|---|---|
| Met | Asn | Leu | Asn | Leu | Val | Lys | Asn | Glu | Ile | Ala | Leu | Asn | Asn | Thr |
| | 3695 | | | | 3700 | | | | | 3705 | | | | |

Met Asn Leu Asn Leu Val Lys Asn Glu Ile Ala Leu Asn Asn Thr
3695                3700               3705

Asp Gly Asn Lys Lys Gln Ile Asp Glu Leu Asn Glu Ala Ile Ser
3710                3715               3720

Tyr Ile Lys Asn Asp Ser Tyr Ile Lys Thr Asp Ala Ser Asn Asn
3725                3730               3735

Ile Glu Gln Ile Ile Asp Asn Glu Ile Lys Tyr Tyr Asp Phe Phe
3740                3745               3750

Asn Lys Leu Asn Lys Met Asn Glu Asn Leu Leu Phe Ser Asn Ile
3755                3760               3765

Leu Gln Asn Ser Arg Glu Asp Lys Ile Lys Tyr Leu Glu Tyr Ile
3770                3775               3780

Lys Ser Ile Val Glu Asn Asp Lys Lys Tyr Asp Pro Asn Asn Ile
3785                3790               3795

His Gly Asn Asn Asn Asn Asn Asn Asn Asn Asn Ser Asn Lys
3800                3805               3810

Leu Asn Asn Asn Leu Leu His Pro Leu Ile Asp Leu Leu Gln Ala
3815                3820               3825

Lys Lys Lys Glu Thr Glu Lys Lys Ile Ser Asn Glu Leu Arg Lys
3830                3835               3840

Lys Asn Ile Phe Met Asn Asn Glu Leu Cys Glu Trp Ile Glu Leu
3845                3850               3855

Ser His Leu Leu Asn Ile Asp Ile Asp Tyr Asn Asp Ile Arg Asn
3860                3865               3870

Ile Asn Lys Lys Lys Ile Leu Asn Asn Tyr Ser Lys Thr Pro
3875                3880               3885

Ile Thr Lys Leu Ile Leu Tyr Phe Tyr Glu Ile Ile Thr Arg Lys
3890                3895               3900

Tyr Leu Phe Leu Asn Asn Ser Asn Ala Asn Ser Asn Ala Arg Ser
3905                3910               3915

Asp Ser Arg Ser Asp Ser Leu Ile Glu Asn Cys Ile Leu Ser Leu
3920                3925               3930

Leu Gly Leu Ser Phe Ile Pro Ser Lys Asn Val Glu Lys Lys Arg
3935                3940               3945

Thr Met Ser Ser Asn Met Glu Glu Gly Leu Glu Leu Glu Asn Asp
3950                3955               3960

Cys Phe Leu Asn Cys Leu Ile Lys Glu Ile Val Ile Lys Phe Ser
3965                3970               3975

Ser Tyr Asp Asn Ile Ser Glu Leu Ile Phe Val Asp Tyr Tyr Asp
3980                3985               3990

Glu Lys Asp Ser Phe Tyr Lys Cys Asn Ile Leu Lys Asp Gly Lys
3995                4000               4005

Thr Lys Lys Gly His Met Val Lys Lys Asn Arg Lys Gly Ile Asp
4010                4015               4020

Leu Pro Asp Asp Met Lys Lys Asn Val Tyr Glu Asn Met Arg Ser
4025                4030               4035

Gly Asp Asn Tyr Asp Asp Asn Asn Tyr Glu Asp Asp Asn Asn
4040                4045               4050

Tyr Glu Asp Asp Asn Asn His Asp Asp Asp Asp Asn Asn Asn
4055                4060               4065

Tyr Leu Tyr Asp Lys Asn Gln Leu Arg Lys Gly Asn Lys Cys Phe
4070                4075               4080

Asp Asp Lys Asn Tyr Tyr Thr Ser Asn Leu Leu Lys Arg Tyr Glu
4085                4090               4095

-continued

```
Ser Lys Asp Tyr Tyr Lys Lys Asn Ile Phe Leu Asn  Asn Ile Asn
4100            4105                4110

Asn Ile Lys Gln Tyr Asn Ile Phe Glu Lys Asn Ser  Tyr Phe Ile
4115            4120                4125

Lys Ser Leu Asn Ile Ile Tyr Met Leu Ser Arg Asn  Lys Lys Met
4130            4135                4140

Lys Asp Tyr Ile Ile Ser Phe Ile Asn Lys Met Trp  Ile Asn Lys
4145            4150                4155

Phe Asn Val Phe Tyr Tyr Ile Thr Gln His Val Asn  Ile His Lys
4160            4165                4170

Leu Lys Asp Thr Glu Lys Ile Leu Phe Tyr Lys Ile  Ser Phe His
4175            4180                4185

Met Leu Asn Ile Phe Ile Pro Ile Ile Asp Tyr Ile  Leu Asn Asn
4190            4195                4200

Ile Asp Lys Tyr Val Glu Cys Phe Met Asp Ile Asn  Phe Ile Ser
4205            4210                4215

Asp Thr Trp Glu Asn Asn Gln Lys Glu Asn Lys  Lys Gln Gln
4220            4225                4230

Asn Val Asn Lys Asp Gly Ile Asn Asn Val His Lys  Asn Ser Leu
4235            4240                4245

Glu Glu Gly Lys Lys His Thr Gln Lys Tyr Thr Gln  Lys Glu Lys
4250            4255                4260

Lys Asn Tyr Thr Asn Asn Ile Tyr Asp Ile Ile Asn  Lys Asp Asn
4265            4270                4275

Phe Asp Glu Lys Lys Asn Ile Phe Glu Phe Leu Asn  Pro Ile Phe
4280            4285                4290

Asn Tyr Asp Asn Val Gln Asn Phe Ile Asn His Tyr  Ile His Ile
4295            4300                4305

Ile Lys Asn Tyr Asn Asp Thr Tyr Leu Lys His Tyr  Ile Tyr His
4310            4315                4320

Tyr Tyr Leu Phe Asn Tyr Asp Phe Thr Phe Gln Asn  Val Tyr Asn
4325            4330                4335

Tyr Ser Asn Ile Glu His Ile His Tyr Ile Lys Asn  Glu Thr Asn
4340            4345                4350

Pro Pro Pro Cys Ser Asn Asn Asn Asn Asn Ile Asn  Lys Tyr Asn
4355            4360                4365

Asn Asn Asn Asn Asn Asn Val His Leu Leu Tyr Thr  Ser Ile Ile
4370            4375                4380

Asn Thr Tyr Val Asn Phe Cys Ala Cys Pro Thr Lys  Leu Asn Gln
4385            4390                4395

Tyr Asn Ser Ser Asn Asn Asn Arg Ile Ser Gln Tyr  Lys Phe Leu
4400            4405                4410

Tyr Asp Asn Tyr Cys Met Tyr Asn Asn Gln Asn Cys  Gly Ser Asn
4415            4420                4425

Glu Leu Glu Asp Gly Leu Gln Ser Asn Lys Arg Lys  Asp Lys Lys
4430            4435                4440

Lys Lys Asn Tyr Asn Asn Asn Asn Asn Asn Asn  Asn Asn Glu
4445            4450                4455

His Met Phe Asp Ser Tyr Tyr Ile Asn Lys Val Glu  Glu Asp Glu
4460            4465                4470

Ile Asp Ser Ile Gly Asp Ser Arg Asn Asp Asn Asn  His Asn Lys
4475            4480                4485

Lys Asn Asp Asp Ser Cys Leu Asn Phe Glu Gln Leu  Asn Glu Ile
```

```
                4490                4495                4500

Ile Gly Asn Gln Thr Tyr Leu Lys Thr Phe Leu Asn Lys Tyr Tyr
    4505                4510                4515

Leu Asn Lys Ser Cys Ile Asn Tyr Asn Glu Lys Phe Glu Gly Lys
    4520                4525                4530

Lys Arg Ile Arg Glu Glu Leu Lys Glu Tyr Tyr Tyr Leu Gln Lys
    4535                4540                4545

Asn Val Tyr Ile Tyr Asn Ser Leu Asn Tyr Leu Asn Ile Asn Tyr
    4550                4555                4560

Lys Asn Trp Leu Leu Val Tyr Lys Thr Tyr Ile Glu Lys Ile Thr
    4565                4570                4575

Tyr Leu Ile Asp Ile Val Leu Lys Ile Lys Ser Asn Thr Val Asn
    4580                4585                4590

Lys Lys Ile Tyr Tyr Leu Lys Asn Tyr Phe Tyr Ile Ile Asn Asn
    4595                4600                4605

Ile Gln Lys His Leu Lys Asn Ile Thr Phe Val Ile Lys Ser Ser
    4610                4615                4620

Tyr Tyr Ile Asn Phe Asn Ile Gln Ile Thr Pro Ile Leu Phe Ile
    4625                4630                4635

Val Tyr Leu Phe Ile Ser Ile Phe Phe Phe Ser His Asn Lys Lys
    4640                4645                4650

Phe Ala Phe Thr Tyr Leu Ser His Ile Asn Lys Gly Phe His Asn
    4655                4660                4665

Leu Phe Lys Asn Lys Lys Asn Phe Met Leu Arg Cys Ile Glu Gln
    4670                4675                4680

Ser Asp Asn Glu Asp Asp Tyr Asp Lys Glu Trp Arg Glu Gln Glu
    4685                4690                4695

Lys Lys Lys Ser Lys Thr Lys Lys Lys Leu Leu Glu Asp Asn Glu
    4700                4705                4710

Lys Leu Gly Asn Glu Gln Gly Asp Lys Thr Asp Gly Lys Asn Lys
    4715                4720                4725

Ser Asn His Asn Asn Asn Glu Asn Asp Asp Asn Glu Asn Asp
    4730                4735                4740

Asp Asn Asn Glu Asn Asp Asp Asp Asn Asp Asn Asp Asp Asp Asp
    4745                4750                4755

Asn Ile Asn Asp Lys Tyr Asp Lys Phe Lys Met Glu Asn Leu Lys
    4760                4765                4770

Tyr Asn Lys Lys Leu Lys Met Ser Ser Leu Phe Ser Lys Lys Ile
    4775                4780                4785

Met His Lys Glu Phe Gln Gly Asn Ile Leu Asn Ile Pro Pro Lys
    4790                4795                4800

Lys Asn Ile Tyr Asn Asp Ser Asn Ile Asn Ile Asn Asp Thr Tyr
    4805                4810                4815

Pro Tyr Met Asp Val Arg Asn Ser Val Asn Glu Leu Arg Gly Ser
    4820                4825                4830

Asn Asn Lys Asn Phe Met Ser Leu Asn Asn Ile Asn Asp Ser Asn
    4835                4840                4845

Val Asn Asn Glu Ser Tyr Leu Asn His His His Asn Asn Asn Thr
    4850                4855                4860

Phe Phe Ser Asp Ser Tyr Tyr Tyr Met Asn Ser Asn Lys Lys Asn
    4865                4870                4875

Leu Lys Lys Lys Asp Val Asn Val Leu Ser Asn Gly Leu Ser Tyr
    4880                4885                4890
```

Asn Asn Asn Asn Asn Ile Asn Leu Ile Asp Asp Leu Tyr Asp His
            4895                    4900                    4905

Phe Ala Asn Ser Glu Lys Ile Tyr Tyr Asp Ile His Asn Glu Tyr
    4910                    4915                    4920

Ser Lys Leu Met Leu Lys Ser Asn Glu Phe Phe Asp Asp Leu Leu
    4925                    4930                    4935

Glu Leu Leu Ile Ile Leu Ile Thr Lys Lys His Pro Ile Leu Asn
    4940                    4945                    4950

Lys Tyr Thr Ile Ile Tyr Ile Tyr Glu Cys Leu Tyr Thr Leu Leu
    4955                    4960                    4965

Asn Ile Tyr His Tyr Asn Asn Asn Asn Asn Asn Asn Asn Tyr Asn
    4970                    4975                    4980

His Asn Asn His Asn Asn Asn Tyr Asn Tyr Tyr Asn Asn Tyr
    4985                    4990                    4995

Asn Asn Asn Tyr Gly Tyr Tyr Asn Ser Ile Ser Asn Asn Glu Glu
    5000                    5005                    5010

Tyr Asp Asn Met Gly His Thr Lys Asn Met Phe Leu Ser Leu Ile
    5015                    5020                    5025

Lys Arg Ile Asp Gln His Ile Leu Asn Gln Phe Ile Ser Thr Leu
    5030                    5035                    5040

Phe Ile Asp Ser Tyr Lys Asn Phe Tyr Ile Asn Arg Asn Thr Ile
    5045                    5050                    5055

Ile Pro Ile Tyr Phe Tyr Asn Asn Ile Tyr Lys Phe Ile Asp Tyr
    5060                    5065                    5070

Asn Thr Glu Val Phe Met Tyr Tyr Glu Gly Lys Lys Lys Ile Tyr
    5075                    5080                    5085

Asn Thr Thr Thr Ala Asn Ser Ser Ser Ser Asn Asn Asn Asp Asn
    5090                    5095                    5100

Tyr Asn Phe Ser Tyr Tyr Pro Asn Lys Gly Thr Asn Lys Gly Gly
    5105                    5110                    5115

Asp Phe His Asp Lys Lys Lys Lys Lys Asn Tyr Tyr Asn Ala Gln
    5120                    5125                    5130

Lys Ser Val His Phe Leu Leu Arg Gly Glu Ser Asn Gln Met Asn
    5135                    5140                    5145

Asn Thr Asn Ile Met Asn Val Asn Lys Lys Lys Ser Asn Phe Ile
    5150                    5155                    5160

Ser Arg Lys Ser Gln Leu Phe Thr Asp Thr Glu Asp Leu Leu Asp
    5165                    5170                    5175

Arg Lys Lys Lys Arg Lys Tyr Lys Thr Arg Gly Lys Lys Tyr Phe
    5180                    5185                    5190

Lys Tyr Asp Ser Asp Ile Asn Tyr Glu Asp Asp Ile His Asp Glu
    5195                    5200                    5205

Asp Asp Asp Asn Asp Asn Asp Asp Asn Asn Asp Asn Asp Asp Asn
    5210                    5215                    5220

Ile Ile Tyr Asn Asn Asn Ser Asp Ile Tyr Asn His Asn Asn Asn
    5225                    5230                    5235

Lys Leu Thr Asn Phe Asn Leu Lys His Gly Leu Lys Asn Gln Ile
    5240                    5245                    5250

His Leu Asn Asn Lys Ser Leu Asn Ile Tyr Glu Glu Ala Tyr Cys
    5255                    5260                    5265

Cys Asn Phe Leu Tyr Asn Lys Asn Asp Leu Asn Leu Leu Ser Ile
    5270                    5275                    5280

Asn Leu Leu Ile Phe Leu Leu Asn Lys Ile Gly Leu Tyr Glu Ile
    5285                    5290                    5295

-continued

```
Asp Ile Lys Ile Asp Glu Asn Asn Ile Lys Asn Val Ile Lys Gly
    5300              5305              5310
Asn Leu Phe Leu Phe His Gln His Leu Asn Lys Gln Leu Glu Asn
    5315              5320              5325
Lys Ile Leu His Thr Cys Phe Leu Leu Cys Ala Leu Cys Asp Thr
    5330              5335              5340
Thr Tyr Ile Asn Glu Phe Val Phe Lys Glu Asp Leu Phe Asn Leu
    5345              5350              5355
Phe Leu Lys Ser Asn Ile Phe Asp Asn Leu Tyr Glu Tyr Lys Phe
    5360              5365              5370
Asn Asn Leu Ser Pro Ser Ile Ser Phe Leu Thr Phe Pro Thr Asn
    5375              5380              5385
Phe Leu Leu Asn Lys Asn Ile Tyr Ile Pro Leu Pro Val Leu Ile
    5390              5395              5400
Ile Ala Tyr Ile Ser Val Ile Leu Lys Val Val Asp Lys Lys Gly
    5405              5410              5415
Leu Tyr Leu Phe Asn Thr Ile Ser Lys Trp Ile Leu Lys Asn Ile
    5420              5425              5430
Asn Ile Phe Ile Asn His Leu Ile Ile Asn Asn Tyr Leu Met Lys
    5435              5440              5445
Ser Asn Glu Ile Ala Tyr Glu Val Asn Asn Phe Thr Thr Asn Asn
    5450              5455              5460
His Asn Leu Ile Tyr Lys Cys Leu Cys Tyr Ser Ser Thr Cys Asn
    5465              5470              5475
Phe Thr Lys His Arg Lys Thr Lys Ser Asn His His Asn Asn Ile
    5480              5485              5490
Met Met His Val Asp Lys Ser Lys Lys Asn Asn His Thr Lys Lys
    5495              5500              5505
Asp Phe Phe Asn Met Lys Asn Asn Asp Leu His Asn Lys Asn Pro
    5510              5515              5520
Leu Leu Phe Asp Ser Leu Tyr Lys Glu Asp Ile His Val Asp Glu
    5525              5530              5535
Asn Lys Ser Glu Glu Tyr Ile Asn His Thr Asn Val Asp Val Val
    5540              5545              5550
Asn Leu Asp Ile Ile Tyr Ser Ser Thr Tyr Tyr Leu Leu Arg Leu
    5555              5560              5565
Tyr Lys Asn Tyr Leu Leu Tyr Ile His Gln Asn Tyr Leu Gly Met
    5570              5575              5580
Lys Lys Leu Lys Ile Ala Glu Met Asn Lys Met Lys Gln Glu Arg
    5585              5590              5595
Arg Lys Leu Asn Ser Lys Lys Lys Lys Thr Ile Thr Glu Asp
    5600              5605              5610
Asn Lys Asp Glu Leu Ile Asp Ser Asp Asp Tyr Glu Glu His
    5615              5620              5625
Glu Asn Val Tyr Glu Glu Glu Asp Tyr Glu Glu Asp Asp Asp Asp
    5630              5635              5640
Glu Asp Asp Asp Asp Asp Asp Asp Asp Asp Asp Asp Asp Asp Asp
    5645              5650              5655
Asp Asn Asn Asn Asn Asn Asn Asn Ile Arg Arg Asn Leu Arg
    5660              5665              5670
Asn Ile Lys Ser Thr Tyr Thr His Leu Tyr Lys Glu Arg Lys Asn
    5675              5680              5685
Lys Tyr Ile Tyr Asn Asn Tyr Asp Asp Asp Asp Tyr Asp Gly Asp
```

|   |   |   |   |   |   |   |   |   |   |
|---|---|---|---|---|---|---|---|---|---|
| | 5690 | | | 5695 | | | 5700 | | |
| Asp | Asp | Ser | Asn | Asn | Ser | Tyr | Asn | Asn | Ile | Phe | Lys | Thr | Gln | Asn |
| | | 5705 | | | | | 5710 | | | | | 5715 | | |
| Asp | Tyr | Asp | Arg | Asn | Thr | Lys | Ile | Tyr | Asn | Lys | Asn | Lys | Leu | Asn |
| | 5720 | | | | | 5725 | | | | | 5730 | | | |
| Asn | Leu | Asn | Asn | Tyr | Tyr | Asp | Thr | Cys | Asn | Asn | Asn | Asn | Asn | Asn |
| 5735 | | | | | 5740 | | | | | 5745 | | | | |
| Leu | Asp | Asp | Tyr | Asn | Lys | Lys | Phe | Ile | Lys | Asp | Asp | Glu | Asn | Phe |
| | 5750 | | | | | 5755 | | | | | 5760 | | | |
| Ile | Leu | Asp | Lys | Thr | Leu | Asn | Phe | Glu | Phe | Asn | Glu | Ile | Ser | Leu |
| | | 5765 | | | | | 5770 | | | | | 5775 | | |
| Asn | Ile | Cys | Asn | Ile | Ile | Lys | Glu | His | Thr | Tyr | Ile | Leu | Gln | Tyr |
| | | | 5780 | | | | | 5785 | | | | | 5790 | |
| Ile | Lys | Asp | Leu | Leu | Asn | Ile | Leu | Ser | Ile | Phe | Val | Ile | Tyr | Asp |
| | 5795 | | | | | 5800 | | | | | 5805 | | | |
| Ile | Ser | Leu | Lys | Asp | Glu | Asn | Asp | Leu | Leu | Asn | Lys | Asn | Leu | Asn |
| 5810 | | | | | 5815 | | | | | 5820 | | | | |
| Asn | Val | Thr | Leu | Glu | Lys | Arg | Lys | Lys | Asn | Ile | Arg | Thr | His | Arg |
| | 5825 | | | | | 5830 | | | | | 5835 | | | |
| Ile | Leu | Gln | Asn | Ile | Ile | Pro | Lys | Tyr | Ser | Ile | Lys | Phe | His | Cys |
| | 5840 | | | | | 5845 | | | | | 5850 | | | |
| Ile | Asn | Leu | Cys | Leu | Asp | Ile | Ile | Glu | Tyr | Asp | Ile | Gly | Leu | Tyr |
| 5855 | | | | | 5860 | | | | | 5865 | | | | |
| Asp | Glu | Tyr | Val | Gln | Gln | Ser | Lys | Thr | Lys | Tyr | Tyr | Glu | Tyr | Ile |
| | 5870 | | | | | 5875 | | | | | 5880 | | | |
| Lys | Ile | Ile | Leu | Lys | Val | Phe | Met | Asn | Thr | Cys | Phe | Tyr | Phe | Ile |
| 5885 | | | | | 5890 | | | | | 5895 | | | | |
| Asn | Ile | Ile | Lys | Tyr | Glu | Asn | Phe | His | Met | Leu | Lys | Ser | Val | Ser |
| 5900 | | | | | 5905 | | | | | 5910 | | | | |
| Met | Ala | Met | Lys | Lys | Leu | Thr | Asn | Ile | Ile | Tyr | Phe | Leu | Leu | Asn |
| | 5915 | | | | | 5920 | | | | | 5925 | | | |
| Asn | Leu | Thr | Ile | Lys | Glu | Lys | Ala | Asn | Asp | Asn | Lys | Asn | Gln | Thr |
| | 5930 | | | | | 5935 | | | | | 5940 | | | |
| Leu | Leu | Asn | Lys | Phe | Ile | Tyr | Asp | Lys | Ser | Gly | Phe | Lys | Lys | Asn |
| | 5945 | | | | | 5950 | | | | | 5955 | | | |
| Ala | His | Glu | Ile | Thr | Thr | Glu | Leu | Phe | Asn | Thr | Asp | Tyr | Asn | Ile |
| | 5960 | | | | | 5965 | | | | | 5970 | | | |
| Phe | Asn | Asp | Lys | Lys | Tyr | Thr | Ser | Asp | Asn | Ile | Lys | Lys | Phe | Leu |
| | 5975 | | | | | 5980 | | | | | 5985 | | | |
| Glu | Asn | Ile | Glu | Ile | Asp | Ile | Leu | Val | Leu | Lys | Lys | Ile | Leu | Thr |
| | 5990 | | | | | 5995 | | | | | 6000 | | | |
| Cys | Val | Ile | Tyr | Phe | Thr | Tyr | Ala | Met | Leu | Ser | Asn | Gln | Lys | Val |
| | 6005 | | | | | 6010 | | | | | 6015 | | | |
| His | Lys | Ile | Asn | Ile | Glu | His | Ile | Asn | Leu | Asn | His | Ile | Asn | Lys |
| | 6020 | | | | | 6025 | | | | | 6030 | | | |
| Ile | Asn | Leu | Lys | Lys | Ile | Ala | Asn | Lys | Tyr | Leu | Glu | Asn | Asn | Asn |
| | 6035 | | | | | 6040 | | | | | 6045 | | | |
| Ile | Leu | Lys | Val | Phe | Thr | Phe | Ile | Leu | Gln | Arg | Ser | Thr | Gln | Ile |
| | 6050 | | | | | 6055 | | | | | 6060 | | | |
| Tyr | Tyr | Leu | Leu | Tyr | Asn | Tyr | Ala | Thr | Lys | Ser | Tyr | Thr | Lys | Trp |
| | 6065 | | | | | 6070 | | | | | 6075 | | | |

<210> SEQ ID NO 22
<211> LENGTH: 426

```
<212> TYPE: PRT
<213> ORGANISM: Plasmodium falciparum

<400> SEQUENCE: 22

Met Glu Lys Tyr Ile His Thr Ser Lys Ser Asn Ser Val Pro Ser Lys
1               5                   10                  15

Gly Tyr Val Asn Arg Tyr Ile Glu Asn Thr Arg Asn Asp Cys Thr Leu
            20                  25                  30

Tyr Lys Cys Ala Lys Lys Gly Gln Tyr Arg Asn Arg Lys Asn Ile Leu
        35                  40                  45

Leu Lys Cys Gly Arg Phe Phe Arg Leu Pro Leu Cys Val Val Ile Tyr
    50                  55                  60

Tyr Ile Ile Leu Met Ser Gln Phe Ile Lys Thr Ile Asn Cys Thr Ser
65                  70                  75                  80

Val Leu Pro Ser Cys Asn Glu Ser Glu Lys Asn Val Ser Lys Asn Ile
            85                  90                  95

Lys Asp Ile Cys Asn Glu Gly Lys Asp Asp Asn Ile Ser Asn Lys Trp
            100                 105                 110

Tyr Glu Glu Asn Lys Arg Ser Leu Asn Gly Glu Tyr Ser Asp Asn Pro
            115                 120                 125

Leu Phe Asp Tyr Lys Leu Phe Lys Tyr His Asp Ile Leu Tyr Lys Gly
        130                 135                 140

Ile Leu Asn Lys Glu Leu Ser Glu Glu Phe Asp Leu Leu Phe Ser Asp
145                 150                 155                 160

Asn Thr Asn Tyr Pro Phe Val Lys Asn Glu Lys Asp Lys Glu Ile Met
            165                 170                 175

Lys Gln Ile Lys Leu Leu Ser Ile Asn Glu Asp Glu Asn Lys Lys Glu
            180                 185                 190

His Met Lys Lys Ile Trp Thr Asp Phe Ile Lys Asn Glu Leu Ser Asn
        195                 200                 205

Phe Leu Phe Leu Lys Lys Lys Ile Ser Asp Leu Phe Glu Glu Leu Lys
    210                 215                 220

Ser Gln Tyr Asn Ile Lys Asp Glu Tyr Val Asn Lys Ile Trp Asn Glu
225                 230                 235                 240

Cys Leu Asp Leu Ile Glu Thr Ser Gly Met Ser Met Asn Thr Asn Leu
            245                 250                 255

Asn Tyr Ala Phe Tyr Lys Trp Tyr Asn Lys Thr Lys Val Leu Asp Ile
            260                 265                 270

Asn Glu Tyr Ile Phe Phe Ile Cys Gly Ile Lys Leu Val Trp Met Lys
        275                 280                 285

Leu Phe Ser Ser Leu Glu Ile Ser Cys Lys Asp Ile Leu Met Lys Cys
    290                 295                 300

Phe Glu Gly Lys Lys Asn Gly Lys Thr Leu Tyr Thr Lys Cys Cys Ser
305                 310                 315                 320

Asp Lys Tyr Lys Asn Phe Phe Lys Asp Ile Asn Lys Lys Ser Phe Ser
            325                 330                 335

Lys Lys Cys Glu Asn Asp Glu Asn Asn Asp Ser Tyr Ser His Ile
            340                 345                 350

Asn His Leu Asn Thr Leu Leu Asn Glu Leu Asp His Leu Ile Ser Leu
        355                 360                 365

Asn Glu Lys Asp Asp Asp Tyr Tyr Thr Leu Arg Gly Tyr Ser Ser Asn
    370                 375                 380

Lys Arg Val Glu Leu Thr Asp Ile Phe Arg Leu Leu Cys Lys Met Asp
385                 390                 395                 400
```

```
Ser Ala Asp Met Leu Thr Trp Phe Val His Asn Phe Phe Gly Phe Ser
            405                 410                 415

Lys Lys Phe Arg Gln Tyr Leu Tyr Lys Met
            420                 425

<210> SEQ ID NO 23
<211> LENGTH: 110
<212> TYPE: PRT
<213> ORGANISM: Plasmodium falciparum

<400> SEQUENCE: 23

Met Ser Phe Tyr Tyr Phe Lys Leu Ser Phe Ile Ser Ile Leu Leu Cys
1               5                   10                  15

Ile Leu Ile Ile Thr His Lys Phe Ser Leu Glu Gln Ile Thr His Asn
            20                  25                  30

Lys Ser Asn Asn Phe Asn Ile Ile Asn Val Thr His Arg Arg Leu Leu
        35                  40                  45

Ala Glu Pro His Lys Ser His Ile Leu Lys Thr His Lys Gly Glu Asn
    50                  55                  60

Ser Met Ala Gln Pro Ile Val Asn Lys Leu Arg Glu Asn His Thr Glu
65                  70                  75                  80

Cys Pro Lys Lys Ser Ser Ile Lys Leu Lys Lys Ile Leu Ile Leu
                85                  90                  95

Val Ser Leu Phe Thr Leu Pro Cys Ser Phe Phe Cys Phe Gln
            100                 105                 110

<210> SEQ ID NO 24
<211> LENGTH: 653
<212> TYPE: PRT
<213> ORGANISM: Plasmodium falciparum

<400> SEQUENCE: 24

Met Tyr Ser Ala Leu Arg Ser Phe Leu Phe Arg Lys Ser Val Val Ser
1               5                   10                  15

Val Ile Gly Val Leu Val Ala Leu Leu Asn Asn Glu Cys Ser Glu Asp
            20                  25                  30

Gly Leu Phe Ser Ser His Tyr Leu Asn Ser Arg Phe Ser Arg Ile Leu
        35                  40                  45

Ser Ser Ala Asn Asn Gly Asn Glu Tyr Asp Ile Leu Asp Leu Gly Ile
    50                  55                  60

Pro Ser Val Phe Ser Val Phe Ser Leu Ser Lys Glu Glu Met Met Thr
65                  70                  75                  80

Leu Leu Lys Asp Val Tyr Gly Lys Thr Lys Lys Val Asn Leu Ser Asp
                85                  90                  95

Glu Glu Lys Ile Ile Arg Asp Ile Lys Lys Tyr Gly Met Ser Cys Asn
            100                 105                 110

Tyr Ser Ala Ile Pro Tyr Ile Asp Glu Phe Gly Leu Val Val Tyr Asn
        115                 120                 125

Lys Ile Asp Asn Glu Leu Asp Ala Asp Phe Asn Asp Leu Asp Glu Leu
    130                 135                 140

Ser Glu Thr Phe Lys Asp Asp Ala Tyr Asn His Trp Val Arg Val Met
145                 150                 155                 160

Lys Asn Glu Glu Ser Lys Tyr Phe Gln Asn Phe Val Asp Leu Ser Thr
                165                 170                 175

Tyr Tyr Asp Thr Leu Lys Lys Glu Asn Leu Ile Leu Asp Asn Tyr Lys
            180                 185                 190

Glu Asp Lys Leu Asn Glu Cys Arg His Ile Val Pro Leu Lys Ala Gln
```

-continued

```
                195                 200                 205
Lys Leu Ile Pro Gly Leu Thr Lys Ile Phe Glu Asp Trp Thr Lys Asn
210                 215                 220

Glu Ile Leu Tyr Lys Arg Glu Phe Glu Thr Leu Ile Asn Ser Val Arg
225                 230                 235                 240

Ile Ala Trp Lys Ala Leu Thr Asn Tyr Ala Leu Tyr Glu Cys Lys Asn
            245                 250                 255

Ile Phe Ile Lys Asn Leu Asp Glu Ile Glu Asp Val Asp Glu Glu Glu
            260                 265                 270

Glu Glu Glu Glu Glu Lys Glu Glu Lys Glu Ser Arg Lys Ser Lys
            275                 280                 285

Lys Ser Lys Lys Lys Glu Thr Glu Thr Asp Glu Lys Lys Asp Glu
290                 295                 300

Lys Glu Lys Asp Glu Lys Glu Lys Asp Val Asn Glu Lys Asp Glu Lys
305                 310                 315                 320

Glu Lys Asp Glu Lys Glu Lys Asp Val Asn Glu Lys Asp Glu Lys Glu
            325                 330                 335

Lys Asp Glu Lys Glu Lys Asp Glu Lys Glu Lys Asp Glu Lys Glu Lys
            340                 345                 350

Asp Glu Lys Glu Lys Asp Glu Lys Glu Lys Asp Glu Lys Glu Lys Asp
            355                 360                 365

Glu Lys Lys Lys Asp Glu Lys Glu Lys Asp Glu Lys Glu Lys Asp Glu
            370                 375                 380

Lys Glu Lys Lys Val Ser Asn Ile Lys Asn Asn Leu Arg Ala Val Pro
385                 390                 395                 400

Gln Asn Ser Gly Ser Asn Phe Asp Glu Phe Leu Asp Val Lys Glu Ala
            405                 410                 415

Asn Glu Ile Val Gln Asp Val Leu Gln Glu Phe Val Glu Gly Lys Ile
            420                 425                 430

Ser Glu Glu Asp Lys Gln Lys Tyr Ala Glu Asn Leu Asp Asp Asp
            435                 440                 445

Asp Glu Asp Asp Glu Glu Asp Asp Asp Glu Asp Asp Glu Asp Asn
450                 455                 460

Asp Asp Asp Glu Asp Asp Asp Asp Asp Glu Asp Asn Asp Asp
465                 470                 475                 480

Glu Asp Asp Glu Asp Asn Asp Asp Glu Asp Asn Asp Asp
            485                 490                 495

Glu Asp Asp Glu Asp Asn Asp Asp Asp Glu Glu Asp Lys Gly Val
            500                 505                 510

Tyr Asn Leu Lys Lys Asp Glu Thr Ala Thr Ile Asn Lys Asp Ile Lys
            515                 520                 525

Glu Leu Glu Glu Val Ile Ser Val Glu Asp Ile Thr Asn Ile Ser Leu
            530                 535                 540

Lys Ile Thr Ser Asn Glu Asn Asn Lys Val Ala Ile Leu Lys Asn Glu
545                 550                 555                 560

Leu Ser Asp Phe Tyr Arg Lys Gln Cys Glu Lys His Lys Val Lys Val
            565                 570                 575

Glu Gly Ser Arg Gly Val Leu Lys Ser Cys Tyr Asn Leu Ile Lys Ser
            580                 585                 590
```

-continued

```
Glu Leu Glu Lys Leu Gln Gly Ser Leu Asn Lys Tyr Tyr Leu Ser Leu
        595             600             605

Leu Lys Ala Asn Val Leu Thr Lys Lys Asp Ala Glu Lys Tyr Ile Asp
    610             615             620

Asn Cys Leu Asp Ser Tyr Asp Asp Phe Arg Lys Lys Met Lys Glu Thr
625             630             635             640

Cys Glu Gln Lys Ile Ile Lys Tyr Phe Asn Asn Glu Asp
            645             650
```